United States Patent
Voldborg et al.

(10) Patent No.: US 11,624,080 B2
(45) Date of Patent: Apr. 11, 2023

(54) GLYCOSYLATION OF PROTEINS

(71) Applicant: DANMARKS TEKNISKE UNIVERSITET, Kongens Lyngby (DK)

(72) Inventors: Bjørn Gunnar Voldborg, Hillerød (DK); Stefan Kol, Copenhagen (DK); Anders Holmgaard Hansen, Rødovre (DK); Helene Faustrup Kildegaard, Værløse (DK)

(73) Assignee: DANMARKS TEKNISKE UNIVERSITET, Kongens Lyngby (DK)

( * ) Notice: Subject to any disclaimer, the term of this patent is extended or adjusted under 35 U.S.C. 154(b) by 0 days.

(21) Appl. No.: 16/767,531

(22) PCT Filed: Nov. 16, 2018

(86) PCT No.: PCT/EP2018/081616
§ 371 (c)(1),
(2) Date: May 27, 2020

(87) PCT Pub. No.: WO2019/105770
PCT Pub. Date: Jun. 6, 2019

(65) Prior Publication Data
US 2021/0262000 A1    Aug. 26, 2021

(30) Foreign Application Priority Data

Nov. 28, 2017 (EP) .................... 17204071
Jul. 11, 2018 (EP) .................... 18182948

(51) Int. Cl.
| | | |
|---|---|---|
| *C12P 21/00* | (2006.01) | |
| *C07K 14/81* | (2006.01) | |
| *C12N 9/10* | (2006.01) | |

(52) U.S. Cl.
CPC ............ *C12P 21/005* (2013.01); *C07K 14/81* (2013.01); *C12N 9/1081* (2013.01); *C12Y 204/99001* (2013.01)

(58) Field of Classification Search
None
See application file for complete search history.

(56) References Cited

U.S. PATENT DOCUMENTS

| | | |
|---|---|---|
| 8,623,611 B2 | 1/2014 | Pierce et al. |
| 2014/0349341 A1 | 11/2014 | Lin et al. |

FOREIGN PATENT DOCUMENTS

| | | |
|---|---|---|
| WO | 2008/151845 A2 | 12/2008 |
| WO | 2009/009086 A2 | 1/2009 |
| WO | 2010/127939 A1 | 11/2010 |
| WO | 2013/096458 A1 | 6/2013 |
| WO | WO-2013/106515 A1 | 7/2013 |
| WO | 2015/092737 A1 | 6/2015 |
| WO | WO-2015/134488 A1 | 9/2015 |
| WO | 2016/091268 A2 | 6/2016 |
| WO | 2017/008982 A1 | 1/2017 |
| WO | WO-2020/047282 A1 | 3/2020 |

OTHER PUBLICATIONS

Information for clone hMU001448 from Korean Human Gene Bank (KHBB) retrieved from < https://genbank.kribb.re.kr/resource/human/list?s=all&f=all&t=cloneid&k=hMU001448 > on Jan. 7, 2022.*
Blanchard et al., N-glycosylation and biological activity of recombinant human alpha1-antitrypsin expressed in a novel human neuronal cell line, Biotechnology and Bioengineering, 108(2):2118-2128 (2011).
Castilho et al., Proteolytic and N-glycan processing of human (Alpha)1-antitrypsin expressed in nicotiana benthamiana, Plant Physiology, 166:1839-1851 (2014).
Fan et al., Improving the efficiency of CHO cell line generation using glutamine synthetase gene knockout cells, Biotechnology and Bioengineering, 109(4):1007-1015 (2011).
Ghaedi et al., Expression of recombinant alpha-1 antitrypsin in CHO and COS-7 cell lines using lentiviral vector, Iranian Journal of Biotechnology, 7(3):148-156 (2009).
Grav et al., One-step generation of triple knockout CHO cell lines using CRISPR/Cas9 and fluorescent enrichment, Biotechnol. J., 10(9):1446-1456 (2015).
Lee et al., N-glycan analysis of human [alpha]1-antitrypsin produced in Chinese hamster ovary cells, Glyco. J., 30(5):537-547 (2013).
Ronda et al., Accelerating genome editing in CHO cells using CRISPR/Cas9 and CRISPy, a web-based target finding tool, Biotechnol. Bioeng., 111(8):1604-1616 (2014).
Voss et al., Shedding of glycan-modifying enzymes by signal peptide peptidase-like 3 (SPPL3) regulates cellular N-glycosylation, EMBO J., 33(24):2890-2905 (2014).
Yang et al. Engineered CHO cells for production of diverse, homogeneous glycoproteins, Nat. Bio., 33(8):842-844 (2015).
Fukuta et al., Genetic engineering of CHO cells producing human interferon-(gamma) by transfection of sialyltransferases, Glycoconjugate Journal, 17:895-904 (2000).
Weikert et al., Engineering chinese hamster ovary cells to maximize sialic acid content of recombinant glycoproteins, Nat. Biotech. ,17:1116-1121 (1999).

(Continued)

*Primary Examiner* — Suzanne M Noakes

(74) *Attorney, Agent, or Firm* — Marshall, Gerstein & Borun LLP

(57) ABSTRACT

The present invention relates to the finding of methods to shift the glycosylation profile of recombinant produced semm glycoproteins to the predominant bi-antennary form found in human plasma. This is accomplished by providing a mammalian cell line according to the invention with a series of gene disruptions and/or gene insertions that facilitate this shift.

24 Claims, 21 Drawing Sheets

Figure 1:
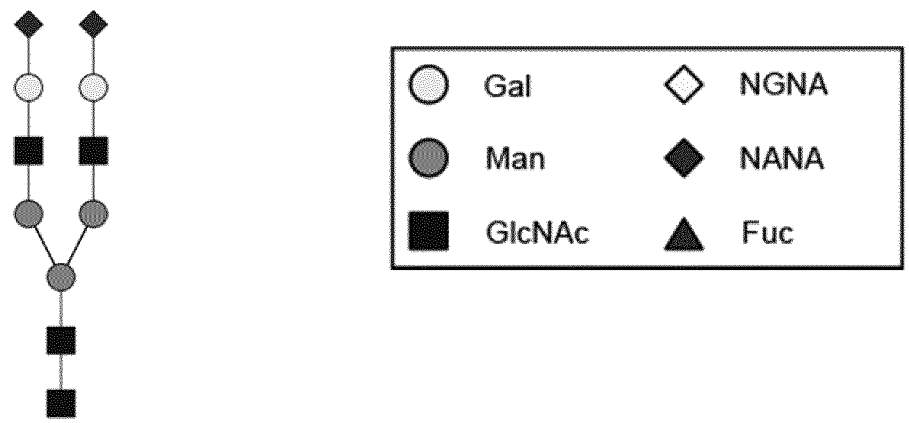

Specification includes a Sequence Listing.

(56) References Cited

OTHER PUBLICATIONS

Bhattacjaryya et al., "Biological Consequences of Inactivating the Mgat3 Gene that encodes GlcNAc-TIII," Glycobiology, vol. 10, No. 10, p. 1081 (2000).

Buffone et al., "Silencing α 1,3-Fucosyltransferases in Human Leukocytes Reveals a Role for FUT9 Enzyme During E-selectin-mediated Cell Adhesion," Journal of Biological Chemistry, vol. 288, No. 3, pp. 1620-1633 (2013).

Jacobs et al., "Engineering complex-type N-glycosylation in Pichia pastoris using GlycoSwitch technology," Nature Protocols, vol. 4, No. 1, pp. 58-70 (2009).

Johswich, et al., "N-glycan remodeling on glucagon receptor is an effector of nutrient sensing by the hexosamine biosynthesis pathway," Journal of Biological Chemistry, vol. 289, No. 23, pp. 15927-15941 (2014).

Kanda et al., "Comparison of Cell Lines for Stable Production of Fucose-Negative Antibodies With Enhanced ADCC," Wiley InterScience, pp. 680-688 (Apr. 11, 2006).

Ohtsubo et al., "Production and characterization of mice lacking the N-glycan GlcNAcT-IV biosynthetic and branching glycosyltransferases encoded by the Mgat4a and Mgat4b genes," Meeting Abstract from FASEB Meeting on Experimental Biology: Translating the Genome; San Diego, Ca, USA; A178, 125.10 (Apr. 11-15, 2003).

Shi et al., "Inactivation of the Mgat1 Gene in Oocytes Impairs Oogenesis, but Embryos Lacking Complex and Hybrid N-Glycans Develop and Implant," Molecular and Cellular Biology, vol. 24, No. 22, pp. 9920-9929 (2004).

Wong et al., "Enhancement of DNA Uptake in FUT8-Deleted CHO Cells for Transient Production of Afucosylated Antibodies," Biotech and Bioengineering, vol. 106, No. 5, pp. 751-763 (Aug. 2010).

Yang et al., "Engineered CHO cells for production of diverse, homogeneous glycoproteins," Nature Biotechnology, vol. 33, No. 8, pp. 842-845 (Aug. 2015).

\* cited by examiner

Figure 17

Table 4: Nucleotide sequences for overexpression vectors.

| vector | |
|---|---|
| SerpinG1-plasmid (SEQ ID NO: 31)<br><br>AmpR<br><br>Bla promoter<br><br>SV40pA<br><br>GLUL<br><br>SV40 promoter<br><br>mCMV-hEF-1a-5' promoter<br><br>C1INH/ SerpinG1 | agacgtcaTGCAGGAAAGAACATGTGAGCAAAAGGCCAGCAAAAGGCCAGGAACCGTAAAAAGGCCGCGTTG
CTGGCGTTTTTTCCATAGGCTCCGCCCCCCTGACGAGCATCACAAAAATCGACGCTCAAGTCAGAGGTGGCGA
AACCCGACAGGACTATAAAGATACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGCGCTTTCTCAATGCTCACGCTGT
AGGTATCTCAGTTCGGTGTAGGTCGTTCGCTCCAAGCTGGGCTGTGTGCACGAACCCCCCGTTCAGCCCGAC
CGCTGCGCCTTATCCGGTAACTATCGTCTTGAGTCCAACCCGGTAAGACACGACTTATCGCCACTGGCAGCA
GCCACTGGTAACAGGATTAGCAGAGCGAGGTATGTAGGCGGTGCTACAGAGTTCTTGAAGTGGTGGCCTAA
CTACGGCTACACTAGAAGGACAGTATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTTTTTGTTTGCAAGCAGCAGATTAC
GCGCAGAAAAAAAGGATCTCAAGAAGATCCTTTGATCTTTTCTACGGGGTCTGACGCTCAGTGGAACGAAAA
CTCACGTTAAGGGATTTTGGTCATGAGATTATCAAAAAGGATCTTCACCTAGATCCTTTTAAATTAAAAATGAA
GTTTTAAATCAATCTAAAGTATATATGAGTAAACTTGGTCTGACAG**TTACCAATGCTTAATCAGTGAGGCA
CCTATCTCAGCGATCTGTCTATTTCGTTCATCCATAGTTGCCTGACTCCCCGTCGTGTAGATAACTAC
GATACGGGAGGGCTTACCATCTGGCCCCAGTGCTGCAATGATACCGCGAGACCCACGCTCACCGGC
TCCAGATTTATCAGCAATAAACCAGCCAGCCGGAAGGGCCGAGCGCAGAAGTGGTCCTGCAACTTT
ATCCGCCTCCATCCAGTCTATTAATTGTTGCCGGGAAGCTAGAGTAAGTAGTTCGCCAGTTAATAGT
TTGCGCAACGTTGTTGCCATTGCTACAGGCATCGTGGTGTCACGCTCGTCGTTTGGTATGGCTTCATT
CAGCTCCGGTTCCCAACGATCAAGGCGAGTTACATGATCCCCCATGTTGTGCAAAAAAGCGGTTAGC
TCCTTCGGTCCTCCGATCGTTGTCAGAAGTAAGTTGGCCGCAGTGTTATCACTCATGGTTATGGCAG
CACTGCATAATTCTCTTACTGTCATGCCATCCGTAAGATGCTTTTCTGTGACTGGTGAGTACTCAACC
AAGTCATTCTGAGAATAGTGTATGCGGCGACCGAGTTGCTCTTGCCCGGCGTCAATACGGGATAATA
CCGCGCCACATAGCAGAACTTTAAAAGTGCTCATCATTGGAAAACGTTCTTCGGGGCGAAAACTCTC
AAGGATCTTACCGCTGTTGAGATCCAGTTCGATGTAACCCACTCGTGCACCCAACTGATCTTCAGCA
TCTTTTACTTTCACCAGCGTTTCTGGGTGAGCAAAAACAGGAAGGCAAAATGCCGCAAAAAAGGGA
ATAAGGGCGACACGGAAATGTTGAATACTCAT**ACTCTTCCTTTTTCAATATTATTGAAGCATTTATCAGGG
TTATTGTCTCATGAGCGGATACATATTTGAATGTATTTAGAAAAATAAACAAATAGGGGTTCCGCGCACATTTC
CCCGAAAAGTGCCACCTGACGTCGACGGATCGGGAGATCTCCCGATCCCCTATGGTCGACTCTCAGTACAAT
CTGCTCTGATGCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTAGGGTTAGGCG
TTTTGCGCTGCTTCGCGA*CAGACATGATAAGATACATTGATGAGTTTGGACAAACCACAACTAGAATGCAGTG
AAAAAAATGCTTTATTTGTGAAATTTGTGATGCTATTGCTTTATTTGTAACCATTATAAGCTGCAATAAACAAG
TTCCGCGG*TTAGTTTTTGTATTGGAAGGGCTGGTCGCCAGTCTCATTGAGAAGGCATGTGCGGACGA
TGGCTTCTGTCACTGCAAAGGGGTCACAATTGGCAGAGGGGCGGCGGTCTTCAAAGTAACCTTTCTT
CTCCTGGCCGACAGTCCGGGAAATGCGGATGCTGGCACTGCGATTGGCGACACCAGCAGAAAAGTC
GTTGATGTTGGACGTTTCGTGGAACCCAGTCAGACGACGGGCATTGTCCAGGCCCCCCTTGGGATCG
TAGGCTCGAATGTGGTACCGGTGCCGCTTGCTTAGTTTCTCGATGGCCTCCTCGATGTGCTTCAGAC
CATTCTCCTCCCGCATGGCCTTGGTGCTAAAGTTGGTATGGCAGCCTGCACCATTCCAGTTCCCAGG
AATGGGCTTGGGGTCAAAGGTTGCTATTACCCCAAAGTCTTCACATACTCGATGCAAGATGAAACGG
GCCACCCAGAGATGATCTCCCCATGCGGATTCCTTCACAGGGTCCTATTTGGAATTCCCACTGGGCAG
GCATGACCTCAGCATTTGTTCCTGTAATCTTGACCCCAGCATACAAGCAGGCGCGGTAGTGAGCCTC
CACGATATCCCTGCCATAGGCTTTGTCTGCGCCCACACCACACATAATACGGACCTTGGGGGCCAGGA
AAGCCATTGGAAGGCCAACCAAAAAGGGTGCCCATCTGTTCCCATCAGAGTATACTCCTGTTCCATTC
CAAACCAGGGGTGCTGGTTGCTCACCATGTCCATTATCCGTTTACACGAGTGCCTTAAATTGGTCTCT
GCAGGCTTCCGGTTGTACTTGAAAACTTCACAGAACACCAGCTTGTTGGGATCTCTGCGGAAGGGGT
CCCGAAACATGGCAACAGGGCTGAGATACATGTCACTGTTGGAGCCCTCAGACTGAAAGGTACTAG
AGCCATCAAAATTCCACTCAGGTAACTCTTCTACACACTTGGGCTCACAGTCCAGGGTGCGGGTTTT
GCAGCGCAGTCCTTCTCCAGTACCATCAACCCAGATATACATGGCTTGGACTTTCTCACCCTGGGGC
AGGCACAAGTACATTTGCTTGATGTTTTTGTTCAAGTGGGAACTTGCTGAGGTGGCCATATCGATCGA
AAATGGATATACAAGCTCCCGGGACGTTTTTGCAAAAGCCCTAGGCCCTCCAAAAAAGCTCCTCACTACTTCTG
GAATAGCTCAGAGGCAGAGGCGGCCTCGGCCTCTGCATAAATAAAAAAAATTAGTCAGCCATGGCGGAG
AATGGGCGGAACTGGGCGGAGTTAGGGGCGGGATGGGCGGAGTTAGGGGCGGGACTATGGTTGCTGACTA
ATTGAGATGCATGCTTTGCATACTTCTGCCTGCTGGGGAGCCTGGGACTTTCCACACCTGGTTGCTGACTA
ATTGAGATGCATGCTTTGCATACTTCTGCCTGCTGGGGAGCCTGGGACTTTCCACACCCTAACTGACACAC
ATTCCACAGACGTCGCTCGATGTACGGGCCAGATATACGCGTAGTCAATGGGAAAAACCCATTGGAGCCAAG
TACACTGACTCAATAGGGACTTTCCATTGGGTTTTGCCCAGTACATAAGGTCAATAGGGGGTGAGTTGCAACAG
GAAAGTCCCATTGGAGCCAAGTACATTGAGTCAATAGGGACTTTCCAATGGGTTTTGCCCAGTACATAAGGT
CAATGGGAGGTAAGCCAATGGGTTTTTTCCCATTACTGACATGTATACTGAGTCATTAGGGACTTTCCAATGGG
TTTTGCCCAGTACATAAGGTCAATAGGGGTGAATCAACAGGAAAGTCCCATTGGAGCCAAGTACACTGAGTC
AATAGGGACTTTCCATTGGGTTTTGCCCAGTACAAAAGGTCAATAGGGGGTGAGTCAATGGGTTTTTCCCATT
ATTGGCACATACATAAGGTCAATAGGGGTGACTAGTCAGTGGGCAGAGCGCACATCGCCCACAGTCCCCGA
GAAGTTGGGGGGAGGGGTCGGCAATTGAACCGGTGCCTAGAGAAGGTGGCGCGGGGTAAACTGGGAAAGT
GATGTCGTGTACTGGCTCCGCCTTTTTCCCGAGGGTGGGGGAGAACCGTATATAAGTGCAGTAGTTGCCGTG
AACGTTCTTTTTCGCAACGGGTTTGCCGCCAGAACACAGCTGAAGCTTCGAGGGGCTCGCATCTCTCCTTCA
CGCGCCCGCCGCCCTACCTGAGGCCGCCATCCACGCCGGTTGAGTCGCGTTCTGCCGCCTCCCGCCTGTGG |

Figure 17 (continued)

| | |
|---|---|
| BGHpA<br><br>mCMV-<br>hEF-1a-5'<br>promoter<br><br><br><br><br><br><br><br><br><br>ST6GAL1<br><br><br><br><br><br><br><br><br><br><br><br><br>BGHpA | TGCCTCCTGAACTGCGTCCGCCGTCTAGGTAAGTTTAAAGCTCAGGTCGAGACCGGGCCTTTGTCCGGCGCT<br>CCCTTGGAGCCTACCTAGACTCAGCCGGCTCTCCACGCTTTGCCTGACCCTGCTTGCTCAACTCTACGTCTTT<br>GTTTCGTTTTCTGTTCTGCGCCGTTACAGATCCAAGCTGTGACCGGCGCCTACagtgcgatCGCCACCATGGCC<br>AGCAGACTGACACTGCTGACCCTGCTGCTCCTCCTGCTGGCTGGAGACAGGGCTTCCTCCAACCCCA<br>ACGCCACCAGCAGCAGCTCCCAGGACCCTGAGTCCCTCCAGGACAGGGGAGAAGGCAAGGTCGCCA<br>CCACCGTCATCTCCAAAATGCTCTTCGTCGAGCCCATCCTCGAGGTCAGCTCCCTCCCCACCACAAAC<br>AGCACAACCAACAGCGCCACCAAGATCACCGCCAACACCACCGACGAACCCACAACCCAGCCCACC<br>ACAGAGCCTACAACACAGCCTACCATCCAGCCTACCCAACCCACCACCCAGCTCCCTACCGACTCCC<br>CTACCCAGCCTACCACAGGCTCCTTTTGTCCCGGACCTGTGACCCTGTGCTCCGACCTGGAGTCCCAT<br>AGCACAGAGGCTGTCCTCGGAGATGCCCTGGTGGATTTCAGCCTCAAACTCTACCACGCCTTCAGCG<br>CCATGAAGAAGGTCGAGACCAATATGGCCTTCTCCCCCTTTAGCATCGCCAGCCTGCTCACCCAAGT<br>CCTGCTCGGAGCCGGCGAGAATACCAAGACCAACCTGGAGAGCATCCTGTCCTACCCTAAGGACTTG<br>ACCTGCGTCCACCAGGCCCTCAAGGGCTTTACCACCAAAGGAGTCACATCCGTCAGCCAGATCTTCC<br>ATTCCCCTGACCTCGCCATTAGGGACACATTCGTGAACGCCTCCAGGACCCTGTACAGCAGCTCCCC<br>TAGGGTCCTGTCCAACAACAGCGACGCCAACCTGGAGCTCATTAATACATGGGTGGCCAAGAATAC<br>AAACAACAAGATTAGCAGGCTCCTGGATAGCCTGCCTTCCGACACCAGGCTCGTGCTCCTCAATGCC<br>ATCTACCTCTCCGCCAAGTGGAAGACCACATTCGACCCCAAGAAAACAAGGATGGAGCCCTTCACT<br>TTAAAAATAGCGTGATCAAGGTGCCCATGATGAACAGCAAGAAGTACCCTGTCGCCCACTTCATCGA<br>CCAGACCCTGAAGGCTAAGGTGGGACAGCTCCAACTGTCCCATAATCTGAGGCCTGGTCATCCTCGTG<br>CCTCAGAACCTGAAGCACAGGCTGGAGGACATGGAACAGGCCCTGTCCCCCAGCGTGTTTAAGGCG<br>ATCATGGAAAAACTCGAGATGTCCAAGTTTCAACCCACCCTCCTCACCCTGCCCAGAATTAAGGTCA<br>CCACAAGCCAGGACATGCTCAGCATTATGGAGAAGCTCGAGTTCTTCGATTTCTCCTACGACCTCAA<br>CCTCTGCGGCCTGACAGAAGACCCTGACCTGCAGGTGAGCGCCATGCAGCACCAGACAGTGCTGGA<br>GCTCACCGAGACAGGAGTGGAAGCTGCTGCCGGCCTCCGCTATTTCCGTGGCCAGGACCCTCCTGGTG<br>TTCGAGGTGCAACAACCCTTCCTGTTCGTCCTGTGGGACCAACAACAAGTTCCCTGTGTTCATGG<br>GCAGAGTCTACGACCCCAGAGCCTGAacacagtct*CTGTGCCTTCTAGTTGCCAGCCATCTGTTGTTTGC*<br>*CCCTCCCCGTGCCTTCCTTGACCCTGGAAGGTGCCACTCCCACTGTCCTTTCCTAATAAAATGAGGA*<br>*AATTGCATCGCATTGTCTGAGTAGGTGTCATTCTATTCTGGGGGGTGGGGTGGGGCAGGACAGCAA*<br>*GGGGGAGGATTGGGAAGACAATAGCAGGCATGCTGGGGATGCGGTGGGCTCTATGG*ATTAAGCTCG<br>CGTAGTCAATGGGAAAAACCCATTGGAGCCAAGTACACTGACTCAATAGGGACTTTCCATTGGGTTTTGCCC<br>AGTACATAAGGTCAATAGGGGGTGAGTCAACAGGAAAAGTCCCATTGGAGCCAAGTACATTGAGTCAATAGG<br>GACTTTCCAATGGGTTTTGCCCAGTACATAAGGTCAATGGGAGGTAAGCCAATGGGTTTTTCCCATTACTGAC<br>ATGTATACTGAGTCATTAGGGACTTTCCAATGGGTTTTGCCCAGTACATAAGGTCAATAGGGGTGAATCAACA<br>GGAAAGTCCCATTGGAGCCAAGTACACTGAGTCAATAGGGACTTTCCATTGGGTTTTGCCCAGTACAAAAGG<br>TCAATAGGGGGTGAGTCAATGGGTTTTTCCCATTATTGGCACATACATAAGGTCAATAGGGGTGACTAGTCA<br>GTGGGCAGAGCGCACATCGCCCACAGTCCCCGAGAAGTTGGGGGGAGGGGTCGGCAATTGAACCGGTGCC<br>TAGAGAAGGTGGCGCGGAGGTAAACTGGGAAAGTGATGTCGTGTACTGGCTCCGCCTTTTTTCCCGAGGGTGG<br>GGGAGAACCGTATATAAGTGCAGTAGTTGCCGTGAACGTTCTTTTTCGCAACGGGTTTGCCGCCAGAACACA<br>GCTGAAGCTTCGAGGGGCTCGCATCTCTCCTTCACGCGCCCGCCGCCCTACCTGAGGCCGCCATCCACGCC<br>GGTTGAGTCGCGTTCTGCCGCCTCCCGCCTGTGGTGCCTCCTGAACTGCGTCCGCCGTCTAGGTAAGTTTAA<br>AGCTCAGGTCGAGACCGGGCCTTTGTCCGGCGCTCCCTTGGAGCCTACCTAGACTCAGCCGGCTCTCCACG<br>CTTTGCCTGACCCTGCTTGCTCAACTCTACGTCTTTGTTTCGTTTTCTGTTCTGCGCCGTTACAGATCCAAGCT<br>GTGACCGGCGCCTACagtgcgatCGCCACCATGATCCACACCAACCTGAAGAAGAAATTCTCCTGCTGCGTGCT<br>GGTGTTCCTGCTGTTCGCCGTGATCTGCGTGTGGAAGGAAGAAGGGCTCCTACTACGACTCCTTCAA<br>GCTGCAGACCAAAGAATTCCAGGTGCTGAAGTCCCTGGGCAAGCTGGCCATGGGCTCCGACTCTCAGTCCG<br>TGTCCTCCAGCTCTACCCAGGACCCCCACAGAGGCAGACAGACCCTGGGCTCTCTGAGAGGCCTGGCCAAG<br>GCTAAGCCTGAGGCCTCCTTCCAGGTGTGGAACAAGGACTCCTCCAGCAAGAACCTGATCCCCCGGCTGCA<br>GAAGATCTGGAAGAACTACCTGTCCATGAACAAGTACAAGGTGTCCTACAAGGGCCCTGGCCCTGGCATCAA<br>GTTCTCTGCCGAGGCCCTGAGATGCCACCTGAGGGACCATGTGAACGTGTCCATGGTGGAAGTGACCGACT<br>TCCCATTCAACACCTCCGAGTGGAGGGCTACCTGCCCAAGAGTCCATCCGACCAAGGCTGGCCCTTGG<br>GGCAGATGTGCTGTGGTGTCCTCTGCCGGCTCCCTGAAGTCCTCTCAGCTGGGCAGAGAGATCGACGACCA<br>CGACGCCGTGCTGCGGTTTAATGGCGCCCCTACCGCCAACTTCCAGCAGGACGTGGGCACCAAGACCACCA<br>TCCGGCTGATGAACTCCAGCTCGTGACAACCGAGAAGCGGTTCCTGAAGGACTCCCTGTACAACGAGGGC<br>ATCCTGATCGTGTGGGACCCCTCCGTGTACCACTCCGACATCCCCAAGTGGTATCAGAACCCCGACTACAAC<br>TTCTTCAACAACTACAAGACCTACCGGAAGCTGCACCCCAACCAGCCCTTCTACATCCGTGAAGCCCCAGATGC<br>CCTGGGAGCTGTGGGACATTCTGCAGGAAATCTCCCCCGAGGAAATCCAGCCCAACCCCCTTCCTCTGGCA<br>TGCTGGGCATCATTATCATGATGACCCTGTGCGACCAGGTGGACATCTACGAGTTTCTGCCCTCCAAGAAA<br>AGACCGACGTGTGCTACTACTACCAGAAGTTCTTCGACTCCGCCTGCACCATGGGCGCCTACCACCCTCTGC<br>TGTACGAGAAGAACCTCGTGAAGCACCTGAACCAGGGCACCGACGAGGATATCTACCTGCTGGGCAAGGCC<br>ACCCTGCCTGGCTTCAGAACCATCCACTGCTGAacacagtct*CTGTGCCTTCTAGTTGCCAGCCATCTGTTGT*<br>*TTGCCCCTCCCCGTGCCTTCCTTGACCCTGGAAGGTGCCACTCCCACTGTCCTTTCCTAATAAAATG*<br>*AGGAAATTGCATCGCATTGTCTGAGTAGGTGTCATTCTATTCTGGGGGGTGGGGTGGGGCAGGACA*<br>*GCAAGGGGGAGGATTGGGAAGACAATAGCAGGCATGCTGGGGATGCGGTGGGCTCTATGG* |
| A1AT<br>plasmid<br>(SEQ ID<br>NO: 32) | agacgtcaTGCAGGAAAGAACATGTGAGCAAAAGGCCAGCAAAAGGCCAGGAACCGTAAAAAGGCCGCGTTG<br>CTGGCGTTTTTCCATAGGCTCCGCCCCCCTGACGAGCATCACAAAAATCGACGCTCAAGTCAGAGGTGGCGA<br>AACCCGACAGGACTATAAAGATACCAGGCGTTTCCCCCTGGAAGCTCCCTCGTGCGCTCTCCTGTTCCGACC<br>CTGCCGCTTACCGGATACCTGTCCGCCTTTCTCCCTTCGGGAAGCGTGGCGCTTTCTCAATGCTCACGCTGT<br>AGGTATCTCAGTTCGGTGTAGGTCGTTCGCTCCAAGCTGGGCTGTGTGCACGAACCCCCCGTTCAGCCCGAC |

Figure 17 (continued)

Figure 17 (continued)

| | |
|---|---|
| ST6GAL1 | GAAGAAGCTGTACCACTCCGAAGCCTTCACAGTGAACTTTGGCGACACAGAGGAGGCCAAGAAGCA GATCAACGACTATGTGGAGAAGGGCACCCAGGGCAAGATCGTGGACCTCGTGAAGGAGCTGGATA GGGACACCGTGTTCGCTCTCGTGAACTATATCTTCTTCAAGGGCAAGTGGGAGAGGCCCTTCGAGGT GAAAGACACAGAGGAAGAGGACTTCCACGTCGACCAAGTGACCACAGTCAAGGTCCCCATGATGAA GAGACTGGGCATGTTCAACATCCAGCATTGCAAAAAGCTGAGCAGCTGGGTGCTGCTCATGAAGTA TCTCGGCAACGCCACAGCCATCTTCTTCCTGCCCGATGAGGGCAAGCTCCAGCATCTGGAAAACGAG CTCACCCACGACATTATCACCAAGTTTCTGGAGAACGAAGACAGGAGGAGCGCTAGCCTCCACCTCC CCAAACTCAGCATCACCGGCACATATGACCTGAAGTCCGTCCTCGGCCAGCTGGGCATCACAAAGGT CTTCTCCAACGGCGCCGACCTGAGCGGAGTCACAGAAGAGGCTCCCCTGAAGCTGAGCAAGGCTGT GCATAAGGCCGTGCTGACAATTGACGAGAAAGGCACAGAGGCTGCCGGAGCCATGTTCCTGGAAGC TATCCCCATGAGCATCCCCCCCGAGGTGAAATTCAACAAACCCTTCGTGTTCCTGATGATCGAGCAG AACACCAAGTCCCCCCTCTTCATGGGCAAGGTCGTGAACCCCACCCAGAAGTAAacacagtctCTGTGCC |
| BGHpA | TTCTAGTTGCCAGCCATCTGTTGTTTGCCCCTCCCCGTGCCTTCCTTGACCCTGGAAGGTGCCACTC CCACTGTCCTTTCCTAATAAAATGAGGAAATTGCATCGCATTGTCTGAGTAGGTGTCATTCTATTCTG GGGGGTGGGGTGGGGCAGGACAGCAAGGGGGAGGATTGGGAAGACAATAGCAGGCATGCTGGGG ATGCGGTGGGCTCTATGGATTAAGCTCGCGT*AGTCAATGGGAAAAACCCATTGGAGCCAAGTACACTGACT CAATAGGGACTTTCCATTGGGTTTTGCCCAGTACATAAGGTCAATAGGGGGTGAGTCAACAGGAAAGTCCCA TTGGAGCCAAGTACATTGAGTCAATAGGGGACTTTCCAATGGGTTTTGCCCAGTACATAAGGTCAATGGGAGG TAAGCCAATGGGTTTTTCCCATTACTGACATGTATACTGAGTCATTAGGGACTTTCCAATGGGTTTTGCCCAG TACATAAGGTCAATAGGGGTGAATCAACAGGAAAGTCCCATTGGAGCCAAGTACACTGAGTCAATAGGGACT TTCCATTGGGTTTTGCCCAGTACAAAAGGTCAATAGGGGGTGAGTCAATGGGTTTTTCCCATTATTGGCACAT ACATAAGGTCAATAGGGGTGACTAGTCAGTGGGCAGAGCGCACATCGCCCACAGTCCCCGAGAAGTTGGGG GGAGGGGTCGGCAATTGAACCGGTGCCTAGAGAAGGTGGCGCGGGGTAAACTGGGAAAGTGATGTCGTGT ACTGGCTCCGCCTTTTTCCCGAGGGTGGGGGAGAACCGTATATAAGTGCAGTAGTTGCCGTGAACGTTCTTT TTCGCAACGGGTTTGCCGCCAGAACACAGCTGAAGCTTCGAGGGGCTCGCATCTCTCCTTCACGCGCCCGCC GCCCTACCTGAGGCCGCCATCCACGCCGTTGAGTCGCGTTCTGCCGCCTCCCGCCTGTGGTGCCTCCTGA ACTGCGTCCGCCGTCTAGGTAAGTTTAAAGCTCAGGTCGAGACCGGGCCTTTGTCCGGCGCTCCCTTGGAGC CTACCTAGACTCAGCCGGCTCTCCACGCTTTGCCTGACCCTGCTTGCTCAACTCTACGTCTTTGTTTCGTTTTC TGTTCTGCGCCGTTACAGATCCAAGCTGTGACCGGCGCCTAC*agtgcgatCGCCACCATGATCCACACCAACCT GAAGAAGAAATTCTCCTGCTGCGTGCTGGTGTTCCTGCTGTTCGCCGTGATCTGCGTGTGGAAAGAGAAGAA GAAGGGCTCCTACTACGACTCCTTCAAGCTGCAGACCAAAGAATTCCAGGTGCTGAAGTCCCTGGGCAAGCT GGCCATGGGCTCCGACTCTCAGTCCGTGTCCTCCAGCTCTACCCAGGACCCCCACAGAGGCAGACAGACCC TGGGCTCTCTGAGAGGCCTCGGCCAAGGCTAAGCCTGAGGCCTCCTTCCAGGTGTGGAACAAGGACTCCTCC AGCAAGAACCTGATCCCCCGGCTGCAGAAGATCTGGAAGAACTACCTGTCCATGAACAAGTACAAGGTGTCC TACAAGGGCCCTGGCCCTGGCATCAAGTTCTCTGCCGAGGCCCTGAGATGCCACCTGAGGGACCATGTGAA CGTGTCCATGGTGGAAGTGACCGACTTCCCATTCAACACCTCCGAGTGGGAGGGCTACCTGCCCAAAGAGT CCATCCGGACCAAGGCTGGCCCTTGGGGCAGATGTGCTGTGGTGTCCTCTGCCGGCTCCCTGAAGTCCTCT CAGCTGGGCAGAGAGATCGACGACCACGACGCCGTGCTGCGGTTTAATGGCGCCCCTACCGCCAACTTCCA GCAGGACGTGGGCACCAAGACCACCATCCGGCTGATGAACTCCCAGCTCGTGACAACCGAGAAGCCGGTTCC TGAAGGACTCCCTGTACAAGAGGGCATCCTGATCGTGTGGGACCCCTCCGTGTACCACTCCGACATCCCCA AGTGGTATCAGAACCCCGACTACAACTTCTTCAACAACTACAAGACCTACCGGAAGCTGCACCCCAACCAGC CCTTCTACATCCTGAAGCCCCAGATGCCCTGGGAGCTGTGGGACATTCTGCAGGAAATCTCCCCGAGGAAA TCCAGCCCAACCCCCCTTCCTCTGGCATGCTGGGCATCATTATCATGATGACCCTGTGCGACCAGGTGGACA TCTACGAGTTTCTGCCCTCCAAGAGAAAGACCGACGTGTGCTACTACTACCAGAAGTTCTTCGACTCCGCCTG CACCATGGGCGCCTACCACCCTCTGCTGTACGAGAAGAACCTCGTGAAGCACCTGAACCAGGGCACCGACG AGGATATCTACCTGCTGGGCAAGGCCCACCCTGCCTGGCTTCAGAACCATCCACTGCTGA*acacagtctCTGTGC CTTCTAGTTGCCAGCCATCTGTTGTTTGCCCCTCCCCGTGCCTTCCTTGACCCTGGAAGGTGCCACT CCCACTGTCCTTTCCTAATAAAATGAGGAAATTGCATCGCATTGTCTGAGTAGGTGTCATTCTATTCT GGGGGGTGGGGTGGGGCAGGACAGCAAGGGGGAGGATTGGGAAGACAATAGCAGGCATGCTGGG GATGCGGTGGGCTCTATGG |

GLYCOSYLATION OF PROTEINS

CROSS REFERENCE TO RELATED APPLICATIONS AND INCORPORATION BY REFERENCE

This application is a U.S. national stage of International Application No. PCT/EP2018/081616, filed Nov. 16, 2018, which claims the benefit of European Patent Application No. 17204071.9, filed Nov. 28, 2017, and European Patent Application No. 18182948.2, filed Jul. 11, 2018. These applications are incorporated by reference in their entireties.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII (text) file named " 55685_SubSeqlisting.txt," 33,607 bytes, created on May 27, 2020.

FIELD OF THE INVENTION

The present invention relates to the finding of methods to shift the glycosylation profile of recombinant produced serum glycoproteins to the predominant bi-antennary form found in human plasma. This is accomplished by providing a mammalian cell line according to the invention with a series of knock outs and/or knock in's that facilitate this shift.

BACKGROUND OF THE INVENTION

Recombinant glycoproteins and in particular human serum proteins, such as the glycoproteins from the family of serpins are produced for a range of applications. This included Alpha-1-antitrypsin (AAT), Plasma protease C1 inhibitor (C1Inh), Antithrombin-III (ATIII), Monocyte neutrophil elastase inhibitor (Serpin B1), Plasminogen activator inhibitor I (PAI1) that are produced for therapeutic applications in humans.

Alpha-1-antitrypsin (AAT) is used for treatment of people with AAT-deficiency. Such deficiency may result in lethal lung disease and liver disease. Over one million people have been estimated to be deficient of AAT globally. Currently, AAT is purified from human plasma. This treatment regimen is both expensive (USD 52,000 per year per patient), and not optimal with regards to safety, as possible pathogens present in plasma may not be efficiently cleared.

Many approaches have been pursued to produce recombinant human AAT. Efforts of producing AAT in non-mammalian cells such as E. coli, yeast and plants have resulted in either non-glycosylated AAT or non-human glycosylation patterns. Production of AAT in transgenic animals such as sheep has also been reported. However, an immune response to endogenous (sheep) AAT in the purified product was later observed. This clearly demonstrates one of the major challenges that transgenic animal-derived therapeutics is facing. Finally, AAT has also been produced in CHO and human cells with an aberrant glycoprofile.

Thus, there is a need in the art for glycoproteins with a more native human glycoprofile.

OBJECT OF THE INVENTION

It is an object of embodiments of the invention to provide methods and tools for producing recombinant proteins with a glycan profile found naturally in humans.

SUMMARY OF THE INVENTION

It has been found by the present inventor(s) that by specific modification of a mammalian host cell with the downregulation or inactivation of a series of genes in combination with the insertion of other specific gene(s), this mammalian host cell is made into a cell that will produce glycoproteins with a glycosylation profile that more resemble the glycosylation profile found for the same glycoproteins naturally in humans, such as in human plasma.

So, in a first aspect the present invention relates to a recombinant mammalian cell line having a) one or more of the endogenous genes Mgat4A, Mgat4B, Mgat5, St3Gal3, St3Gal4, St3Gal6, SPPL3, and FUT8 inactivated and/or downregulated; and b) optionally a gene encoding Beta-galactoside alpha-2,6-sialyltransferase 1 inserted.

In some embodiments the endogenous gene Mgat4A is inactivated and/or downregulated.

In some embodiments the endogenous gene Mgat4B is inactivated and/or downregulated.

In some embodiments the endogenous gene Mgat5 is inactivated and/or downregulated.

In some embodiments the endogenous gene St3Gal3 is inactivated and/or downregulated.

In some embodiments the endogenous gene St3Gal4 is inactivated and/or downregulated.

In some embodiments the endogenous gene St3Gal6 is inactivated and/or downregulated.

In some embodiments the endogenous gene SPPL3 is inactivated and/or downregulated.

In some embodiments the endogenous gene B3GNT2 is inactivated and/or downregulated.

In some embodiments the endogenous gene GLUL is inactivated and/or downregulated.

In some embodiments the endogenous gene FUT8 is inactivated and/or downregulated.

In some embodiments, two, three, four, five, six, seven, or all eight of the endogenous genes Mgat4A, Mgat4B, Mgat5, St3Gal3, St3Gal4, St3Gal6, SPPL3, and FUT8 are inactivated and/or downregulated.

In some embodiments, two, three, four, five, six, seven, eight, or all nine of the endogenous genes Mgat4A, Mgat4B, Mgat5, St3Gal3, St3Gal4, St3Gal6, SPPL3, B3GNT2, and FUT8 are inactivated and/or downregulated.

In some embodiments, two, three, four, five, six, seven, eight, or all nine of the endogenous genes Mgat4A, Mgat4B, Mgat5, St3Gal3, St3Gal4, St3Gal6, SPPL3, GLUL and FUT8 are inactivated and/or downregulated.

In some embodiments, two, three, four, five, six, seven, eight, nine, or all ten of the endogenous genes Mgat4A, Mgat4B, Mgat5, St3Gal3, St3Gal4, St3Gal6, SPPL3, B3GNT2, GLUL and FUT8 are inactivated and/or downregulated.

In some embodiments two genes selected from Mgat4A and Mgat4B; Mgat4A and Mgat5; Mgat4A and St3Gal3; Mgat4A and St3Gal4; Mgat4A and St3Gal6; Mgat4A and SPPL3; Mgat4A and FUT8; GLUL and Mgat4A; GLUL and Mgat4B; GLUL and Mgat5; GLUL and St3Gal3; GLUL and St3Gal4; GLUL and St3Gal6; GLUL and SPPL3; GLUL and FUT8; Mgat4B and Mgat5; Mgat4B and St3Gal3; Mgat4B and St3Gal4; Mgat4B and St3Gal6; Mgat4B and SPPL3; Mgat4B and FUT8; Mgat5 and St3Gal3; Mgat5 and St3Gal4; Mgat5 and St3Gal6; Mgat5 and SPPL3; Mgat5 and FUT8; St3Gal3 and St3Gal4; St3Gal3 and St3Gal6;
St3Gal3 and SPPL3; St3Gal3 and FUT8; St3Gal4 and St3Gal6; St3Gal4 and SPPL3; St3Gal4 and FUT8; St3Gal6 and SPPL3; St3Gal6 and FUT8; and SPPL3 and FUT8 are inactivated and/or downregulated.

In some embodiments three genes selected from Mgat4A, Mgat4B, and Mgat5; Mgat4A, Mgat4B, and St3Gal3;
Mgat4A, Mgat4B, and St3Gal4; Mgat4A, Mgat4B, and St3Gal6;
Mgat4A, Mgat4B, and SPPL3; Mgat4A, Mgat4B, and FUT8; Mgat4A, Mgat5, and St3Gal3;
Mgat4A, Mgat5, and St3Gal4; Mgat4A, Mgat5, and St3Gal6;
Mgat4A, Mgat5, and SPPL3; Mgat4A, Mgat5, and FUT8; Mgat4A, St3Gal3, and St3Gal4;
Mgat4A, St3Gal3, and St3Gal6; Mgat4A, St3Gal3, and SPPL3; Mgat4A, St3Gal3, and FUT8;
Mgat4A, St3Gal4, and St3Gal6; Mgat4A, St3Gal4, and SPPL3; Mgat4A, St3Gal4, and FUT8;
Mgat4A, St3Gal6, and SPPL3; Mgat4A, St3Gal6, and FUT8; Mgat4A, SPPL3, and FUT8; GLUL, Mgat4B, and Mgat5; GLUL, Mgat4B, and St3Gal3; GLUL, Mgat4B, and St3Gal4; GLUL, Mgat4B, and St3Gal6; GLUL, Mgat4B, and SPPL3; GLUL, Mgat4B, and FUT8; GLUL, Mgat5, and St3Gal3; GLUL, Mgat5, and St3Gal4; GLUL, Mgat5, and St3Gal6; GLUL, Mgat5, and SPPL3; GLUL, Mgat5, and FUT8; GLUL, St3Gal3, and St3Gal4; GLUL, St3Gal3, and St3Gal6;
GLUL, St3Gal3, and SPPL3; GLUL, St3Gal3, and FUT8; GLUL, St3Gal4, and St3Gal6; GLUL, St3Gal4, and SPPL3; GLUL, St3Gal4, and FUT8; GLUL, St3Gal6, and SPPL3; GLUL, St3Gal6, and FUT8; GLUL, SPPL3, and FUT8; GLUL, Mgat4A and Mgat4B; GLUL, Mgat4A and Mgat5; GLUL, Mgat4A and St3Gal3; GLUL, Mgat4A and St3Gal4; GLUL, Mgat4A and St3Gal6; GLUL, Mgat4A and SPPL3; GLUL, Mgat4A and FUT8; Mgat4B, Mgat5, and St3Gal3; Mgat4B, Mgat5, and St3Gal4; Mgat4B, Mgat5, and St3Gal6;
Mgat4B, Mgat5, and SPPL3; Mgat4B, Mgat5, and FUT8; Mgat4B, St3Gal3, and St3Gal4;
Mgat4B, St3Gal3, and St3Gal6; Mgat4B, St3Gal3, and SPPL3; Mgat4B, St3Gal3, and FUT8;
Mgat4B, St3Gal4, and St3Gal6; Mgat4B, St3Gal4, and SPPL3; Mgat4B, St3Gal4, and FUT8;
Mgat4B, St3Gal6, and SPPL3; Mgat4B, St3Gal6, and FUT8; Mgat4B, SPPL3, and FUT8; Mgat5,
St3Gal3, and St3Gal4; Mgat5, St3Gal3, and St3Gal6; Mgat5, St3Gal3, and SPPL3;
Mgat5, St3Gal3, and FUT8; Mgat5, St3Gal4, and St3Gal6; Mgat5, St3Gal4, and SPPL3;
Mgat5, St3Gal4, and FUT8; Mgat5, St3Gal6, and SPPL3; Mgat5, St3Gal6, and FUT8; Mgat5,
SPPL3, and FUT8; St3Gal3, St3Gal4, and St3Gal6; St3Gal3, St3Gal4, and SPPL3;
St3Gal3, St3Gal4, and FUT8; St3Gal3, St3Gal6, and SPPL3; St3Gal3, St3Gal6, and FUT8;
St3Gal3, SPPL3, and FUT8; St3Gal4, St3Gal6, and SPPL3;
St3Gal4, St3Gal6, and FUT8;
St3Gal4, SPPL3, and FUT8; and St3Gal6, SPPL3, and FUT8 are inactivated and/or downregulated.

In some embodiments four genes selected from Mgat4A, Mgat4B, Mgat5, and St3Gal3;
Mgat4A, Mgat4B, Mgat5, and St3Gal4; Mgat4A, Mgat4B, Mgat5, and St3Gal6; Mgat4A, Mgat4B, Mgat5, and SPPL3; Mgat4A, Mgat4B, Mgat5, and FUT8; Mgat4A, Mgat4B, St3Gal3, and St3Gal4; Mgat4A, Mgat4B, St3Gal3, and St3Gal6; Mgat4A, Mgat4B, St3Gal3, and SPPL3; Mgat4A, Mgat4B, St3Gal3, and FUT8; Mgat4A, Mgat4B, St3Gal4, and St3Gal6, Mgat4A, Mgat4B, St3Gal4, and SPPL3;
Mgat4A, Mgat4B, St3Gal4, and FUT8; Mgat4A, Mgat4B, St3Gal6, and SPPL3; Mgat4A, Mgat4B, St3Gal6, and FUT8; Mgat4A, Mgat4B, SPPL3, and FUT8; Mgat4A, Mgat5, St3Gal3, and St3Gal4; Mgat4A, Mgat5, St3Gal3, and St3Gal6;
Mgat4A, Mgat5, St3Gal3, and SPPL3; Mgat4A, Mgat5, St3Gal3, and FUT8; Mgat4A, Mgat5, St3Gal4, and St3Gal6; Mgat4A, Mgat5, St3Gal4, and SPPL3; Mgat4A, Mgat5, St3Gal4, and FUT8; Mgat4A, Mgat5, St3Gal6, and SPPL3; Mgat4A, Mgat5, St3Gal6, FUT8; Mgat4A, Mgat5, SPPL3, and FUT8; Mgat4A, St3Gal3, St3Gal4, and St3Gal6; Mgat4A, St3Gal3, St3Gal4, and SPPL3; Mgat4A, St3Gal3, St3Gal4, and FUT8; Mgat4A, St3Gal3, St3Gal6, and SPPL3;
Mgat4A, St3Gal3, St3Gal6, and FUT8; Mgat4A, St3Gal3, SPPL3, and FUT8; Mgat4A, St3Gal4, St3Gal6, and SPPL3;
Mgat4A, St3Gal4, St3Gal6, and FUT8; Mgat4A, St3Gal4, SPPL3, and FUT8; Mgat4A, St3Gal6, SPPL3, and FUT8;
GLUL, Mgat4B, Mgat5, and St3Gal3; GLUL, Mgat4B, Mgat5, and St3Gal4; GLUL, Mgat4B, Mgat5, and St3Gal6;
GLUL, Mgat4B, Mgat5, and SPPL3; GLUL, Mgat4B, Mgat5, and FUT8; GLUL, Mgat4B, St3Gal3, and St3Gal4;
GLUL, Mgat4B, St3Gal3, and St3Gal6; GLUL, Mgat4B, St3Gal3, and SPPL3; GLUL, Mgat4B, St3Gal3, and FUT8;
GLUL, Mgat4B, St3Gal4, and St3Gal6, GLUL, Mgat4B, St3Gal4, and SPPL3; GLUL, Mgat4B, St3Gal4, and FUT8;
GLUL, Mgat4B, St3Gal6, and SPPL3; GLUL, Mgat4B, St3Gal6, and FUT8; GLUL, Mgat4B, SPPL3, and FUT8;
GLUL, Mgat5, St3Gal3, and St3Gal4; GLUL, Mgat5, St3Gal3, and St3Gal6; GLUL, Mgat5, St3Gal3, and SPPL3;
GLUL, Mgat5, St3Gal3, and FUT8; GLUL, Mgat5, St3Gal4, and St3Gal6; GLUL, Mgat5, St3Gal4, and SPPL3;
GLUL, Mgat5, St3Gal4, and FUT8; GLUL, Mgat5, St3Gal6, and SPPL3; GLUL, Mgat5, St3Gal6, FUT8;
GLUL, Mgat5, SPPL3, and FUT8; GLUL, St3Gal3, St3Gal4, and St3Gal6; GLUL, St3Gal3, St3Gal4, and SPPL3; GLUL, St3Gal3, St3Gal4, and FUT8; GLUL, St3Gal3, St3Gal6, and SPPL3; GLUL, St3Gal3, St3Gal6, and FUT8; GLUL, St3Gal3, SPPL3, and FUT8; GLUL, St3Gal4, St3Gal6, and SPPL3; GLUL, St3Gal4, St3Gal6, and FUT8; GLUL, St3Gal4, SPPL3, and FUT8; GLUL, St3Gal6, SPPL3, and FUT8; GLUL, Mgat4A, Mgat4B, and Mgat5; GLUL, Mgat4A, Mgat4B, and St3Gal3;
GLUL, Mgat4A, Mgat4B, and St3Gal4; GLUL, Mgat4A, Mgat4B, and St3Gal6; GLUL, Mgat4A, Mgat4B, and SPPL3; GLUL, Mgat4A, Mgat4B, and FUT8; GLUL, Mgat4A, Mgat5, and St3Gal3;
GLUL, Mgat4A, Mgat5, and St3Gal4; GLUL, Mgat4A, Mgat5, and St3Gal6; GLUL, Mgat4A, Mgat5, and SPPL3; GLUL, Mgat4A, Mgat5, and FUT8; GLUL, Mgat4A, St3Gal3, and St3Gal4;
GLUL, Mgat4A, St3Gal3, and St3Gal6; GLUL, Mgat4A, St3Gal3, and SPPL3; GLUL, Mgat4A, St3Gal3, and FUT8; GLUL, Mgat4A, St3Gal4, and St3Gal6; GLUL, Mgat4A, St3Gal4, and SPPL3; GLUL, Mgat4A, St3Gal4, and FUT8; GLUL, Mgat4A, St3Gal6, and SPPL3; GLUL, Mgat4A, St3Gal6, and FUT8; Mgat4B, Mgat5, St3Gal3, and St3Gal4;

Mgat4B, Mgat5, St3Gal3, and St3Gal6; Mgat4B, Mgat5, St3Gal3, and SPPL3; Mgat4B, Mgat5, St3Gal3, and FUT8; Mgat4B, Mgat5, St3Gal4, and St3Gal6; Mgat4B, Mgat5, St3Gal4, and SPPL3; Mgat4B, Mgat5, St3Gal4, and FUT8; Mgat4B, Mgat5, St3Gal6, and SPPL3;

Mgat4B, Mgat5, St3Gal6, and FUT8; Mgat4B, Mgat5, SPPL3, and FUT8; Mgat4B, St3Gal3, St3Gal4, and St3Gal6; Mgat4B, St3Gal3, St3Gal4, and SPPL3; Mgat4B, St3Gal3, St3Gal4, and FUT8; Mgat4B, St3Gal3, St3Gal6, and SPPL3; Mgat4B, St3Gal3, St3Gal6, and FUT8;

Mgat4B, St3Gal3, SPPL3, and FUT8; Mgat4B, St3Gal4, St3Gal6, and SPPL3; Mgat4B, St3Gal4, St3Gal6, and FUT8; Mgat4B, St3Gal4, SPPL3, and FUT8; Mgat4B, St3Gal6, SPPL3, and FUT8; Mgat5, St3Gal3, St3Gal4, and St3Gal6; Mgat5, St3Gal3, St3Gal4, and SPPL3;

Mgat5, St3Gal3, St3Gal4, and FUT8; Mgat5, St3Gal3, St3Gal6, and SPPL3; Mgat5, St3Gal3, St3Gal6, and FUT8; Mgat5, St3Gal3, SPPL3, and FUT8; Mgat5, St3Gal4, St3Gal6, and SPPL3;

Mgat5, St3Gal4, St3Gal6, and FUT8; Mgat5, St3Gal4, SPPL3, and FUT8; Mgat5, St3Gal6, SPPL3, and FUT8; St3Gal3, St3Gal4, St3Gal6, and SPPL3; St3Gal3, St3Gal4, St3Gal6, and FUT8; St3Gal3, St3Gal4, SPPL3, and FUT8; St3Gal3, St3Gal6, SPPL3, and FUT8; and St3Gal4, St3Gal6, SPPL3, and FUT8 are inactivated and/or downregulated.

In some embodiments five genes selected from Mgat4A, Mgat4B, Mgat5, St3Gal3, and St3Gal4; Mgat4A, Mgat4B, Mgat5, St3Gal3, and St3Gal6; Mgat4A, Mgat4B, Mgat5, St3Gal3, and SPPL3; Mgat4A, Mgat4B, Mgat5, St3Gal3, and FUT8; Mgat4A, Mgat4B, Mgat5, St3Gal4, and St3Gal6; Mgat4A, Mgat4B, Mgat5, St3Gal4, and SPPL3; Mgat4A, Mgat4B, Mgat5, St3Gal4, and FUT8; Mgat4A, Mgat4B, Mgat5, St3Gal6, and SPPL3; Mgat4A, Mgat4B, Mgat5, St3Gal6, and FUT8; Mgat4A, Mgat4B, Mgat5, SPPL3, and FUT8; Mgat4A, Mgat5, St3Gal3, St3Gal4, and St3Gal6; Mgat4A, Mgat5, St3Gal3, St3Gal4, and SPPL3; Mgat4A, Mgat5, St3Gal3, St3Gal4, and FUT8; Mgat4A, Mgat5, St3Gal3, St3Gal6, and SPPL3; Mgat4A, Mgat5, St3Gal3, St3Gal6, and FUT8; Mgat4A, Mgat5, St3Gal3, SPPL3, and FUT8; Mgat4A, St3Gal3, St3Gal4, St3Gal6, and SPPL3; Mgat4A, St3Gal3, St3Gal4, St3Gal6, and FUT8; Mgat4A, St3Gal3, St3Gal4, SPPL3, and FUT8; Mgat4A, St3Gal4, St3Gal6, SPPL3, and FUT8;

GLUL, Mgat4B, Mgat5, St3Gal3, and St3Gal4; GLUL, Mgat4B, Mgat5, St3Gal3, and St3Gal6; GLUL, Mgat4B, Mgat5, St3Gal3, and SPPL3; GLUL, Mgat4B, Mgat5, St3Gal3, and FUT8; GLUL, Mgat4B, Mgat5, St3Gal4, and St3Gal6; GLUL, Mgat4B, Mgat5, St3Gal4, and SPPL3; GLUL, Mgat4B, Mgat5, St3Gal4, and FUT8; GLUL, Mgat4B, Mgat5, St3Gal6, and SPPL3; GLUL, Mgat4B, Mgat5, St3Gal6, and FUT8; GLUL, Mgat4B, Mgat5, SPPL3, and FUT8; GLUL, Mgat5, St3Gal3, St3Gal4, and St3Gal6; GLUL, Mgat5, St3Gal3, St3Gal4, and SPPL3; GLUL, Mgat5, St3Gal3, St3Gal4, and FUT8; GLUL, Mgat5, St3Gal3, St3Gal6, and SPPL3; GLUL, Mgat5, St3Gal3, St3Gal6, and FUT8; GLUL, Mgat5, St3Gal3, SPPL3, and FUT8; GLUL, St3Gal3, St3Gal4, St3Gal6, and SPPL3; GLUL, St3Gal3, St3Gal4, St3Gal6, and FUT8; GLUL, St3Gal3, St3Gal4, SPPL3, and FUT8; GLUL, St3Gal4, St3Gal6, SPPL3, and FUT8; GLUL, Mgat4A, Mgat5, St3Gal3, and St3Gal4; GLUL, Mgat4A, Mgat5, St3Gal3, and St3Gal6; GLUL, Mgat4A, Mgat5, St3Gal3, and SPPL3; GLUL, Mgat4A, Mgat5, St3Gal3, and FUT8; GLUL, Mgat4A, Mgat5, St3Gal4, and St3Gal6; GLUL, Mgat4A, Mgat5, St3Gal4, and SPPL3; GLUL, Mgat4A, Mgat5, St3Gal4, and FUT8; GLUL, Mgat4A, Mgat5, St3Gal6, and SPPL3; GLUL, Mgat4A, Mgat5, St3Gal6, and FUT8; GLUL, Mgat4A, Mgat5, SPPL3, and FUT8; GLUL, Mgat4A, St3Gal3, St3Gal4, and St3Gal6; GLUL, Mgat4A, St3Gal3, St3Gal4, and SPPL3; GLUL, Mgat4A, St3Gal3, St3Gal4, and FUT8; GLUL, Mgat4A, St3Gal3, St3Gal6, and SPPL3; GLUL, Mgat4A, St3Gal3, St3Gal6, and FUT8; GLUL, Mgat4A, St3Gal3, SPPL3, and FUT8; GLUL, Mgat4A, St3Gal4, St3Gal6, and SPPL3; GLUL, Mgat4A, St3Gal4, St3Gal6, and FUT8; GLUL, Mgat4A, St3Gal4, SPPL3, and FUT8; and GLUL, Mgat4A, St3Gal6, SPPL3, and FUT8; Mgat4B, Mgat5, St3Gal3, St3Gal4, and St3Gal6;

Mgat4B, Mgat5, St3Gal3, St3Gal4, and SPPL3; Mgat4B, Mgat5, St3Gal3, St3Gal4, and FUT8;

Mgat4B, Mgat5, St3Gal3, St3Gal6, and SPPL3; Mgat4B, Mgat5, St3Gal3, St3Gal6, and FUT8;

Mgat4B, Mgat5, St3Gal3, SPPL3, and FUT8; Mgat4B, St3Gal3, St3Gal4, St3Gal6, and SPPL3;

Mgat4B, St3Gal3, St3Gal4, St3Gal6, and FUT8; Mgat4B, St3Gal3, St3Gal4, SPPL3, and FUT8;

Mgat4B, St3Gal4, St3Gal6, SPPL3, and FUT8; Mgat5, St3Gal3, St3Gal4, St3Gal6, and SPPL3;

Mgat5, St3Gal3, St3Gal4, St3Gal6, and FUT8; Mgat5, St3Gal3, St3Gal4, SPPL3, and FUT8;

Mgat5, St3Gal4, St3Gal6, SPPL3, and FUT8; and St3Gal3, St3Gal4, St3Gal6, SPPL3, and FUT8 are inactivated and/or downregulated.

In some embodiments six genes selected from Mgat5, St3Gal3, St3Gal4, St3Gal6, SPPL3, and FUT8; Mgat4B, St3Gal3, St3Gal4, St3Gal6, SPPL3, and FUT8; Mgat4B, Mgat5, St3Gal4, St3Gal6, SPPL3, and FUT8; Mgat4B, Mgat5, St3Gal3, St3Gal6, SPPL3, and FUT8; Mgat4B, Mgat5, St3Gal3, St3Gal4, SPPL3, and FUT8; Mgat4B, Mgat5, St3Gal3, St3Gal4, St3Gal6, FUT8; Mgat4B, Mgat5, St3Gal3, St3Gal4, St3Gal6, SPPL3; Mgat4A, St3Gal3, St3Gal4, St3Gal6, SPPL3, and FUT8; Mgat4A, Mgat5, St3Gal4, St3Gal6, SPPL3, and FUT8; Mgat4A, Mgat5, St3Gal3, St3Gal6, SPPL3, and FUT8; Mgat4A, Mgat5, St3Gal3, St3Gal4, SPPL3, and FUT8; Mgat4A, Mgat5, St3Gal3, St3Gal4, St3Gal6, and FUT8; Mgat4A, Mgat5, St3Gal3, St3Gal4, St3Gal6, and SPPL3; Mgat4A, Mgat4B, St3Gal4, St3Gal6, SPPL3, and FUT8;

Mgat4A, Mgat4B, St3Gal3, St3Gal6, SPPL3, and FUT8; Mgat4A, Mgat4B, St3Gal3, St3Gal4, SPPL3, and FUT8; Mgat4A, Mgat4B, St3Gal3, St3Gal4, St3Gal6, and FUT8; Mgat4A, Mgat4B, St3Gal3, St3Gal4, St3Gal6, and SPPL3; Mgat4A, Mgat4B, Mgat5, St3Gal6, SPPL3, and FUT8; Mgat4A, Mgat4B, Mgat5, St3Gal4, SPPL3, and FUT8; Mgat4A, Mgat4B, Mgat5, St3Gal4, St3Gal6, and FUT8; Mgat4A, Mgat4B, Mgat5, St3Gal4, St3Gal6, and SPPL3; Mgat4A, Mgat4B, Mgat5, St3Gal3, SPPL3, and FUT8; Mgat4A, Mgat4B, Mgat5, St3Gal3, St3Gal6, and FUT8; Mgat4A, Mgat4B, Mgat5, St3Gal3, St3Gal6, and SPPL3; Mgat4A, Mgat4B, Mgat5, St3Gal3, St3Gal4, and FUT8; Mgat4A, Mgat4B, Mgat5, St3Gal3, St3Gal4, and SPPL3; and Mgat4A, Mgat4B, Mgat5, St3Gal3, St3Gal4, and St3Gal6; GLUL, St3Gal3, St3Gal4, St3Gal6, SPPL3, and FUT8; GLUL, Mgat5, St3Gal4, St3Gal6, SPPL3, and FUT8; GLUL, Mgat5, St3Gal3, St3Gal6, SPPL3, and FUT8; GLUL, Mgat5, St3Gal3, St3Gal4, SPPL3, and FUT8; GLUL, Mgat5, St3Gal3, St3Gal4, St3Gal6, and FUT8; GLUL, Mgat5, St3Gal3, St3Gal4, St3Gal6, and SPPL3;

GLUL, Mgat4B, St3Gal4, St3Gal6, SPPL3, and FUT8; GLUL, Mgat4B, St3Gal3, St3Gal6, SPPL3, and FUT8; GLUL, Mgat4B, St3Gal3, St3Gal4, SPPL3, and FUT8; GLUL, Mgat4B, St3Gal3, St3Gal4, St3Gal6, and FUT8; GLUL, Mgat4B, St3Gal3, St3Gal4, St3Gal6, and SPPL3;

GLUL, Mgat4B, Mgat5, St3Gal6, SPPL3, and FUT8;
GLUL, Mgat4B, Mgat5, St3Gal4, SPPL3, and FUT8;
GLUL, Mgat4B, Mgat5, St3Gal4, St3Gal6, and FUT8;
GLUL, Mgat4B, Mgat5, St3Gal4, St3Gal6, and SPPL3;
GLUL, Mgat4B, Mgat5, St3Gal3, SPPL3, and FUT8;
GLUL, Mgat4B, Mgat5, St3Gal3, St3Gal6, and FUT8;
GLUL, Mgat4B, Mgat5, St3Gal3, St3Gal6, and SPPL3;
GLUL, Mgat4B, Mgat5, St3Gal3, St3Gal4, and FUT8;
GLUL, Mgat4B, Mgat5, St3Gal3, St3Gal4, and SPPL3; and
GLUL, Mgat4B, Mgat5, St3Gal3, St3Gal4, and St3Gal6;
GLUL, Mgat4A, Mgat4B, Mgat5, St3Gal3, and St3Gal4;
GLUL, Mgat4A, Mgat4B, Mgat5, St3Gal3, and St3Gal6;
GLUL, Mgat4A, Mgat4B, Mgat5, St3Gal3, and SPPL3;
GLUL, Mgat4A, Mgat4B, Mgat5, St3Gal3, and FUT8;
GLUL, Mgat4A, Mgat4B, Mgat5, St3Gal4, and St3Gal6;
GLUL, Mgat4A, Mgat4B, Mgat5, St3Gal4, and SPPL3;
GLUL, Mgat4A, Mgat4B, Mgat5, St3Gal4, and FUT8;
GLUL, Mgat4A, Mgat4B, Mgat5, St3Gal6, and SPPL3;
GLUL, Mgat4A, Mgat4B, Mgat5, St3Gal6, and FUT8;
GLUL, Mgat4A, Mgat4B, Mgat5, SPPL3, and FUT8;
GLUL, Mgat4A, Mgat4B, St3Gal3, St3Gal4, and St3Gal6;
GLUL, Mgat4A, Mgat4B, St3Gal3, St3Gal4, and SPPL3;
GLUL, Mgat4A, Mgat4B, St3Gal3, St3Gal4, and FUT8;
GLUL, Mgat4A, Mgat4B, St3Gal3, St3Gal6, and SPPL3;
GLUL, Mgat4A, Mgat4B, St3Gal3, St3Gal6, and FUT8;
GLUL, Mgat4A, Mgat4B, St3Gal3, SPPL3, and FUT8;
GLUL, Mgat4A, Mgat4B, St3Gal4, St3Gal6, and SPPL3;
GLUL, Mgat4A, Mgat4B, St3Gal4, St3Gal6, and FUT8;
GLUL, Mgat4A, Mgat4B, St3Gal4, SPPL3, and FUT8;
GLUL, Mgat4A, Mgat4B, St3Gal6, SPPL3, and FUT8;
GLUL, Mgat4A, Mgat4B, St3Gal6, SPPL3, and FUT8;
GLUL, Mgat4A, Mgat5, St3Gal3, St3Gal4, and St3Gal6;
GLUL, Mgat4A, Mgat5, St3Gal3, St3Gal4, and SPPL3;
GLUL, Mgat4A, Mgat5, St3Gal3, St3Gal4, and FUT8;
GLUL, Mgat4A, Mgat5, St3Gal3, St3Gal6, and SPPL3;
GLUL, Mgat4A, Mgat5, St3Gal3, St3Gal6, and FUT8;
GLUL, Mgat4A, Mgat5, St3Gal3, SPPL3, and FUT8;
GLUL, Mgat4A, Mgat5, St3Gal4, St3Gal6, and SPPL3;
GLUL, Mgat4A, Mgat5, St3Gal4, St3Gal6, and FUT8;
GLUL, Mgat4A, Mgat5, St3Gal4, SPPL3, and FUT8;
GLUL, Mgat4A, Mgat5, St3Gal6, SPPL3, and FUT8;
GLUL, Mgat4A, St3Gal3, St3Gal4, St3Gal6, and SPPL3;
St3Gal3, St3Gal4, St3Gal6, and FUT8; GLUL, Mgat4A, St3Gal3, St3Gal4, SPPL3, and FUT8; St3Gal3, St3Gal6, SPPL3, and FUT8; and GLUL, Mgat4A, St3Gal4, St3Gal6, SPPL3, and FUT8 are inactivated and/or downregulated.

In some embodiments seven genes selected from Mgat4A, Mgat4B, Mgat5, St3Gal3, St3Gal4, St3Gal6, and SPPL3: Mgat4A, Mgat4B, Mgat5, St3Gal3, St3Gal4, St3Gal6, and FUT8;
Mgat4A, Mgat4B, Mgat5, St3Gal3, St3Gal4, SPPL3, and FUT8; Mgat4A, Mgat4B, Mgat5, St3Gal3, St3Gal6, SPPL3, and FUT8; Mgat4A, Mgat4B, Mgat5, St3Gal4, St3Gal6, SPPL3, and FUT8; Mgat4A, Mgat4B, Mgat5, St3Gal3, St3Gal4, St3Gal6, SPPL3, and FUT8; Mgat4A, Mgat5, St3Gal3, St3Gal4, St3Gal6, SPPL3, and FUT8; GLUL, Mgat4B, Mgat5, St3Gal3, St3Gal4, St3Gal6, and SPPL3: GLUL, Mgat4B, Mgat5, St3Gal3, St3Gal4, St3Gal6, and FUT8; GLUL, Mgat4B, Mgat5, St3Gal3, St3Gal4, SPPL3, and FUT8; GLUL, Mgat4B, Mgat5, St3Gal3, St3Gal6, SPPL3, and FUT8; GLUL, Mgat4B, Mgat5, St3Gal4, St3Gal6, SPPL3, and FUT8;
GLUL, Mgat4B, St3Gal3, St3Gal4, St3Gal6, SPPL3, and FUT8; GLUL, Mgat5, St3Gal3, St3Gal4, St3Gal6, SPPL3, and FUT8; GLUL, Mgat4A, Mgat4B, Mgat5, St3Gal3, St3Gal4, and St3Gal6; GLUL, Mgat4A, Mgat4B, Mgat5, St3Gal3, St3Gal4, and SPPL3; GLUL, Mgat4A, Mgat4B, Mgat5, St3Gal3, St3Gal4, and FUT8; GLUL, Mgat4A, Mgat4B, Mgat5, St3Gal3, St3Gal6, and SPPL3; GLUL, Mgat4A, Mgat4B, Mgat5, St3Gal3, St3Gal6, and FUT8; GLUL, Mgat4A, Mgat4B, Mgat5, St3Gal3, SPPL3, and FUT8; GLUL, Mgat4A, Mgat4B, St3Gal3, St3Gal6, and SPPL3; GLUL, Mgat4A, Mgat4B, Mgat5, St3Gal3, St3Gal6, and FUT8; GLUL, Mgat4A, Mgat4B, Mgat5, St3Gal3, SPPL3, and FUT8; GLUL, Mgat4A, Mgat4B, St3Gal3, St3Gal4, St3Gal6, and SPPL3; GLUL, Mgat4A, Mgat4B, St3Gal3, St3Gal4, St3Gal6, and FUT8; GLUL, Mgat4A, Mgat4B, Mgat5, St3Gal3, SPPL3, and FUT8; GLUL, Mgat4A, Mgat4B, St3Gal4, St3Gal6, SPPL3, and FUT8; GLUL, Mgat4A, Mgat5, St3Gal3, St3Gal4, St3Gal6, and SPPL3; GLUL, Mgat4A, Mgat5, St3Gal3, St3Gal4, St3Gal6, and FUT8; GLUL, Mgat4A, Mgat5, St3Gal3, St3Gal4, SPPL3, and FUT8; GLUL, Mgat4A, Mgat5, St3Gal4, St3Gal6, SPPL3, and FUT8; and GLUL, Mgat4A, St3Gal3, St3Gal4, St3Gal6, SPPL3, and FUT8; and Mgat4B, Mgat5, St3Gal3, St3Gal4, St3Gal6, SPPL3, and FUT8 are inactivated and/or downregulated.

In some embodiments the gene encoding Beta-galactoside alpha-2,6-sialyltransferase 1 is inserted.

In a second aspect, the present invention relates to a method for the production of a recombinant protein of interest, the method comprising the steps of: a) culturing a population of recombinant mammalian cells according to any one of claims 4-8 in a suitable cell culture medium; and b) harvesting said human protein of interest from the cell culture or cell culture medium. In some embodiments the protein of interest is produced with a glycan structure similar or identical to the glycan profile of said glycoprotein of interest found in human plasma.

In a third aspect the present invention relates to a recombinant human glycoprotein of interest produced according to the method of the invention.

LEGENDS TO THE FIGURE

FIG. 1. Illustration of glycosylation profile with a fully sialylated bi-antennary structure without core fucosylation as found e.g. in human AAT from various sources, such as plasma-purified AAT.

Figure 2:
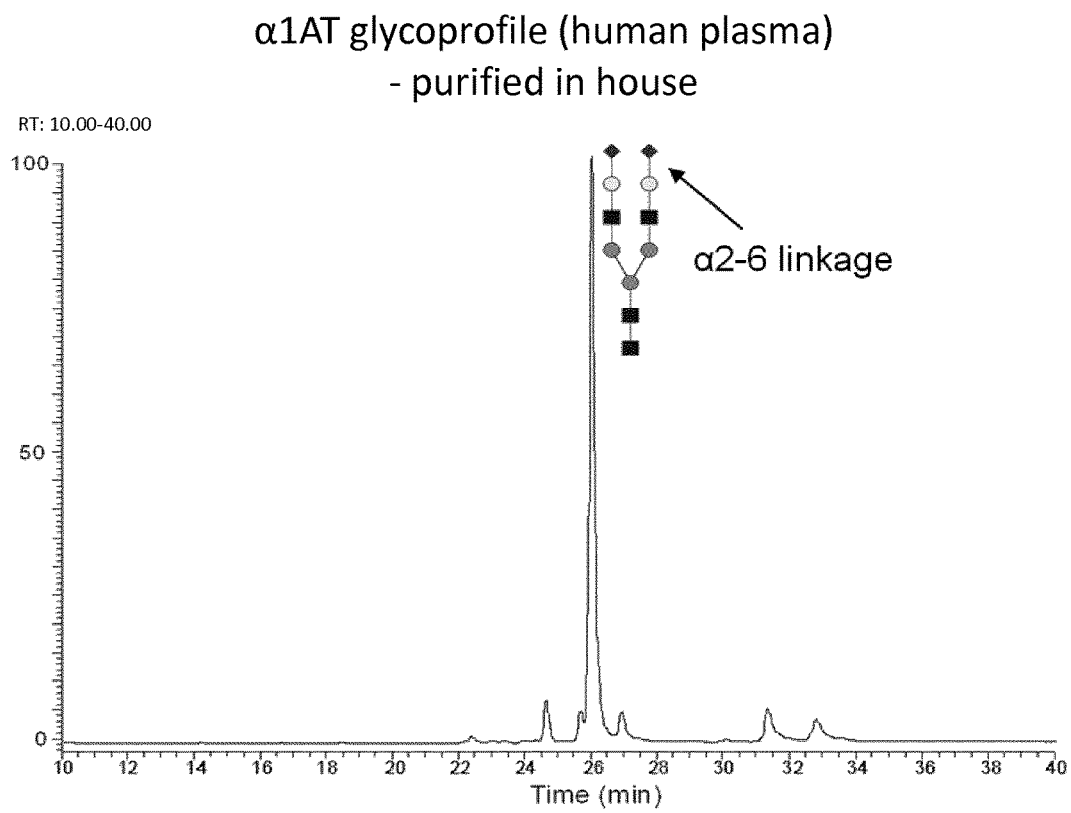
Figure 2:
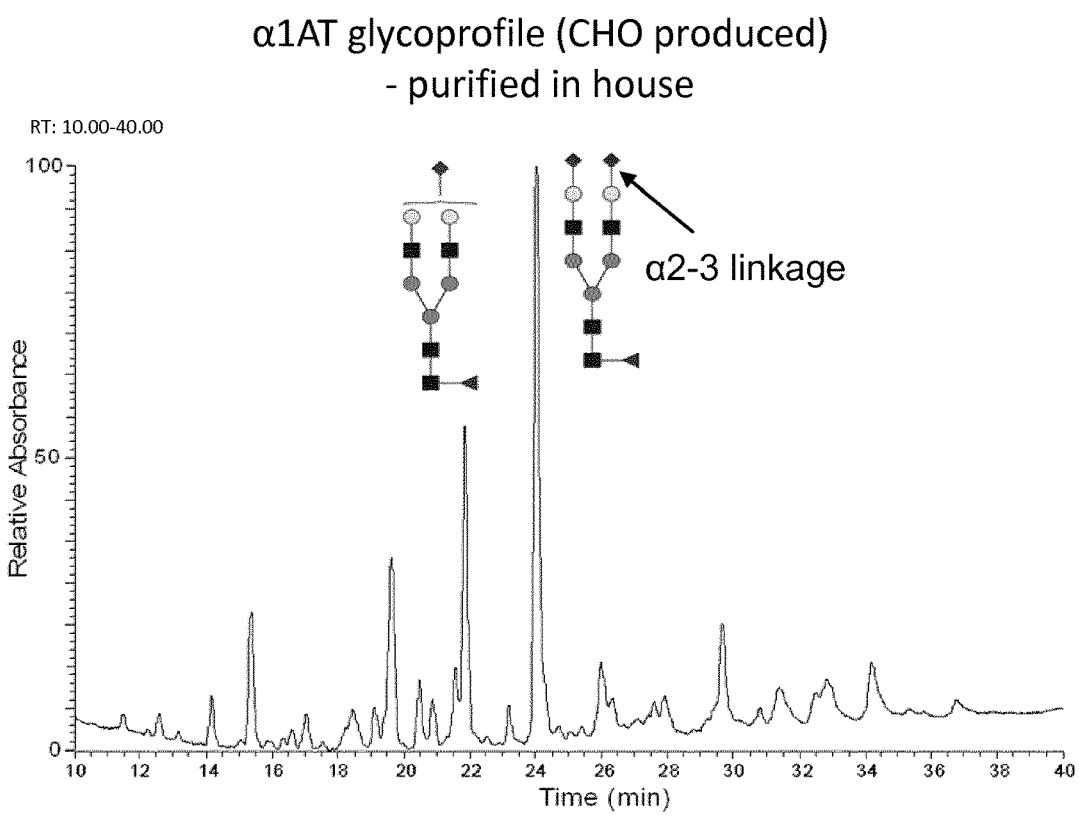

FIG. 2. Comparison of the glycoprofile of plasma-purified AAT and CHO-produced AAT. Wild-type CHO-produced AAT contains many different structures, with a core-fucosylated and partially to fully sialylated bi-antennary structure as the most dominant species, while plasma-purified contains almost exclusively a non-core-fucosylated fully sialylated bi-antennary glycostructure. In addition, CHO-derived sialic acids are linked by α2-3 linkages, while plasma sialic acids are linked by α2-6 linkages.

Figure 3:
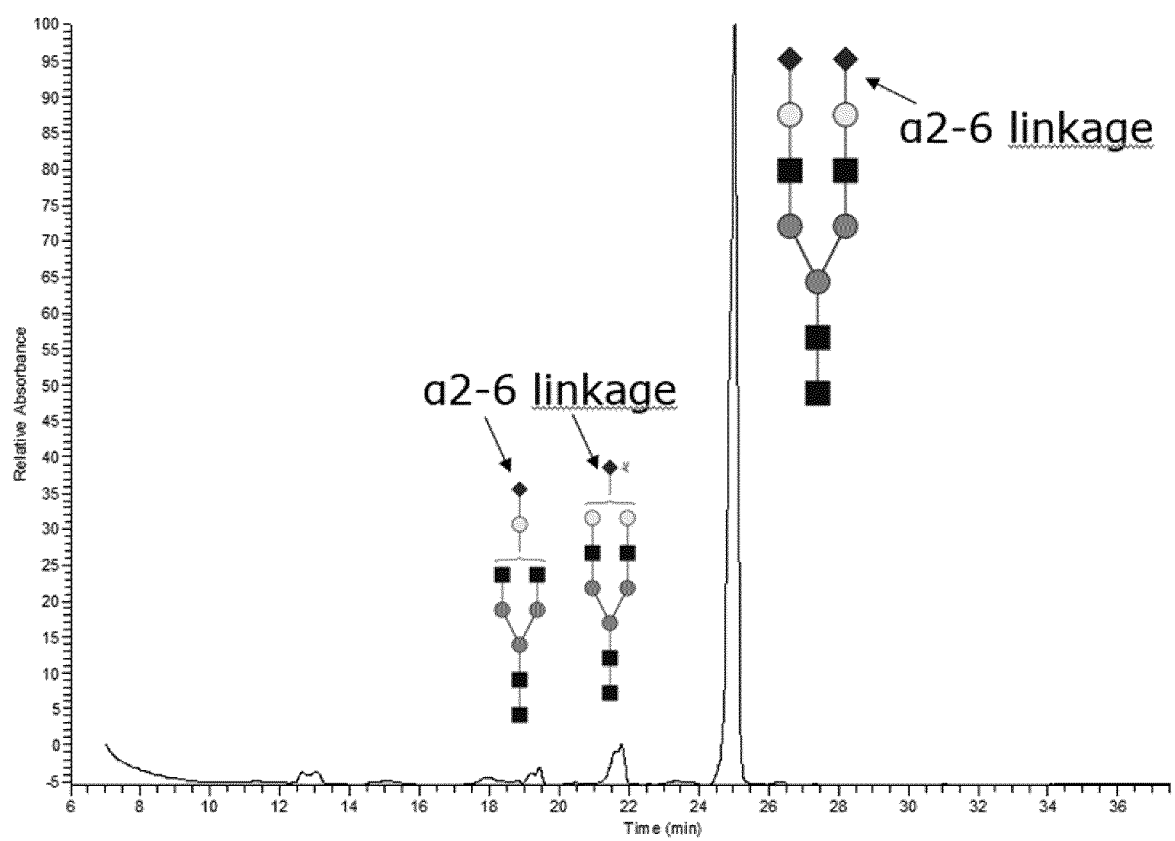

FIG. 3. Glycoprofile of human AAT derived from the engineered cell lines described here. The described gene disruptions and gene insertion results in a non-core-fucosylated fully sialylated bi-antennary glycostructure with α2-6 linked sialic acids as the predominant species.

Figure 4:
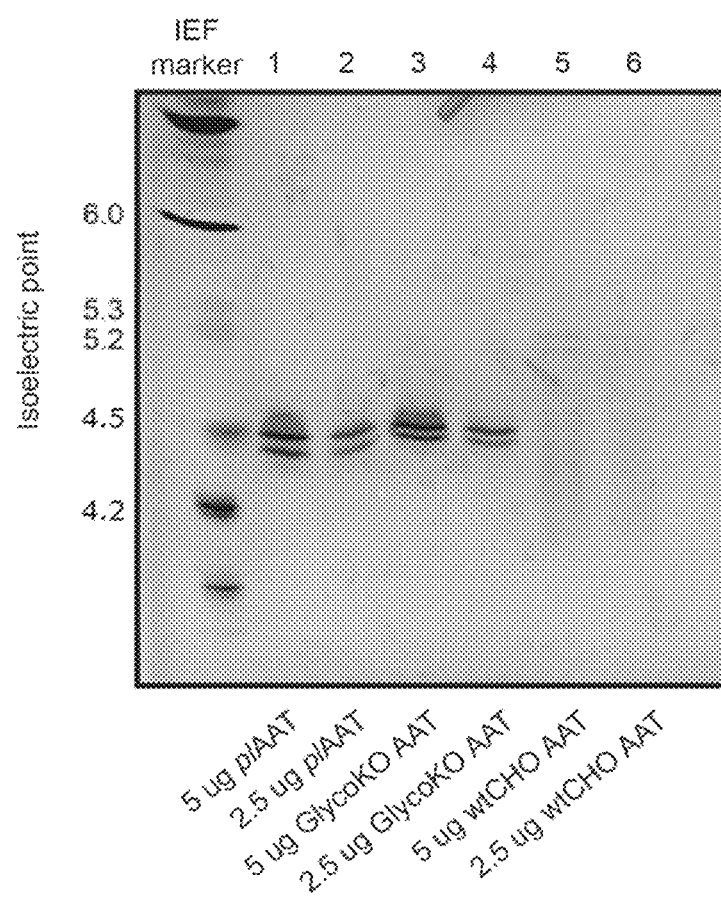

FIG. 4. Isoelectric focusing gel of AAT derived from plasma (lane 1 and 2), the glycoengineered cell lines described here (lane 3 and 4), and wild-type CHO (lane 5 and 6). Migration patterns of plasma- and glycoengineered CHO-derived are identical.

Figure 5:
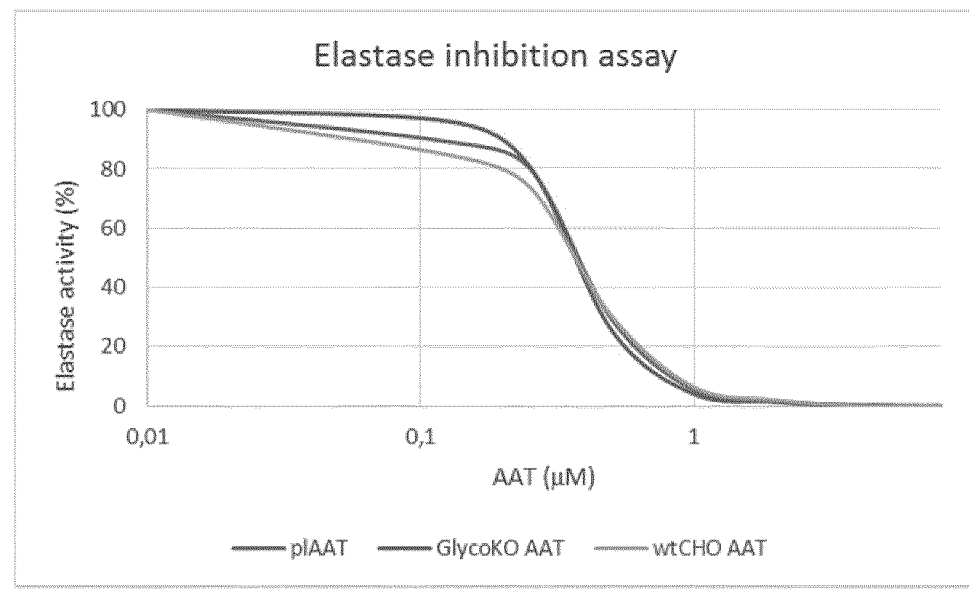

FIG. 5. Elastase inhibition assay probing the activity of
FIG. 6. St6Gal1 vector map
FIG. 7. SerpinA vector map
FIG. 8. SerpinG vector map
FIG. 9. SerpinC1 vector map
FIG. 10. Combined St6Gal1/SerpinA vector map
FIG. 11. Combined St6Gal1/SerpinG vector map FIG. 12. Growth and N-glycan structures from CHO-S WT and 10× KO cell lines. (A) Viable cell density and viability of batch cultures of CHO-S WT and two clonal cell lines with functional knockout of eight glycosyltransferases as well as GS and SPPL3. Error bars indicate the standard deviation of triplicates. (B) N-glycan analysis of total secreted proteins from CHO-S WT and the 10× KO clones A and B. Elution time is indicated on the x-axis and y-axis represents signal intensity normalized to highest peak (C) Proportion of non-fucosylated, biantennary N-glycans with terminal galactose (A2G2) in total secreted proteins from CHO-S WT and 10× KO clone A and B.

Figure 13:
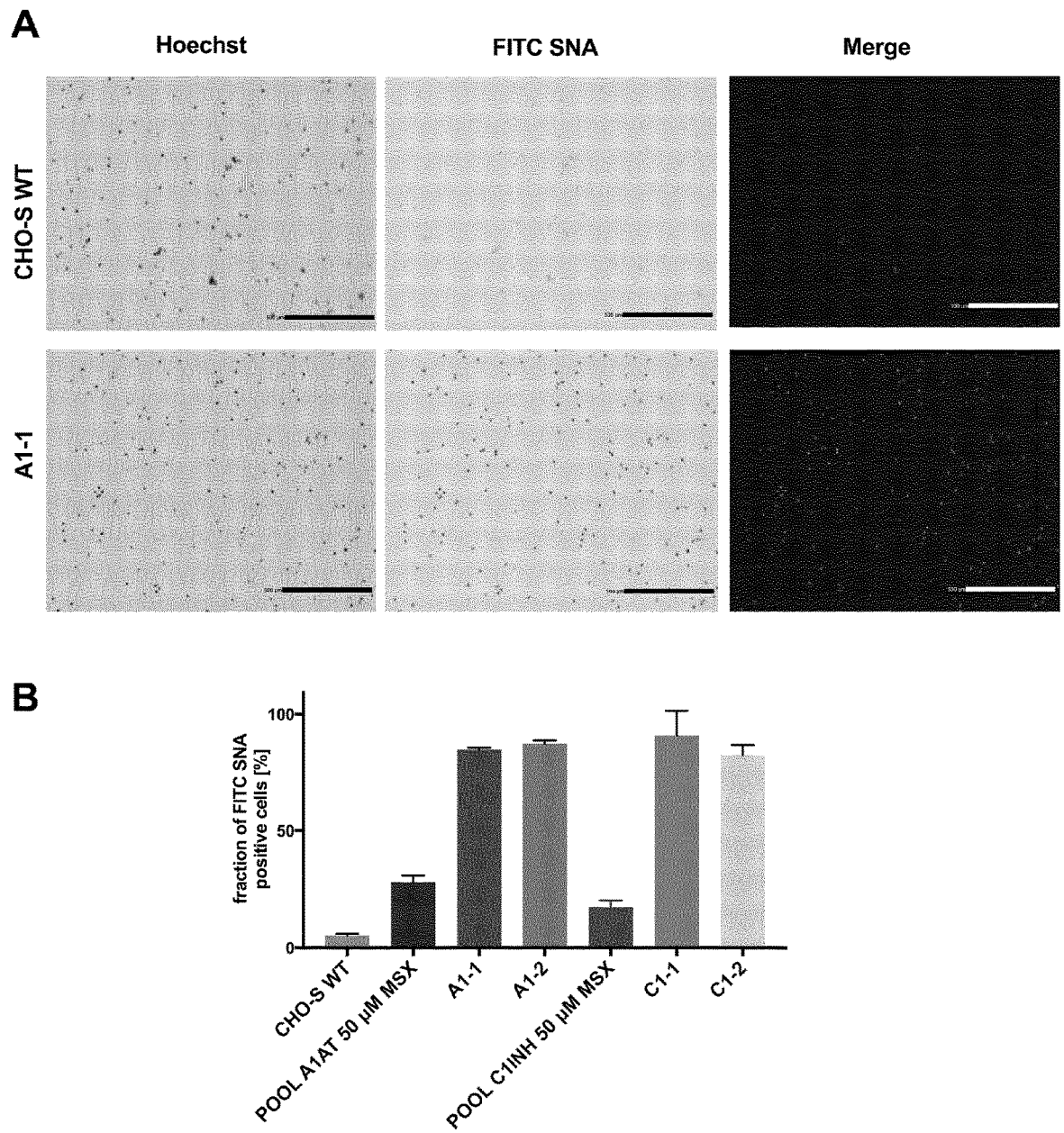

FIG. 13. FITC-SNA lectin staining of selected poly- and monoclonal cell lines. (A) Fluorescent images of CHO-S WT and A1-1 cell line. Cells were stained for alpha-2,6-sialic acid linkage with FITC-SNA (green) and for nuclei with Hoechst (blue). The bottom right corner bar displays a length of 500 µm (B) Comparison of FITC-SNA positive cells. FITC-SNA lectin staining of CHO-S WT, two 50 µM MSX polyclonal cell lines and four selected clones. Bars indicate the proportion of cells with positive FITC signal due to SNA lectin binding on alpha-2,6-linked sialic acids on the cell surface. Error bars represent standard deviation of three individual measurements per sample.

Figure 14:
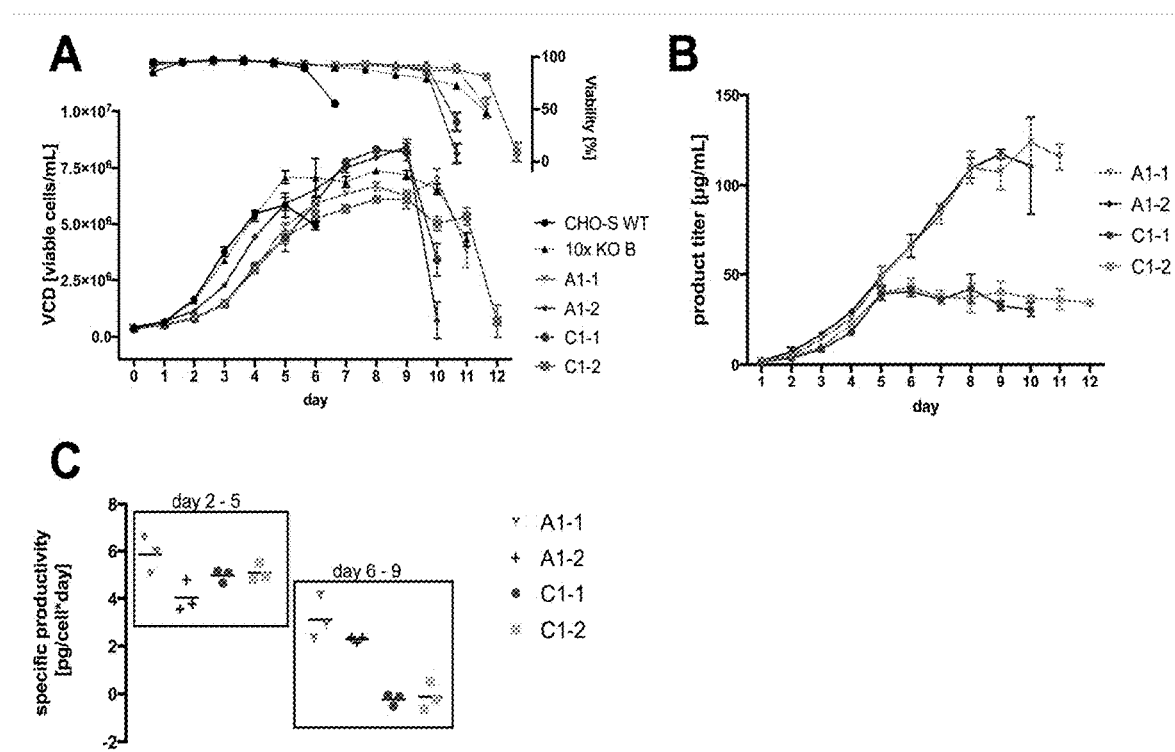

FIG. 14. Growth profiles, product titers and specific productivities of selected producing and non-producing clones. (A) Viable cell densities and cell viabilities of CHO-S WT, 10× KO B the rhA1AT- (A1-1 and A1-2) and rhC1INH- (C1-1 and C1-2) producing clonal cell lines measured in batch cultures. Error bars indicate range of duplicate parallel cultures. (B) rhA1AT and rhC1INH titer in supernatants during the batch culture experiment. Error bars indicate standard deviation of three individual measurements from two shake flasks per clone. (C) Specific productivities of the rhA1AT and rhC1INH-producing clonal cell lines in the batch culture experiment. Average specific productivity was calculated from day 2-5 and from day 6-9. Colored symbols represent average measured specific productivity for shake flask duplicates. Black lines shows the average specific productivity based on the three measurements of shake flask duplicates.

Figure 15:
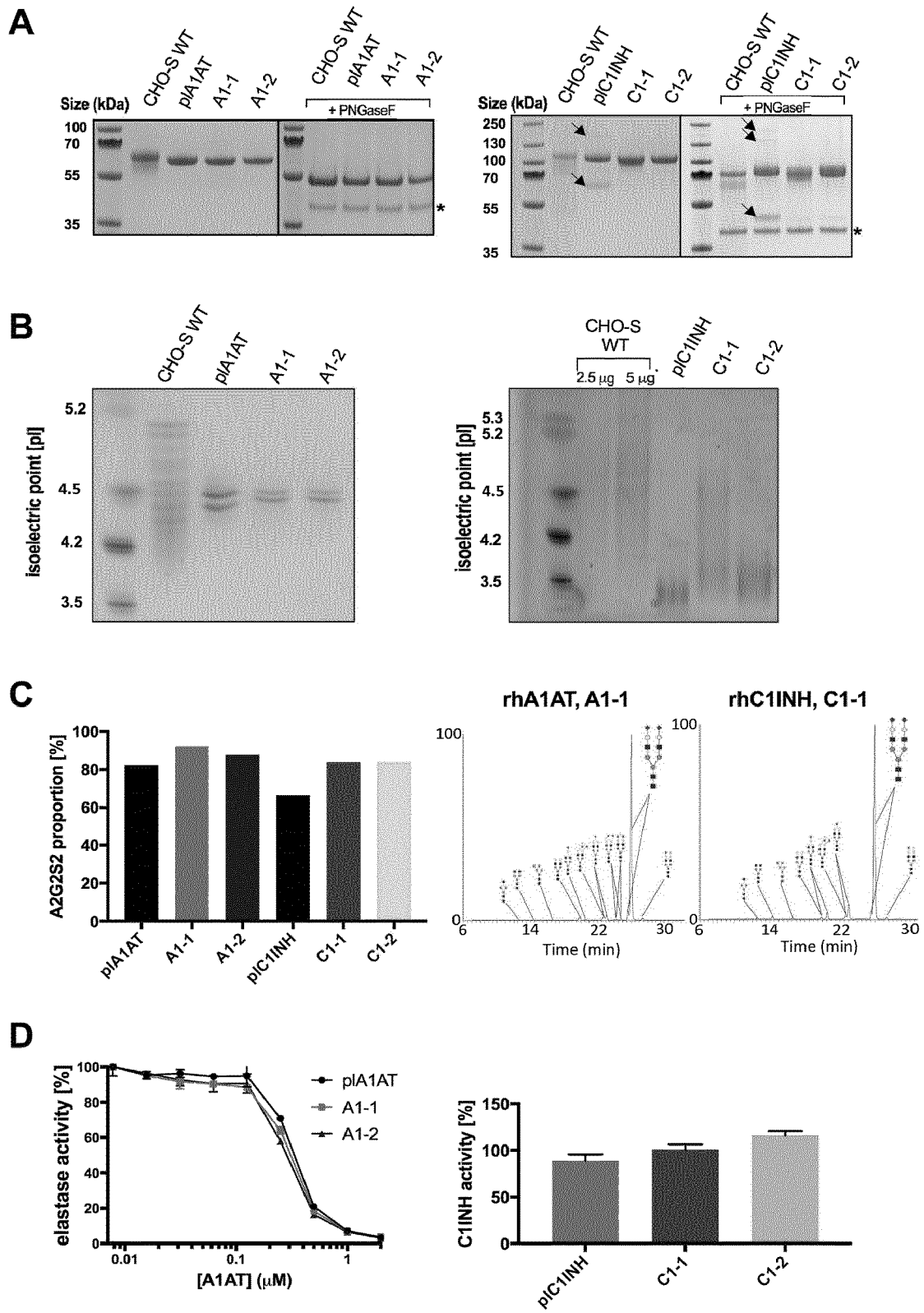

FIG. 15. Characterization of purified rhA1AT and rhC1INH. (A) SDS-PAGE gel analysis of commercially available Cinryze (pIC1INH) and Prolastin-C (plA1AT) as well as rhA1AT and rhC1INH purified from polyclonal CHO-S WT or from monoclonal cell lines derived from 10× KO B. Removal of N-glycans by PNGaseF was performed where indicated. PNGaseF migrating as a ~40 kDa band is indicated with an asterisk and impurities of pIC1INH are indicated with arrows. (B) IEF gel analysis of same proteins as described for panel A. 2.5 pg purified protein was analysed per sample if not indicated otherwise. (C) N-glycan structures annotated in clones A1-1 and C1-1, respectively, as well as A2G2S2 proportions of purified rhA1AT and rhC1INH compared to plA1AT and pIC1INH. (D) Left panel: In vitro assay measuring the inhibition of elastase activity at different concentrations of plA1AT and rhA1AT purified from clones A1-1 and A1-2. Error bars indicate range of duplicate measurements. Maximum proteolytic activity of porcine elastase was set to 100%. Right panel: In vitro activity assessment of pIC1INH and rhC1INH purified from clones C1-1 and C1-2. As described in the assay, 1 IU/ml C1INH activity was set to 100%. Error bars indicate range of duplicate measurements.

Figure 16:
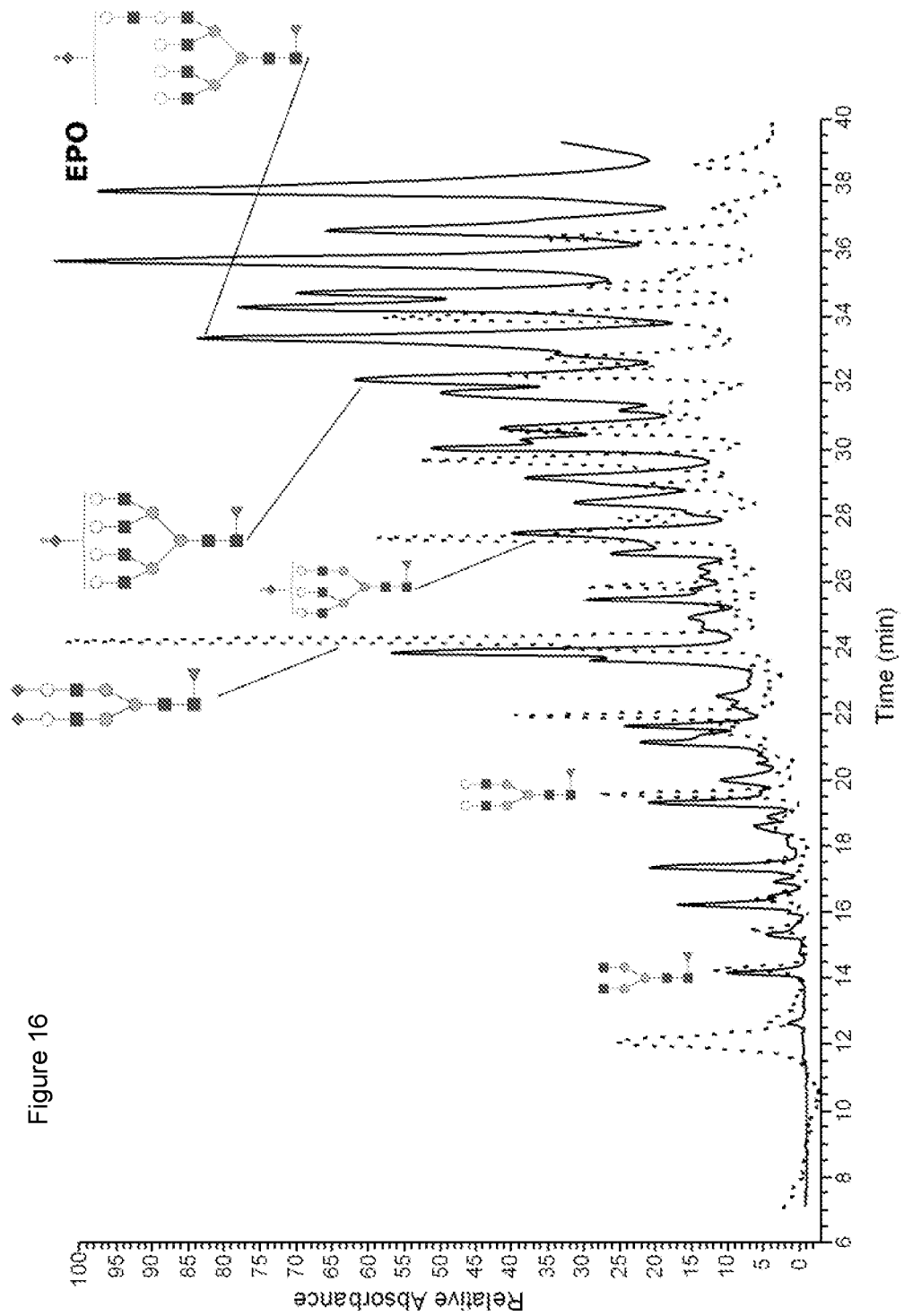
Figure 16:
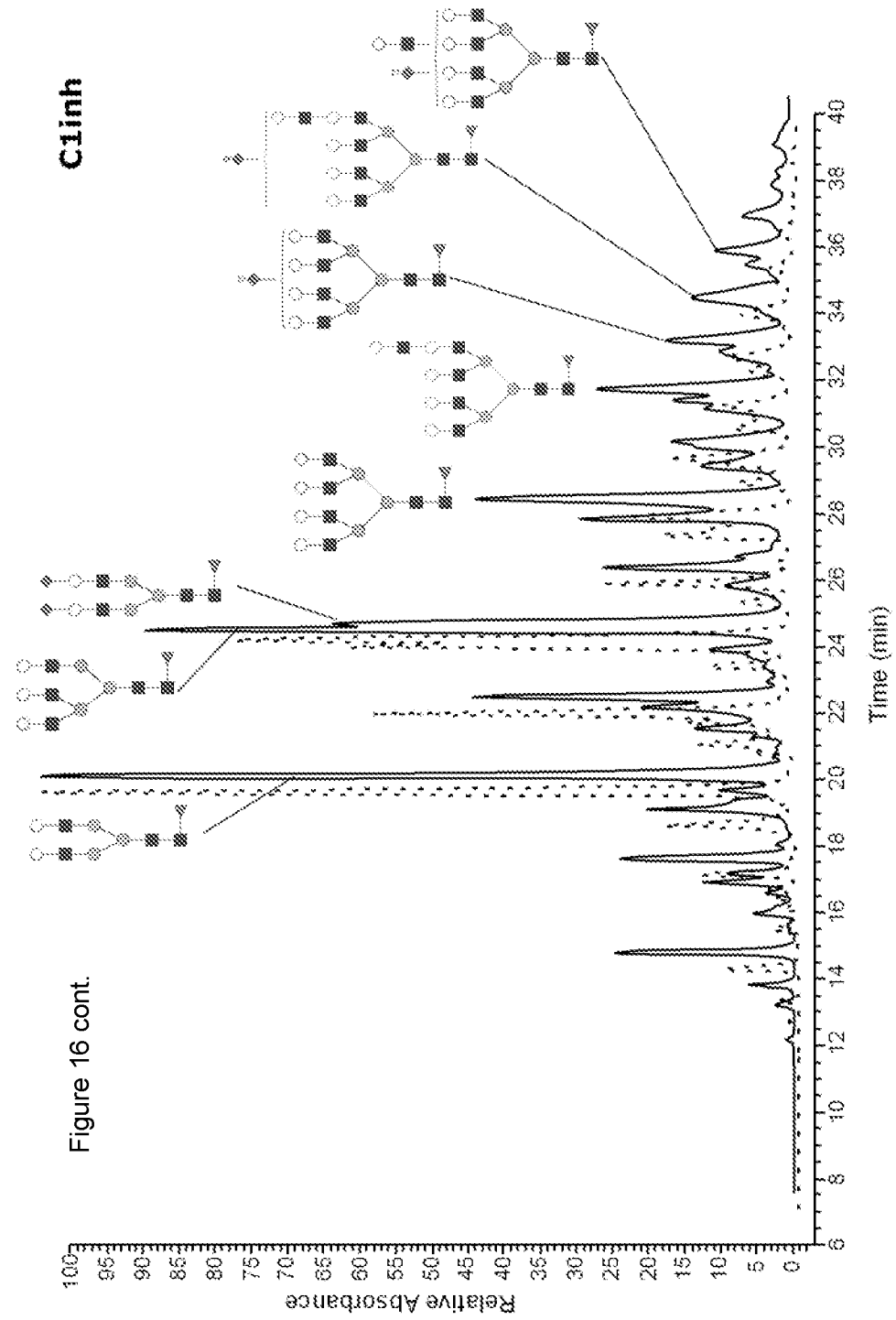

FIG. 16. N-glycan profiles, Overlay of CHO-S WT (dotted line) and Sppl3 KO (solid line) cell lines producing EPO and C1inh respectively. The effect of Sppl3 can be seen as a shift to larger N-glycans.

FIG. 17. is a Table reciting nucleotide sequences for overexpression vectors referenced in Example 4.

DETAILED DISCLOSURE OF THE INVENTION

Glyco-analysis of human AAT from various sources revealed that plasma-purified AAT is glycosylated with a fully sialylated bi-antennary structure without core fucosylation (FIGS. 1 and 2). In contrast, CHO-produced AAT contains many different structures with a partially and fully sialylated bi-antennary structure with core fucosylation as the most dominant species (FIG. 2).

The inventors of the present invention have found that a shift of the glycosylation profile of recombinant produced serum glycoproteins towards the predominant bi-antennary form found in human plasma, may be accomplished by knocking out or in any other way downregulating a selected a set of glycosylating enzymes. This will result in a 6, 7, 8, 9, 10 or 8-9 double knock out clone in which, glycoproteins, such as human serum proteins, such as human AAT are expressed. The following targets have been selected for this cell line:

1) Inactivation and/or downregulation of a series of enzymes Mgat4A, Mgat4B, and Mgat5 that that facilitate a decrease in branching.

2) Inactivation and/or downregulation of a series of enzymes St3Gal3, St3Gal4, and St3Gal6 that facilitate the removal of CHO specific alpha-2,3-sialylation.

3) Inactivation and/or downregulation of the enzyme SPPL3 that facilitate to increase glycosyltransferases half-life in the Golgi.

4) Inactivation and/or downregulation of the enzyme FUT8 that facilitate the removal of core-fucosylation.

5) An optional inactivation and/or downregulation of the enzyme B3GNT2 that may remove elongated antennas.

6) An optional inactivation and/or downregulation of the enzyme GLUL that may boost cell growth, and may be used for selection.

7) The insertion of a gene encoding Beta-galactoside alpha-2,6-sialyltransferase 1 (St6gal1), which gene direct a human type branching of sialic acids.

With these modifications, it would be accomplished to shift in the glycosylation profile to the predominant bi-antennary form found in human plasma of recombinant produced serum glycoproteins, such as human serum proteins, such as human AAT, such as in CHO cells.

A host cell with these modifications may then be modified by insertion of a gene expressing an exogenous human glycoprotein of interest, such as a therapeutic human protein, such as a human serum protein, such as Plasma protease C1 inhibitor (C1Inh), Antithrombin-III (ATIII) or Human alpha-1-antitrypsin (AAT).

In some embodiments the mammalian cells used according to the present inventions is selected from the group consisting of a Chinese Hamster Ovarian (CHO) cells, such as CHO-K1; Baby Hamster Kidney (BHK) cell; COS cell; HEK293; NS0; SP2/0; YB2/0; HUVEC; HKB; PER-C6; or derivatives of any of these cells.

In some embodiments the cell line according to the present invention is modified to express a gene expressing an exogenous human glycoprotein of interest, such as a human serum protein selected from any one human serpin of table 1:

TABLE 1

| Serpin | Alternative name(s) |
|---|---|
| SERPINA1 | Antitrypsin, Alpha-1-antitrypsin or α1-antitrypsin |
| SERPINA2 | Antitrypsin-related protein |
| SERPINA3 | Antichymotrypsin |
| SERPINA4 | Kallistatin (PI4) |
| SERPINA5 | Protein C inhibitor (PAI-3) |
| SERPINA6 | Corticosteroid-binding globulin |
| SERPINA7 | Thyroxine-binding globulin |
| SERPINA8 | Angiotensinogen |
| SERPINA9 | Centerin |
| SERPINA10 | Protein Z-dependent proteinase inhibitor |
| SERPINA11 | XP_170754.3 |
| SERPINA12 | Vaspin |
| SERPINA13 | XM_370772 |
| SERPINB1 | Monocyte neutrophil elastase inhibitor |
| SERPINB2 | Plasminogen activator inhibitor-2 (PAI2) |
| SERPINB3 | Squamous cell carcinoma antigen-1 |
| SERPINB4 | Squamous cell carcinoma antigen-2 |
| SERPINB5 | Maspin |
| SERPINB6 | Proteinase inhibitor-6 (PI6) |
| SERPINB7 | Megsin |
| SERPINB8 | Cytoplasmic antiproteinase 8 (PI8) |
| SERPINB9 | Cytoplasmic antiproteinase 9 (PI9) |
| SERPINB10 | Bomapin (PI10) |
| SERPINB11 | Epipin |
| SERPINB12 | Yukopin |
| SERPINB13 | Headpin (PI13) |
| SERPINC1 | Antithrombin |
| SERPIND1 | Heparin cofactor II |
| SERPINE1 | Plasminogen activator inhibitor I (PAI1) |
| SERPINE2 | Protease nexin I (PI7) |
| SERPINE3 | Hs.512272 |
| SERPINF1 | Pigment epithelium derived factor |
| SERPINF2 | Alpha-2-antiplasmin |
| SERPING1 | C1 inhibitor |
| SERPINH1 | 47 kDa heat-shock protein |
| SERPINI1 | Neuroserpin (PI12) |
| SERPINI2 | Myoepithelium-derived serine proteinase inhibitor (PI14) |

In particular the present inventors aimed to produce rhA1AT and rhC1INH in CHO-S with N-glycan profiles similar to plA1AT and plC1INH. First, the heterogeneous N-glycan profile of CHO-S WT cells was changed to more homogeneous profiles in bespoke cell lines with predominant A2G2 N-glycan structures. Disrupting nine N-glycosylation-related genes increased the A2G2 proportion on total secreted protein from 3.5% in CHO-S WT-derived cells to ~80% in 10× KO cell lines. This supports the strategy to decrease N-glycan branching and alpha-2,3-sialylation by disrupting MGAT4A, MGAT4B, MGAT5, ST3GAL3, ST3GAL4 and ST3GAL6. The impact of gene disruptions on cell culture performance was assessed in batch cultures. Furthermore, the monoclonal cell lines with disruption in ten gene targets showed enhanced growth characteristics compared to CHO-S WT cells. This included a boosted cell growth in the GLUL-lacking 10× KO cell lines in L-glutamine-supplemented medium.

In contrast to the production platforms previously described, rhA1AT and rhC1INH produced in the 10× KO cell lines described herein are not only exceeding sialylation levels of plA1AT and plC1INH but also reveal human-like alpha-2,6-sialylation instead of alpha-2,3-sialylation. The increased sialylation of rhA1AT had no impact on in vitro activity.

The present inventors describes a strategy to successfully engineer the heterogeneous N-glycosylation profile of in particular CHO-S WT cells towards the specific A2G2S2 N-glycan structure with the purpose of producing serpins, such as rhA1AT and rhC1INH with N-glycan profiles similar to human plasma-derived products. Thus, the present invention shows the promise and potential of replacing cost-intensive and possibly unsafe plasma-derived augmentation therapy for AATD and C1INH-HAE patients by CHO-produced rhA1AT and rhC1INH. This strategy is in compliance with the Medical and Scientific Advisory Council (MASAC) recommendation of replacing plasma-derived products with recombinant products for treatment of diseases.

Definitions

Alpha-1-antitrypsin (A1AT or AAT) refers to the protein identified as UniProtKB—P01009 (A1AT_HUMAN).

Plasma protease C1 inhibitor (C1Inh) refers to the protein identified as UniProtKB—P05155 (IC1_HUMAN)

Antithrombin-III (ATIII) refers to the protein identified as UniProtKB—P01008 (ANT3_HUMAN)

The term "inactivated and/or downregulated" refers to a modification of a mammalian host cell, wherein some specific genes are either knocked out, downregulated, or completely or partially inactivated in any other way, such as by miRNA post translational silencing. Preferably this inactivation is a complete inactivation with no measurable sign of expression of this particular gene being inactivated. Suitable techniques to silence/knockout are very well described in the art and known to the person skilled in the art, e.g. as described in WO2015092737. In one specific embodiment, "inactivated and/or downregulated" refers to a gene knock-out of the relevant gene.

The term "MGAT4A" as used herein refers to the gene encoding Mannosyl (Alpha-1,3-)-Glycoprotein Beta-1,4-N-Acetylglucosaminyltransferase, Isozyme A. This gene may also be referred to as UDP-N-Acetylglucosamine: Alpha-1,3-D-Mannoside Beta-1,4-N-Acetylglucosaminyltransferase Iva;

Mannosyl (Alpha-1,3-)-Glycoprotein Beta-1,4-N-Acetylglucosaminyltransferase, Isoenzyme A;

N-Glycosyl-Oligosaccharide-Glycoprotein N-Acetylglucosaminyltransferase Iva;

N-Acetylglucosaminyltransferase Iva;

GlcNAc-T Iva;

EC 2.4.1.145;

GNT-IVA 3;

UDP-N-Acetylglucosamine:Alpha1,3-D-Mannoside Beta1, 4-N-Acetylglucosaminyltransferase;

Alpha-1,3-Mannosyl-Glycoprotein 4-Beta-N-Acetylglucosaminyltransferase A;

Alpha-1,3-Mannosyl-Glycoprotein Beta-1,4-N-Acetylglucosaminyltransferase;

UDP-GlcNAc:A-1,3-D-Mannoside B-1,4-Acetylglucosaminyltransferase IV;

GNT-IV; and

GnT-4a.

The term "MGAT4B" as used herein refers to the gene encoding Mannosyl (Alpha-1,3-)-Glycoprotein Beta-1,4-N-Acetylglucosaminyltransferase, Isozyme B. This gene may also be referred to as UDP-N-Acetylglucosamine: Alpha-1,3-D-Mannoside Beta-1,4-N-Acetylglucosaminyltransferase IVb;

Mannosyl (Alpha-1,3-)-Glycoprotein Beta-1,4-N-Acetylglucosaminyltransferase, Isoenzyme B;

N-Glycosyl-Oligosaccharide-Glycoprotein N-Acetylglucosaminyltransferase IVb;

N-Acetylglucosaminyltransferase IVb;

GlcNAc-T IVb;

EC 2.4.1.145;

GNT-IVB 3;

UDP-N-Acetylglucosamine: Alpha-1,3-D-Mannoside Beta-1,4-N-Acetylglucosaminyltransferase IV;

Alpha-1,3-Mannosyl-Glycoprotein Beta-1,4-N-Acetylglucosaminyltransferase;
Alpha-1,3-Mannosyl-Glycoprotein 4-Beta-N-Acetylglucosaminyltransferase B;
Aminyltransferase; and
GNT-IV.

The term "MGAT5" as used herein refers to the gene encoding Mannosyl (Alpha-1,6-)-Glycoprotein Beta-1,6-N-Acetyl-Glucosaminyltransferase. This gene may also be referred to as
Alpha-Mannoside Beta-1,6-N-Acetylglucosaminyltransferase;
Mannoside Acetylglucosaminyltransferase;
N-Acetylglucosaminyl-Transferase V;
EC 2.4.1.155;
GlcNAc-T V;
GNT-V;
Alpha-1,6-Mannosylglycoprotein 6-Beta-N-Acetylglucosaminyltransferase A;
GNT-VA; and
GGNT5.

The term "ST3GAL3" as used herein refers to the gene encoding ST3 Beta-Galactoside Alpha-2,3-Sialyltransferase 3. This gene may also be referred to as ST3Gal III;
Sialyltransferase 6 (N-Acetyllacosaminide Alpha 2,3-Sialyltransferase);
Alpha 2,3-ST;
ST3GalIII;
SIAT6;
ST3N;
CMP-N-Acetylneuraminate-Beta-1,4-Galactoside Alpha-2,3-Sialyltransferase;
Gal Beta-1,3(4) GlcNAc Alpha-2,3 Sialyltransferase;
Gal Beta-1,3(4)GlcNAc Alpha-2,3 Sialyltransferase;
N-Acetyllactosaminide Alpha-2,3-Sialyltransferase;
Beta-Galactoside Alpha-2,3-Sialyltransferase;
Alpha 2,3-Sialyltransferase III;
Alpha-2,3-Sialyltransferase II;
Sialyltransferase 6;
EC 2.4.99.6;
ST3GALII;
EIEE15; and
MRT12.

The term "ST3GAL4" as used herein refers to the gene encoding ST3 Beta-Galactoside Alpha-2,3-Sialyltransferase 4. This gene may also be referred to as
Sialyltransferase 4C (Beta-Galactosidase Alpha-2,3-Sialytransferase);
Gal-Beta-1,4-GalNAc-Alpha-2,3-Sialyltransferase;
Beta-Galactoside Alpha-2,3-Sialyltransferase 4;
Alpha 2,3-Sialyltransferase IV;
Alpha 2,3-ST 4;
Gal-NAc6S;
ST3GalA.2;
ST3Gal IV;
ST3GalIV;
NANTA3;
SIAT4C;
CGS23;
ST-4;
STZ;
CMP-N-Acetylneuraminate-Beta-Galactosamide-Alpha-2,3-Sialyltransferase;
Sialyltransferase 4C (Beta-Galactoside Alpha-2,3-Sialytransferase);
Alpha-3-N-Acetylneuraminyltransferase;
Sialyltransferase 4C;
EC 2.4.99.9;
EC 2.4.99.-;
EC 2.4.99;
SIAT4-C;
SIAT4;
SAT-3; and
SAT3.

The term "ST3GAL6" as used herein refers to the gene encoding ST3 Beta-Galactoside Alpha-2,3-Sialyltransferase 6. This gene may also be referred to as CMP-NeuAc:Beta-Galactoside Alpha-2,3-Sialyltransferase VI;
Sialyltransferase 10 (Alpha-2,3-Sialyltransferase VI);
ST3GALVI;
SIAT10;
Type 2 Lactosamine Alpha-2,3-Sialyltransferase;
Alpha2,3-Sialyltransferase ST3Gal VI;
Sialyltransferase;
EC 2.4.99.9;
EC 2.4.99.-;
ST3Gal VI; and
EC 2.4.99.

The term "B3GNT2" as used herein refers to the gene encoding UDP-GlcNAc:BetaGal Beta-1,3-N-Acetylglucosaminyltransferase 2. This gene may also be referred to as UDP-GlcNAc:BetaGal Beta-1,3-N-Acetylglucosaminyltransferase;
Beta3Gn-T1;
Beta3Gn-T2;
B3GNT1;
BGnT-2;
UDP-Galactose:Beta-N-Acetylglucosamine Beta-1,3-Galactosyltransferase 7;
N-Acetyllactosaminide Beta-1,3-N-Acetylglucosaminyltransferase;
UDP-Gal:Beta-GlcNAc Beta-1,3-Galactosyltransferase 7;
Beta-1,3-N-Acetylglucosaminyltransferase BGnT-1;
Beta-1,3-N-Acetylglucosaminyltransferase BGnT-2;
Beta-1,3-N-Acetylglucosaminyltransferase 1;
Beta-1,3-N-Acetylglucosaminyltransferase 2;
Beta-1,3-Galactosyltransferase 7;
Beta-1,3-GalTase 7;
Beta-1,3-Gn-T1;
Beta-1,3-Gn-T2;
Beta-3-Gx-T7;
EC 2.4.1.149;
Beta3Gal-T7;
Beta3GalT7;
BETA3GNT;
B3Gal-T7;
3-Gn-T1;
3-Gn-T2;
B3GN-T2;
B3GNT-2;
B3GALT7;
Beta-1;
BGnT-1;
B3GNT; and
BGNT2.

The term "GLUL" as used herein refers to the gene encoding glutamate-ammonia ligase also referred to as:
Glutamate-Ammonia Ligase;
Glutamate Decarboxylase;
Glutamine Synthetase;
EC 6.3.1.2;
GLNS;
GS;

Glutamate-Ammonia Ligase (Glutamine Synthase);
Cell Proliferation-Inducing Protein 59;
Proliferation-Inducing Protein 43;
Glutamate—Ammonia Ligase;
Glutamine Synthase;
EC 4.1.1.15;
PIG43; and
PIG59.

The term "SPPL3" as used herein refers to the gene encoding Signal Peptide Peptidase Like 3.

This gene may also be referred to as
Presenilin-Like Protein 4;
Intramembrane Protease 2;
Presenilin Homologous Protein 1;
SPP-Like 3;
IMP2;
PSH1;
PSL4;
Signal Peptide Peptidase-Like 3;
EC 3.4.23-;
MDHV1887;
PRO4332; and
IMP-2.

The term "FUT8" as used herein refers to the gene encoding Fucosyltransferase 8. This gene may also be referred to as
GDP-L-Fuc:N-Acetyl-Beta-D-Glucosaminide Alpha1,6-Fucosyltransferase;
Fucosyltransferase 8 (Alpha (1,6) Fucosyltransferase);
GDP-Fucose—Glycoprotein Fucosyltransferase;
Glycoprotein 6-Alpha-L-Fucosyltransferase;
Alpha1-6FucT;
EC 2.4.1.68 4;
Alpha (1,6) Fucosyltransferase;
Alpha-(1,6)-Fucosyltransferase The term "ST6Gal1" as used herein refers to the gene encoding ST6 Beta-Galactoside Alpha-2,6-Sialyltransferase 1. This gene may also be referred to as ST6Gal I;
CMP-N-Acetylneuraminate-Beta-Galactosamide-Alpha-2,6-Sialyltransferase 1:
ST6 N-Acetylgalactosaminide Alpha-2,6-Sialyltransferase 1;
ST6 Beta-Galactosamide Alpha-2,6-Sialyltranferase 1;
B-Cell Antigen CD75;
Alpha 2,6-ST 1;
EC 2.4.99.1;
ST6GalI;
SIAT1;
CMP-N-Acetylneuraminate Beta-Galactosamide Alpha-2,6-Sialyltransferase;
Sialyltransferase 1 (Beta-Galactoside Alpha-2,6-Sialyltransferase);
Sialyltransferase 1 (Beta-Galactoside Alpha-2,6-Sialytransferase);
Beta-Galactoside Alpha-2,6-Sialyltransferase 1;
Sialyltransferase 1; and
ST6N.

Specific Embodiments of the Invention

As detailed above in a first aspect the present invention relates to a recombinant mammalian cell line having a) one or more of the endogenous genes Mgat4A, Mgat4B, Mgat5, St3Gal3, St3Gal4, St3Gal6, SPPL3, and FUT8 inactivated and/or downregulated; and b) optionally a gene encoding Beta-galactoside alpha-2,6-sialyltransferase 1 inserted.

In some embodiments of the mammalian cell according to present invention the endogenous genes Mgat4A, Mgat4B, Mgat5, St3Gal3, St3Gal4, St3Gal6, SPPL3, and FUT8 are inactivated and/or downregulated; and the gene encoding ST6Gal1 is inserted.

In some embodiments the mammalian cell according to present invention has the endogenous genes Mgat4A, Mgat4B, Mgat5, St3Gal4, St3Gal6, and FUT8 inactivated and/or downregulated.

In some embodiments the mammalian cell according to present invention has the endogenous genes Mgat4A, Mgat4B, Mgat5, St3Gal4, St3Gal6, SPPL3, and FUT8 inactivated and/or downregulated.

In some embodiments of the mammalian cell according to present invention the endogenous gene B3GNT2 is present.

In some embodiments the mammalian cell according to present invention further has the endogenous B3GNT2 is inactivated and/or downregulated. It is to be understood that this may be in addition to any combination of other genes being inactivated and/or downregulated.

In some embodiments the mammalian cell according to present invention further has the endogenous GLUL is inactivated and/or downregulated. It is to be understood that this may be in addition to any combination of other genes being inactivated and/or downregulated.

In some embodiments the mammalian cell according to present invention is an in vitro cell line, such as any one selected from the group consisting of a Chinese Hamster Ovarian (CHO) cells, such as CHO-K1, CHO-S, DG44; Baby Hamster Kidney (BHK) cell; COS cell; HEK29; NS0; SP2/0; YB2/0; HUVEC; HKB; PER-C6; NS0; or derivatives of any of these cells.

In some embodiments the mammalian cell according to present invention has been further modified to express an exogenous human glycoprotein of interest, such as a therapeutic human protein. In some embodiments said exogenous human glycoprotein of interest is a human serum protein, such as a human serpin, such as human serpin selected from the list consisting of SERPINA1, SERPINA2, SERPINA3, SERPINA4, SERPINA5, SERPINA6, SERPINA7, SERPINA8, SERPINA9, SERPINA10, SERPINA11, SERPINA12, SERPINA13, SERPINB1, SERPINB2, SERPINB3, SERPINB4, SERPINB5, SERPINB6, SERPINB7, SERPINB8, SERPINB9, SERPINB10, SERPINB11, SERPINB12, SERPINB13, SERPINC1, SERPIND1, SERPINE1, SERPINE2, SERPINE3, SERPINF1, SERPINF2, SERPING1, SERPINH1, SERPINI1, and SERPINI2.

In some embodiments the mammalian cell according to present invention is a cell line producing said glycoprotein of interest with a primary n-glycan structure that is a fully sialylated bi-antennary structure without core fucosylation, such as with more than 80%, such as 82%, such as 84%, such as 86%, such as 88%, such as 90% of the glycoproteins of interest produced being in with a fully sialylated bi-antennary structure without core fucosylation.

In some embodiments the mammalian cell according to present invention has a glycan structure according to the structure A2G2S2 with the following pictorial representations:

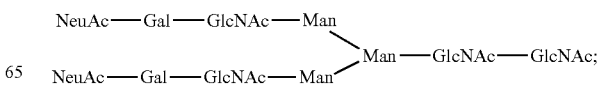

Such as according to the structure:

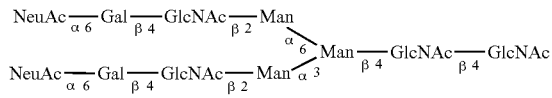

In some embodiments the mammalian cell according to present invention has been further modified to express an exogenous human glycoprotein of interest, which exogenous human glycoprotein of interest is selected from Plasma protease C1 inhibitor (C1Inh) glycosylated at one or more positions selected from Asn3, Asn47, Asn59, Asn216, Asn231, Asn250, and Asn330; Antithrombin-III (ATIII) glycosylated at one or more positions selected from Asn96, Asn135, Asn155 and Asn192; and Human alpha-1-antitrypsin (AAT) glycosylated at one or more, such as two or three of the positions Asn46, Asn83, and Asn247.

Example 1

We knocked out 9 genes in the CHO-S cell line employing CRISPR/Cas9: FUT8, MGAT4a, MGAT4b, MGAT5, ST3GAL3, ST3GAL4, ST3GAL6, B3gnt2, Sppl3. Furthermore, we introduced the human gene ST6GAL1 to introduce human type branching of sialic acids. The human genes SERPING or SERPINA were then introduced in this host cell line to achieve expression of the human serum proteins Plasma protease C1 inhibitor (C1Inh) or Human alpha-1-antitrypsin (AAT), respectively. With these modifications, it is accomplished to shift in the glycosylation profile to the predominant bi-antennary, non-core-fucosylated, and α2-6 linked sialic acid form found in human plasma of recombinant produced serum glycoproteins (FIG. 3). IEF migration patterns are identical between AAT derived from plasma and the glycoengineered cell line described here (FIG. 4). Activity of AAT is not affected (FIG. 5). Plasmids 2632 (GFP_2A_Cas9) and 5920 (FUT8_681494) are described in Gray, L. M., Lee, J. S., Gerling, S., Kallehauge, T. E., Hansen, A. H., Kol, S., Lee, G. M., Pedersen, L. E. and Kildegaard, H. F. (2015), One-step generation of triple knockout CHO cell lines using CRISPR/Cas9 and fluorescent enrichment. Biotechnology journal, 10: 1446-1456. doi:10.1002/biot.201500027.

Plasmids 2928 (MGAT4A_411545), 2933 (MGAT4B_1280368), 2937 (MGAT5_327084), 2940 (ST3GAL4_964386), 2943 (ST3GAL6_1812502), 4408 (B3gnt2_NW_003613880.1_1273293), 4412 (St3gal3_NW_003613906.1_244730) and 4424 (Sppl3_NW_003613978.1_213040) were constructed as described in Ronda, C., Pedersen, L. E., Hansen, H. G., Kallehauge, T. B. et al., Accelerating genome editing in CHO cells using CRISPR/Cas9 and CRISPy, a web-based target finding tool. *Biotechnol. Bioeng.* 2014, 111, 1604-1616 with the following modification: sgRNA plasmid sgRNA1_C described in Ronda et al was used as template in the PCR reaction to generate the backbone of gRNA plasmids.

Figure 6:
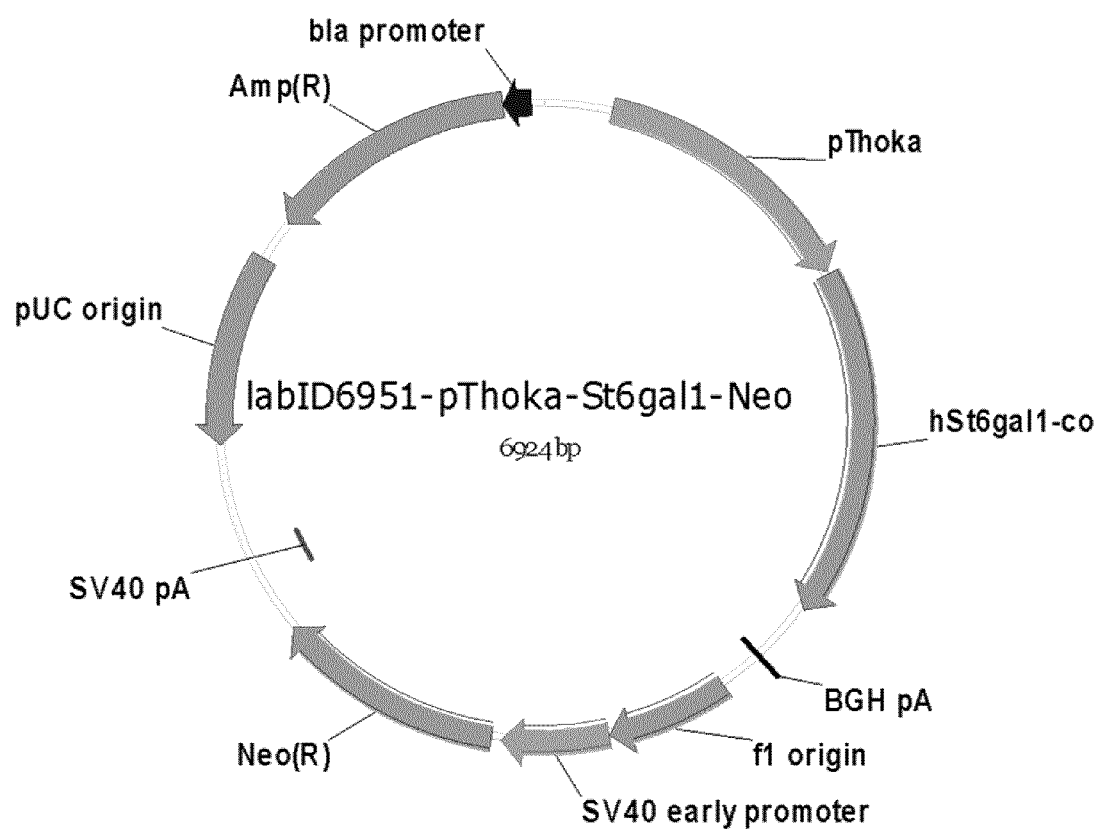
Figure 7:
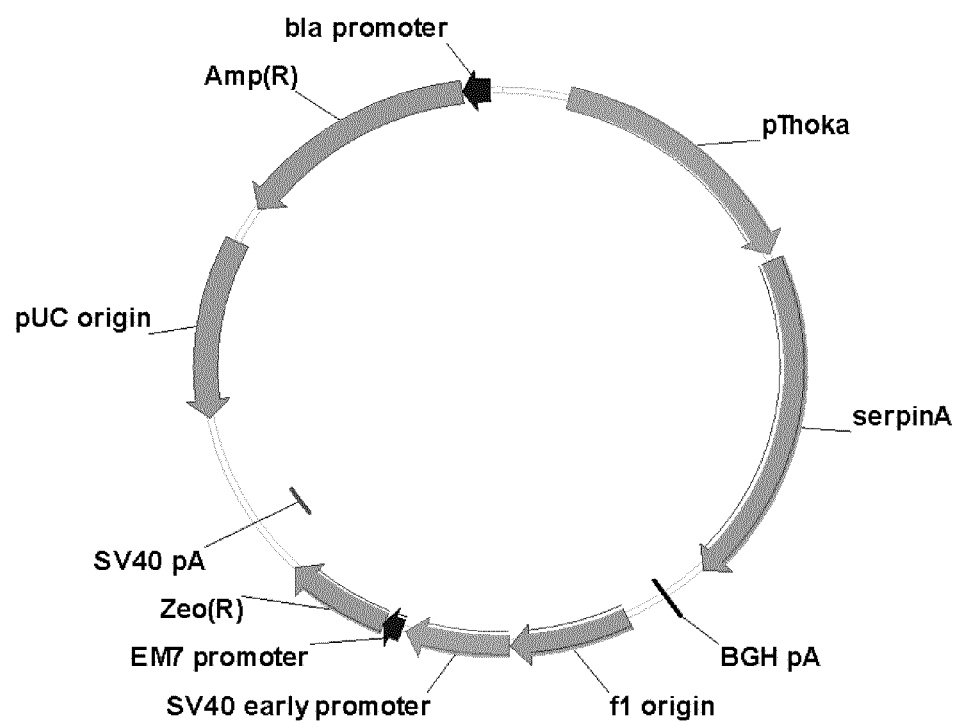
Figure 8:
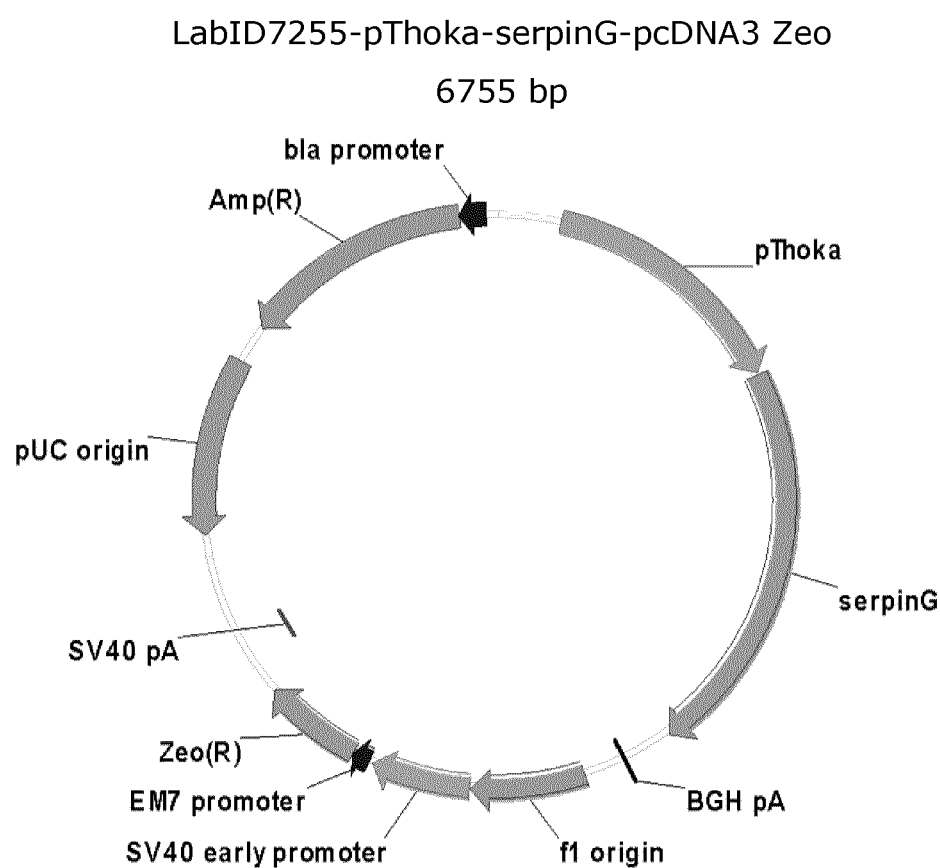
Figure 9:
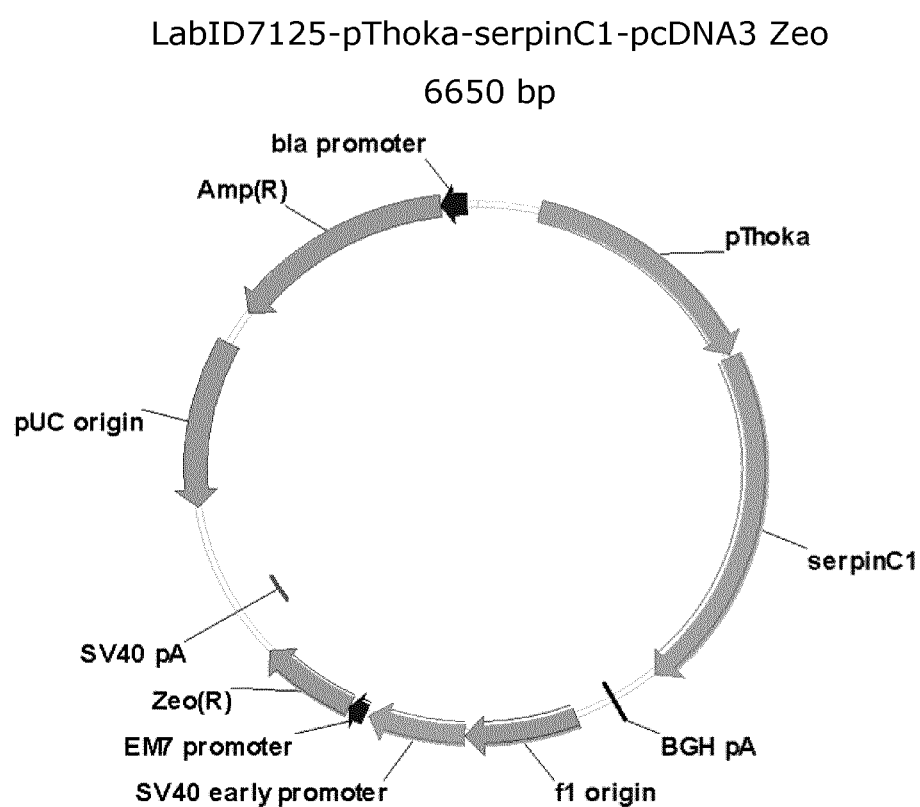

St6Gal1 vector map is shown in FIG. 6.
SerpinA vector map is shown in FIG. 7.
SerpinG vector map is shown in FIG. 8.
SerpinC1 vector map is shown in FIG. 9.

Example 2

We knocked out 10 genes in the CHO-S cell line employing CRISPR/Cas9: FUT8, MGAT4a, MGAT4b, MGAT5, ST3GAL3, ST3GAL4, ST3GAL6, B3gnt2, Sppl3 and GLUL. We have constructed plasmids harbouring both the human ST6GAL1, and SERPING or SERPINA genes to simultaneously introduce human type branching of sialic acids and achieve expression of Plasma protease C1 inhibitor (C1Inh), or Human alpha-1-antitrypsin (AAT), respectively.

Figure 10:
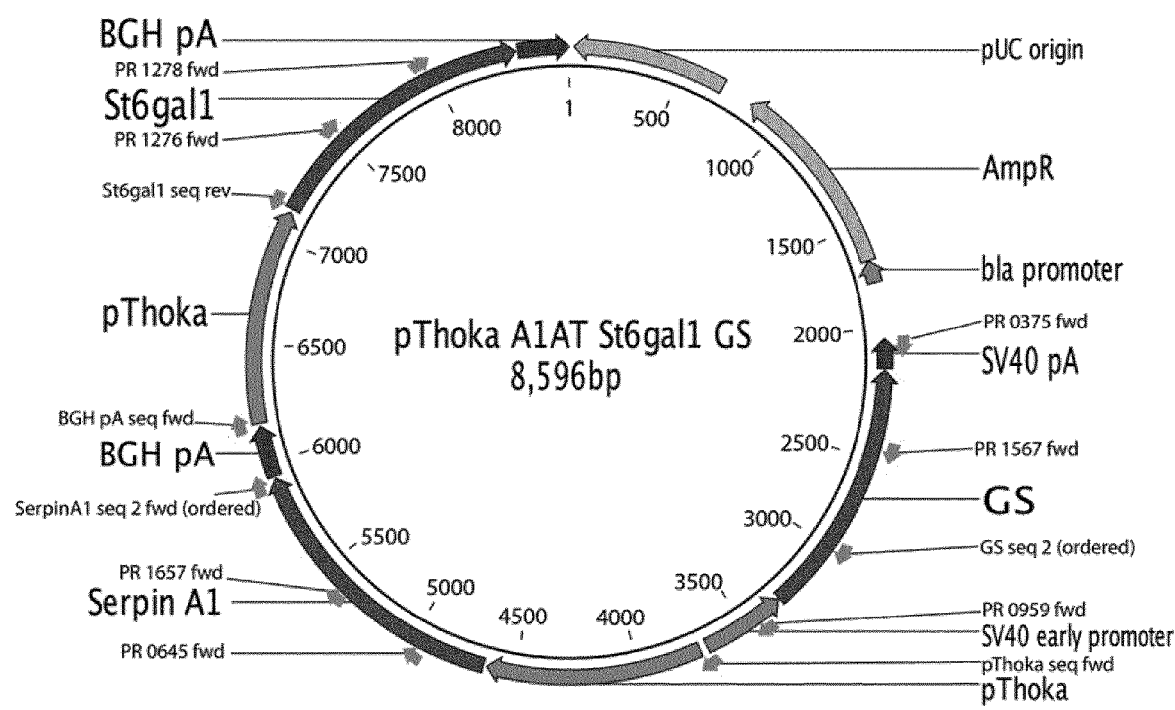

Combined St6Gal1/SerpinA vector map is shown in FIG. 10.

Figure 11:
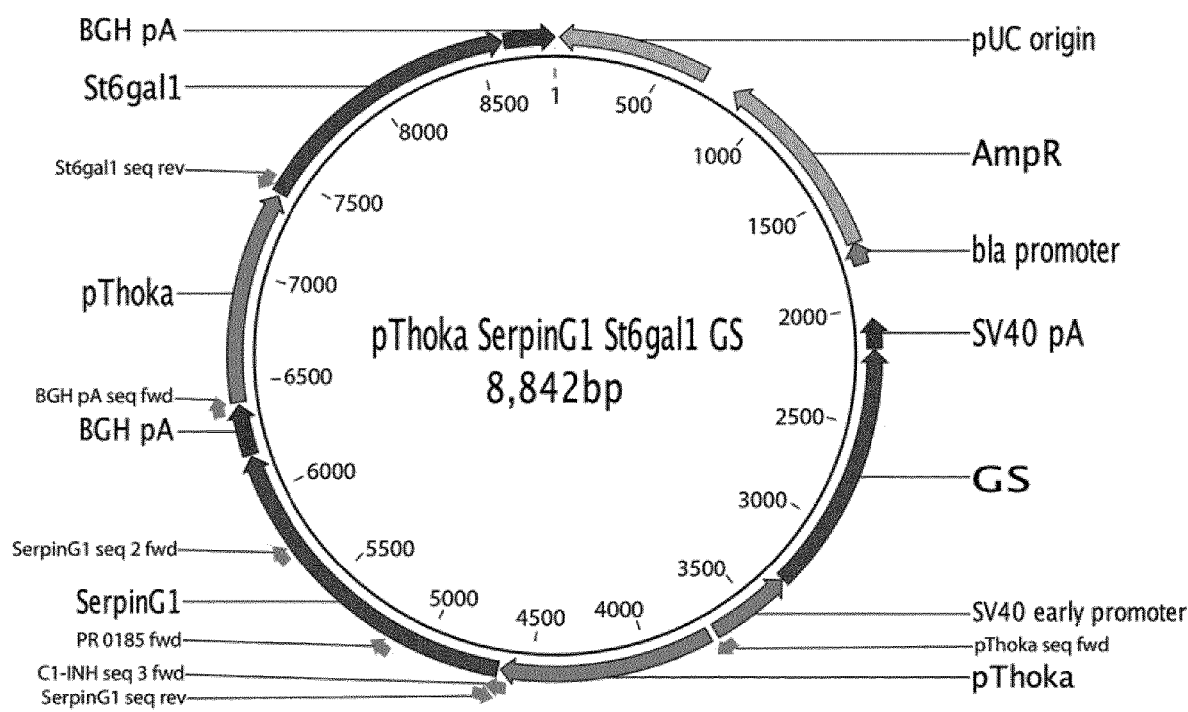
Figure 12:
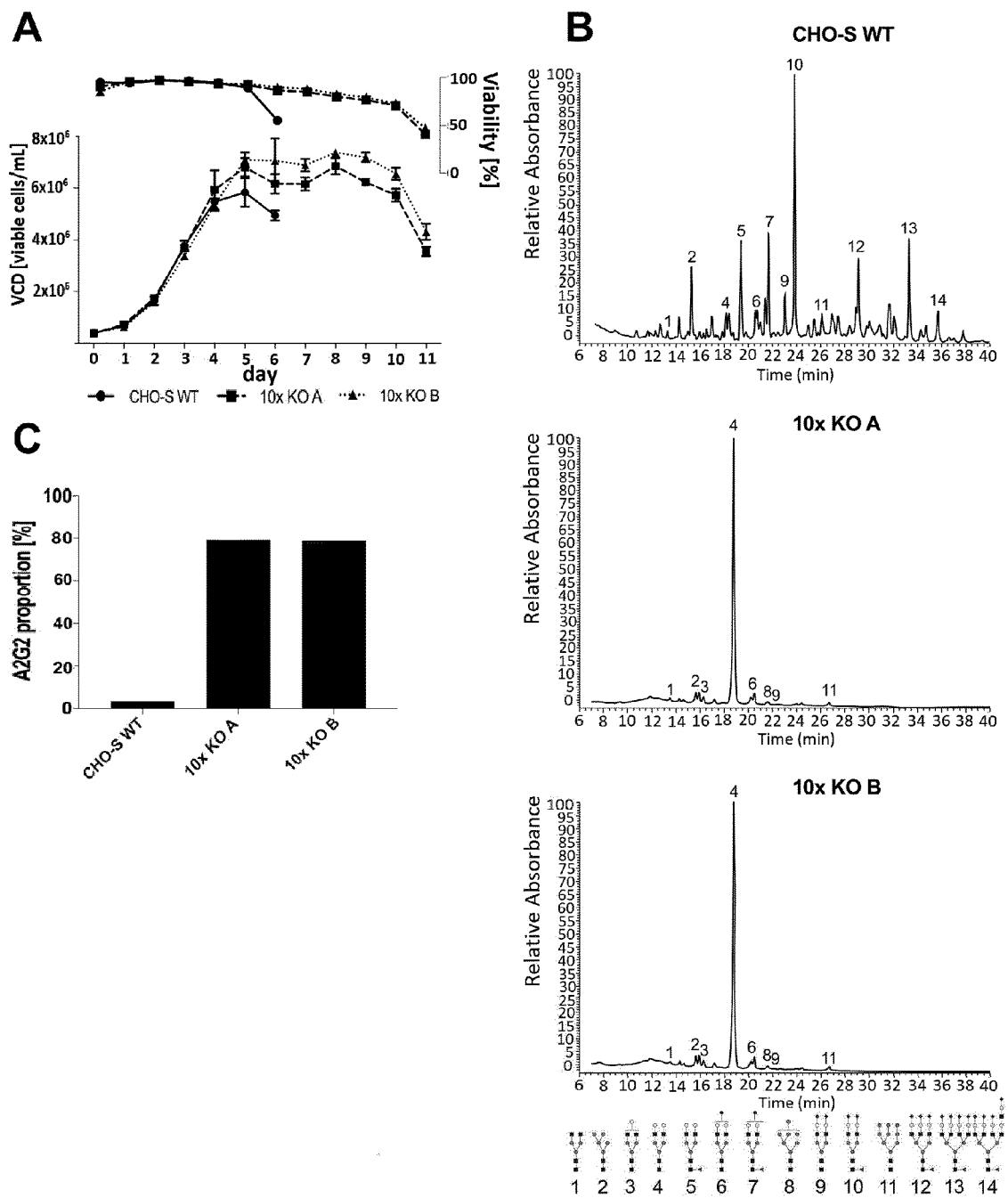

Combined St6Gal1/SerpinG vector map is shown in FIG. 11.

Example 3

N-glycan analysis was performed with GlycoWorks RapiFluor-MS N-Glycan Kit (Waters, Milford, Mass.) according to the manufacturer's instruction. In this case 12 μl of 10× concentrated (MWCO filtered, Amicon Ultra-15, Merck, Darmstadt, Germany) secretome or purified protein sample were used for each. Labeled N-Glycans were analyzed by a LC-MS system using a Thermo Ultimate 3000 HPLC with fluorescence detector coupled on-line to a Thermo Velos Pro Iontrap MS. Separation gradient 30% to 43% buffer and MS was run in positive mode.

Example 4 sgRNA, GFP_2A_Cas9 and A1AT/C1INH_St6gal1_GLUL plasmid design. GFP_2A_Cas9 and single guide RNA (sgRNA) plasmids were constructed as previously described (Gray, L.M. et al., One-step generation of triple knockout CHO cell lines using CRISPR/Cas9 and fluorescent enrichment. Biotechnol. J. 2015, 10, 1446-1456). The sgRNA target design for MGAT4A, MGAT4B, MGAT5, ST3GAL3, ST3GAL4, ST3GAL6, B3GNT2, FUT8, SPPL3 and GLUL was performed using "CRISPy" (Ronda, C. et al., Accelerating genome editing in CHO cells using CRISPR Cas9 and CRISPy, a web-based target finding tool. Biotechnol. Bioeng. 2014, 111, 1604-1616). The target sites for the mentioned genes and the oligos for sgRNA cloning are listed in Table 2 and Table 3, respectively.

TABLE 2 sgRNA target sequences.
The bases in bold mark the PAM site

| Gene name of target | hypothesized KO effect | Target sequence (5'→ 3') |
|---|---|---|
| MGAT4A | decreased branching | GTCTACATTCG TCACTGTCGGG (SEQ ID NO: 1) |
| MGAT4B | decreased branching | GCTTCAGTCGC GGATCCTCT GGG (SEQ ID NO: 2) |
| MGAT5 | decreased branching | GGATGGCTAC CCCCACTGCG AGG (SEQ ID NO: 3) |
| ST3GAL3 | decreased sialylation | GATCCTAGCC CACTTTCGAA AGG (SEQ ID NO: 4) |

TABLE 2-continued sgRNA target sequences.
The bases in bold mark the PAM site

| Gene name of target | hypothesized KO effect | Target sequence (5' → 3') |
|---|---|---|
| ST3GAL4 | decreased sialylation | GTGTCGTCGT TGTGTTGTGG TGG (SEQ ID NO: 5) |
| ST3GAL6 | decreased sialylation | GGAGTTGTGA TCATTGTGAG CGG (SEQ ID NO: 6) |
| B3GNT2 | decreased elongation | GTTGGGCAAG ACGCCCCCG AGG (SEQ ID NO: 7) |
| FUT8 | no core-fucosylation | GTCAGACGCA CTGACAAAGT GGG (SEQ ID NO: 8) |
| SPPL3 | hyper-glycosylation | AGAGAGACGG ACGCTCCAAT AGG (SEQ ID NO: 9) |
| GLUL* | Gln-dependent growth | TCCCAAATCAG CAAACAGACT GG (SEQ ID NO: 10) |

*the GLUL sgRNA efficiency during KO-generation of the presented sequence was very low compared to other target sgRNAs and we recommend the usage of a different design.

TABLE 3

Oligos for sgRNA expression vector cloning.

| Oligo_Name | Oligo sequence (5' → 3') |
|---|---|
| gRNA_MGAT4A_411545_ fwd | GGAAAGGACGAAACACCG TCTACATTCGTCACTGTC GGTTTTAGAGCTAGAAA (SEQ ID NO: 11) |
| gRNA_MGAT4A_411545_ rev | GTAAAAGGAGAGTGAGGA ATGTAGAGGGGTGTTTGG TCGTTTGGAGAAGATAT (SEQ ID NO: 12) |
| gRNA_MGAT4B_1280368 fwd | GGAAAGGACGAAACACCG CTTCAGTCGGGATCCTC TGTTTTAGAGCTAGAAAT (SEQ ID NO: 13) |
| gRNA_MGAT4B_1280368 rev | GTAAAAGAGAGGATCGGG GAGTGAAGGGGTGTTTCG TGCTTTGGAGAAGATAT (SEQ ID NO: 14) |
| gRNA_MGAT5_327084_ fwd | GGAAAGGACGAAACACCG GATGGCTACCCCCACTGC GGTTTTAGAGCTAGAAAT (SEQ ID NO: 15) |
| gRNA_MG_AT5_327084_ rev | GTAAAAGGGGAGTGGGG TAGCGATCGGGTGTTTCG TGCTTTGGAGAAGATAT (SEQ ID NO: 16) |

TABLE 3-continued

Oligos for sgRNA expression vector cloning.

| Oligo_Name | Oligo sequence (5' → 3') |
|---|---|
| gRNA_ST3GAL3_244730_ fwd | GGAAAGGACGAAACACCG ATCCTAGCCCACTTTCGA AGTTTTAGAGGTAGAAAT (SEQ ID NO: 17) |
| gRNA_ST3GAL3_244730_ rev | CTAAAACTTCGAAAGTGG GCTAGGATCGGTGTTTCG TCCTTTCCACAAGATAT (SEQ ID NO: 18) |
| gRNA_ST3GAL4_964386_ fwd | GGAAAGGACGAAACACCGT GTCGTCGTTGTGTTGTGGG TTTTAGAGCTAGAAAT (SEQ ID NO: 19) |
| gRNA_ST3GAL4_964386_ rev | CTAAAACCACAACACAACG ACGACACCGGTGTTTCGTC CTTTCCACAAGATAT (SEQ ID NO: 20 |
| gRNA_ST3GAL6_1812502_ fwd | GGAAAGGACGAAACACCGG AGTTGTGATCATTGTGAGG TTTTAGAGCTAGAAAT (SEQ ID NO: 21) |
| gRNA_ST3GAL6_1812502_ rev | CTAAAACCTCACAATGATC AGAACTCCGGTGTTTCGTG GTTTGGAGAAGATAT (SEQ ID NO: 22) |
| gRNA_B3GNT2_1273293_ fwd | GGAAAGGACGAAACACCGT TGGGCAAGACGCCCCCCGG TTTTAGAGCTAGAAAT (SEQ ID NO: 23) |
| gRNA_B3GNT2_1273293_ rev | CTAAAACCGGGGGGCGTCT TGCCCAACGGTGTTTCGTC CTTTCCACAAGATAT (SEQ ID NO: 24) |
| gRNA_FUT8_681494_ fwd | GGAAAGGACGAAACACCGT CAGACGGACTGACAAAGTG TTTTAGAGCTAGAAAT (SEQ ID NO: 25) |
| gRNA_FUT8_681494_ rev | CTAAAACACTTTGTCAGTG CGTCTGACGGTGTTTCGTC CTTTCCACAAGATAT (SEQ ID NO: 26) |
| gRNA_SPPL3_213040_ fwd | GGAAAGGACGAAACACCAG AGAGACGGACGCTCCAATG TTTTAGAGCTAGAAAT (SEQ ID NO: 27) |
| gRNA_SPPL3_213040_ rev | CTAAAACATTGGAGCGTCC GTCTCTCTGGTGTTTCGTC CTTTCCACAAGATAT (SEQ ID NO: 28) |
| gRNA_GLUL_941540_ fwd | GGAAAGGACGAAACACCGG CCCAGGGAAGCCATCGGAG TTTTAGAGCTAGAAAT (SEQ ID NO: 29) |
| gRNA_GLUL_941540_ rev | CTAAAACTCCGATGGCTTC CCTGGGCCGGTGTTTCGTC CTTTCCACAAGATAT (SEQ ID NO: 30) |

Plasmids for co-expression of A1AT/C1INH and St6gal1 were constructed with uracil-specific excision reagent cloning method as previously described (Pristovšek, N. et al., Using Titer and Titer Normalized to Confluence Are Complementary Strategies for Obtaining Chinese Hamster Ovary Cell Lines with High Volumetric Productivity of Etanercept. Biotechnol. J. 2018, 13; and Lund, A. M. et al., A Versatile System for USER Cloning-Based Assembly of Expression Vectors for Mammalian Cell Engineering. PLOS ONE 2014, 9(5): e96693). The DNA sequences of the plasmids are listed in FIG. 17.

Cell cultivation and transfection for genome editing.

CHO-S suspension cells were incubated in a humidified incubator at 120 rpm, 37° C., 5% CO2, passaged to 2-3×105 cells/mL every 2-3 days and transfected in 6-well plates (BD Biosciences, San Jose, Calif.) as described previously (Gray, L. M. et al., One-step generation of triple knockout CHO cell lines using CRISPR/Cas9 and fluorescent enrichment. Biotechnol. J. 2015, 10, 1446-1456). The GFP_2A_Cas9/ sgRNA plasmid ratios for each transfection was 1:1 of which the plasmid load of sgRNA was divided equally by the amount of different sgRNAs used per transfection (Table 5). To measure FACS sorting efficiency, pmaxGFP® vector (Lonza, Basel, Switzerland) transfection was performed as well. Cells were harvested for fluorescence-activated cell sorting (FACS) 48 h post transfection.

Cas9 and fluorescent enrichment. Biotechnol. J. 2015, 10, 1446-1456). PCR primers are presented in Table 6.

TABLE 6

Primer list for deep sequencing (MiSeq).
The primers contain overhang sequences
compatible with Illumina Nextera XT indexing
(forward primeroverhang:
TCGTCGGCAGCGTCAGATGTGTATAAGAGACAG
(SEQ ID NO: 33),
reverse primeroverhang:
GTCTCGTGGGCTCGGAGATGTGTATAAGAGACAG
(SEQ ID NO: 34))

| primer name | sequence (5' → 3') |
|---|---|
| MiSeq_MGAT4A_411545_fwd | TCGTCGGCAGCGTCAGATGTGTATAAGAGACAGGACAGACAGAAGGCAAATCTACG (SEQ ID NO: 35) |
| MiSeq_MGAT4A_411545_rev | GTCTCGTGGGCTCGGAGATGTGTATAAGAG |

TABLE 5

Indels generated in ten targeted genes by CRISPR/Cas9 multiplexing.

| | Multiplexing round | | | | | | | | | |
|---|---|---|---|---|---|---|---|---|---|---|
| | 1 | | | | 2 | | 3 | | | 4 |
| Gene | MGAT4A | MGAT4B | MGAT5 | ST3GAL4 | ST3GAL6 | ST3GAL3 | B3GNT2 | GLUL | SPPL3 | FUT8 |
| 10x KO clone A | +2 | −1 | +1 | −5/+1 | +1 | +1/+2 | −1 | −13/−10/−2 | +1 | +1 |
| 10x KO clone B | +2 | −1 | +1 | −5/+1 | +1 | +1/+2 | −1 | −13/−10/−2 | +1 | −7/−1 |

Single cell cloning of genome edited cells using FACS.

Before FACS, cells were filtered through a 40 μm cell strainer into a FACS-compatible tube.

Single fluorescent-positive (GFP) cells were sorted into 384-well plates (Corning, New York, N.Y.) containing 30 μL CD CHO medium supplemented with 8 mM L-glutamine, 1.5% HEPES buffer and 1% Antibiotic-Antimycotic (Gibco, Waltham, Mass.) per well as described previously (Hansen, H. G. et al, Case study on human alpha1-antitrypsin: Recombinant protein titers obtained by commercial ELISA kits are inaccurate. Biotechnol. J. 2016, 11, 1648-1656). For cell sorting, fluorescent-positive cell populations were gated based on non-transfected WT CHO-S cells. Two weeks after cell sorting cell colonies were moved to 96-well flat-bottom plates (BD Biosciences) and expanded for deep sequencing analysis and batch cultivation.

Deep sequencing analysis. Confluent colonies from 96-well flat-bottom replicate plates were harvested for genomic DNA extraction. DNA extraction was performed using QuickExtract DNA extraction solution (Epicentre, Illumina, Madison, Wis.) according to the manufacturer's instruction. The library preparation was based on Illumina 16S Metagenomic Sequencing Library Preparation and deep sequencing was carried out on a MiSeq Benchtop Sequencer (Illumina, San Diego, Calif.). The protocol for amplifying the targeted genomic sequences, amplicon purification, adapter-PCR and following quality analysis was based on previously published work (Gray, L. M. et al., One-step generation of triple knockout CHO cell lines using CRISPR/

TABLE 6-continued

Primer list for deep sequencing (MiSeq).
The primers contain overhang sequences
compatible with Illumina Nextera XT indexing
(forward primeroverhang:
TCGTCGGCAGCGTCAGATGTGTATAAGAGACAG
(SEQ ID NO: 33),
reverse primeroverhang:
GTCTCGTGGGCTCGGAGATGTGTATAAGAGACAG
(SEQ ID NO: 34))

| primer name | sequence (5' → 3') |
|---|---|
|  | ACAGTTAACAGCTACACAGGAAGAGCA (SEQ ID NO: 36) |
| MiSeq_MGAT4B_1280368_fwd | TCGTCGGCAGCGTCAGATGTGTATAAGAGACAGGGGATGGGGTGTATGGAGGT (SEQ ID NO: 37) |
| MiSeq_MGAT4B_1280368_rev | GTCTCGTGGGCTCGGAGATGTGTATAAGAGACAGTTGCAGACTGCTCTCCTTGG (SEQ ID NO: 38) |

TABLE 6-continued

Primer list for deep sequencing (MiSeq).
The primers contain overhang sequences
compatible with Illumina Nextera XT indexing
(forward primeroverhang:
TCGTCGGCAGCGTCAGATGTGTATAAGAGACAG
(SEQ ID NO: 33),
reverse primeroverhang:
GTCTCGTGGGCTCGGAGATGTGTATAAGAGACAG
(SEQ ID NO: 34))

| primer name | sequence (5' → 3') |
|---|---|
| MiSeq_MGAT5_327084_fwd | TCGTCGGCAGCGTCAGATGTGTATAAGAGACAGCATGAATCTCATGGTTTCCTTTGT (SEQ ID NO: 39) |
| MiSeq_MGAT5_327084_rev | GTCTCGTGGGCTCGGAGATGTGTATAAGAGACAGGCTTCAAGACTCAACTCTTTCCC (SEQ ID NO: 40) |
| MiSeq_ST3GAL3_244730_fwd | TCGTCGGCAGCGTCAGATGTGTATAAGAGACAGGGGAAACAGCATGGGCAAAC (SEQ ID NO: 41) |
| MiSeq_ST3GAL3_244730_rev | GTCTCGTGGGCTCGGAGATGTGTATAAGAGACAGACTGGAATGTGGATGGTGGC (SEQ ID NO: 42) |
| MiSeq_ST3GAL4_964386_fwd | TCGTCGGCAGCGTCAGATGTGTATAAGAGACAGACACCTGATGACCACATCGT (SEQ ID NO: 43) |
| MiSeq_ST3GAL4_964386_rev | GTCTCGTGGGCTCGGAGATGTGTATAAGAGACAGGCAGGGTCCACTTCTGGATT (SEQ ID NO: 44) |
| MiSeq_ST3GAL6_1812502_fwd | TCGTCGGCAGCGTCAGATGTGTATAAGAGACAGTCACTGTCTTACTACCCACAGGA (SEQ ID NO: 45) |
| MiSeq_ST3GAL6_1812502_rev | GTCTCGTGGGCTCGGAGATGTGTATAAGAGACAGTCCTTTCATTATATTCAAGAGCCAC (SEQ ID NO: 46) |
| MiSeq_B3GNT2_1273293_fwd | TCGTCGGCAGCGTCAGATGTGTATAAGAGACAGCTCACCCACCGGAGAACAG (SEQ ID NO: 47) |
| MiSeq_B3GNT2_1273293_rev | GTCTCGTGGGCTCGGAGATGTGTATAAGAGACAGAGAAGGCAAGCAATTCGGGA (SEQ ID NO: 48) |
| MiSeq_FUT8_681494_fwd | TCGTCGGCAGCGTCAGATGTGTATAAGAGACAGTGCCCCCATGACTAGGGATA (SEQ ID NO: 49) |
| MiSeq_FUT8_681494_rev | GTCTCGTGGGCTCGGAGATGTGTATAAGAGACAGTCTGCGTTCGAGAAGCTGAAA (SEQ ID NO: 50) |
| MiSeq_SPPL3_213040_fwd | TCGTCGGCAGCGTCAGATGTGTATAAGAGACAGCGTGGAGTAACTTACCTGCTGT (SEQ ID NO: 51) |
| MiSeq_SPPL3_213040_rev | GTCTCGTGGGCTCGGAGATGTGTATAAGAGACAGAAGTGGTGAGTGTGTCCTGT (SEQ ID NO: 52) |
| MiSeq_GLUL_941540_fwd2 | TCGTCGGCAGCGTCAGATGTGTATAAGAGACAGCAACCAGCACCCCTGGTT (SEQ ID NO: 53) |
| MiSeq_GLUL_941540_rev2 | GTCTCGTGGGCTCGGAGATGTGTATAAGAGACAGCAGCTGCCAGTCTGTTTGC (SEQ ID NO: 54) |

Transfection and expression in polyclonal cell lines by applying MSX-selection Cells were seeded in 250 mL Corning vent cap shake flasks (Sigma-Aldrich) as duplicates with cell densities ~1×106 cells/mL in 60 mL CD CHO medium supplemented with 8 mM L-glutamine (Life Technologies) and transfected with 75 µg of A1AT-GLUL-St6gal plasmid or 75 µg of C1INH-GLUL-St6gal1 plasmid using FreeStyle™ MAX reagent together with OptiPRO SFM medium (Life Technologies) according to the manufacturer's recommendations. 1 µL/mL anti-clumping agent was added 24 h after transfection. pmaxGFP® vector (Lonza) transfection was performed to measure transfection efficiencies. Two days after transfection, cells were transferred into 60 mL CD CHO medium lacking L-glutamine (Life Technologies) and supplemented with 1 µL/mL anti-clumping agent and 0 µM, 10 µM, 30 µM or 50 µM MSX (EMD Millipore, Billerica, Mass.).

Cell densities and viabilities were determined once per day using the NucleoCounter NC-250 Cell Counter (ChemoMetec). The cells were passaged in fresh selection medium every 2-3 days until viability and doubling time reached stable values. Polyclonal cell lines (pools) were seeded in duplicates at ~1×106 cells/mL with corresponding MSX concentrations. Cell densities and viabilities were determined once per day and supernatants of the pools were harvested three days after seeding and pooled within duplicates for purification of rhA1AT and rhC1INH.

Single cell cloning of cells from polyclonal cell pools using FACS

Non-stained single cells were sorted from pools as described above. For cell sorting, all viable cells were gated for sorting into 384-well plates with L-glutamine-free medium. Two weeks after cell sorting the clones were moved to 96-well flat-bottom plates (BD Biosciences) and expanded to shake flask format in CD CHO medium supplemented with 1 µL/mL anti-clumping agent, 25 µM MSX and lacking L-glutamine.

Screening cell pools and single cell clones for human-like α-2,6-sialic acid linkage formation with lectin staining.

For lectin staining of cells, triplicates of 10,000 cells per sample were diluted in 200 pL of 0.22 µm pore size filtered CD CHO medium (Life Technologies) supplemented with 5 µg/mL Hoechst 33342 (Merck, Darmstadt, Germany) and 1 µg/mL Fluorescein isothiocyanate (FITC) labeled Sambucus nigra agglutinin (SNA) lectin (Biomol, Hamburg, Germany). After 60 min incubation in the dark at 37° C. and 5% $CO_2$ the cells were washed with 200 µL CD CHO medium and then washed twice with 200 µL phosphate buffered saline (PBS) (300g, 5 min, RT). The samples were resuspended in 200 µl PBS and transferred to 96-well plate for final centrifugation at 300 g for one minute. Percentage of FITC SNA positive cells was determined in a 96-well optical-bottom microplate (Greiner Bio-One, Frickenhausen, Germany) using a Celigo Imaging Cell Cytometer (Nexcelom Bioscience, Lawrence, Mass.). Cells were identified using the blue channel (Hoechst-positive cells), and the green channel (FITC SNA-positive cells) was used to detect cells with alpha-2,6-sialic acid linkage. A Hoechst/FITC SNA-stained CHO-S WT sample was gated to distinguish between FITC-positive and FITC-negative cells.

Batch cultivation: cell growth analysis and N-glycosylation profiling.

For batch cultivation and N-glycan analysis, cells were seeded at $0.4 \times 10^6$ cells/mL in 250 mL Corning vent cap shake flasks (Sigma-Aldrich, St. Louis, Mo.) as duplicates in 60 mL CD CHO medium supplemented with 1 µL/mL anti-clumping agent (Life Technologies). CHO-S WT and non-producing parental 10× KO cell lines were additionally supplemented with 8 mM L-glutamine. rhA1AT/rhC1INH producing clones were cultivated in L-glutamine-free medium at all times and passaged in medium containing 25 µM MSX until the batch cultivation was initiated. Cell densities and viabilities were determined once per day using the NucleoCounter NC-250 Cell Counter (ChemoMetec) until the viability was <70%, at which point the culture was terminated. Supernatant samples with total secreted protein (secretome) from CHO-S WT and parental, non-producing 10× KO cell lines were taken five days after seeding and pooled within biological replicates. The volume for secretome samples was calculated to harbor $20 \times 10^6$ cells. For all shake flasks, additional supernatant samples were taken by centrifuging 1 mL of cell suspension for 5 minutes at 1000 g and storage of supernatant at −80° C. until further analysis.

rhA1AT and rhC1INH Purification rhA1AT and rhC1INH were purified using CaptureSelect affinity resins (Thermo Fisher Scientific) according to the manufacturer's instructions. rhA1AT was further purified by size exclusion chromatography on a Superdex 200 increase 10/300GL column (GE Healthcare) equilibrated in PBS.

Titer assessment of rhA1AT/rhC1INH producing clones rhA1AT and rhC1INH titers were determined using biolayer interferometry on an Octet RED96 (Pall, Menlo Park, Calif., USA) as described previously for A1AT (Noh, S.M. et al., Reduction of ammonia and lactate through the coupling of glutamine synthetase selection and downregulation of lactate dehydrogenase-A in CHO cells. Appl. Microbiol. Biotechnol. 2017, 101, 1035-1045). After hydration in PBS, streptavidin biosensors (18□5021, Fortebio, Pall) were functionalized with CaptureSelect biotin anti-A1AT conjugate or CaptureSelect biotin anti-C1INH conjugate (Thermo Fisher Scientific) at 5 pg/mL in PBS, and blocked in PBS containing 1 µg/mL biocytin (600 and 300 s incubation steps, respectively). Standards were prepared in spent CHO-S medium using plasma-derived A1AT (Athens Research & Technology) at 100, 50, 25, 12.5, 6.3, 3.1 and 1.6 pg/mL or C1INH (R&D systems) at 40, 20, 10, 5, 2.5, 1.25 and 0.625 pg/mL. Samples and standards were diluted two-fold and contained 0.1% BSA w/v, 0.1% tween-20 v/v, and 500 mM NaCl. When needed, samples were further diluted to fall within the range of the standard dilution series. After equilibration in spent CHO-S medium (120 s), samples and standards were measured for 300 s with a shaking speed of 1000 rpm at 30° C. Regeneration was performed with 50 mM TRIS, 2 M $MgCl_2$, pH 7.5. Assays were performed in 96-well black microplates (Greiner Bio-One, Kremsmünster, Austria). Octet System Data Analysis 7.1 software was used to calculate binding rates and absolute A1AT and C1INH concentrations.

SDS-PAGE, Isoelectric Focusing and PNGase Treatment

SDS-PAGE was performed on Novex 4-12% Tris-Glycine mini gels and isoelectric focusing (IEF) was performed on Novex pH 3-10 IEF gels (Thermo Fisher Scientific) as per the manufacturer's instructions. Deglycosylation with PNGase F was performed according to the manufacturer's instructions (New England Biolabs, Ipswich, Mass.).

Activity Assays

A1AT inhibitory activity was determined using the EnzChek Elastase Assay Kit (Molecular Probes, Eugene, Oreg.) according to the manufacturer's instructions. In short, A1AT (8.0, 4.0, 2.0, 1.0, 0.5, 0.25, 0.13, and 0.06 µM) was incubated with purified active porcine pancreatic elastase and fluorescently labelled substrate (DQ-elastin). Measurement of fluorescence was performed after 45 min at room temperature (Excitation: 485 nm, slit width 9.0 nm; Emission: 530 nm, slit width 13.5 nm).

C1INH inhibitory activity was determined using the Technochrom C1INH Assay Kit (TechnoClone, Vienna, Austria). In short, plasma containing C1INH activity (120%, 60%, 30%) and samples (~0.25 µM) were incubated with substrate-buffer mixture for 3 min at room temperature, after which 50% acetic acid was added. Extinction was measured at 405 nm.

N-Glycan Analysis

N-glycans were derivatized with GlycoWorks RapiFluor-MS N-Glycan Kit (Waters, Milford, Mass.) according to the manufacturer's instruction. Briefly; 12 µg purified protein or 12 µl of 10× concentrated (Amicon Ultra-15, Merck) secretome sample were used for each sample. Labeled N-Glycans were analyzed by LC-MS as described previously (Gray, L. M. et al., One-step generation of triple knockout CHO cell lines using CRISPR/Cas9 and fluorescent enrichment. Biotechnol. J. 2015, 10, 1446-1456) Separation gradient from 30% to 43% 50 mM ammonium formate buffer and MS were run in positive mode. Amount of N-Glycan was measured by integrating the peaks with Thermo Xcalibur software (Thermo Fisher Scientific, Waltham, Mass.) giving the normalized, relative amount of the glycans.

Results

Growth Profile and N-Glycan Profile of Clonal 10× KO Cell Lines

The aim of our study was to produce rhA1AT and rhC1INH in CHO cells with N-glycan profiles similar to human plA1AT and pIC1INH. Our approach was to engineer the heterogeneous N-glycan profile of CHO-S WT cells towards a homogeneous A2G2S2 N-glycan structure, which is the predominant N-glycan on plA1AT/p1C1INH. To this end, we generated out-of-frame insertions or deletions (indels) in eight glycosyltransferases (MGAT4A, MGAT4B, MGAT5, ST3GAL3, ST3GAL4, ST3GAL6, B3GNT2, FUT8) as well as in the genes SPPL3 and GLUL (Table 5) over four successive rounds of multiplexed CRISPR/Cas9 gene editing. Two clones with indels in the targeted genes were subjected to growth analysis and N-glycan profiling.

Two clones (10× KO A and 10× KO B) with out-of-frame indels in all ten gene targets were obtained and both showed a pronounced increase in batch culture longevity when compared to the parental CHO-S WT cell line (FIG. 12A). CHO-S WT reached maximal viable cell density of ~6×106 cells/mL on day five and cell viability declined rapidly to <50% on day 6. In contrast, the 10× KO A and 10× KO B clones had cell viabilities >75% until day 10 of the batch cultivation and reached higher maximal viable cell density than CHO-S WT.

N-glycan analysis of the CHO-S WT secretome resulted in more than 25 N-glycan structures (FIG. 12B) where the A2G2S2 structure with alpha-2,6-linked sialic acids, predominantly found on plA1AT and pIC1INH, was not detected. The majority of CHO-S WT N-glycans contained core-fucosylation. The N-glycans produced by CHO-S WT cells appear diverse and comprise high-mannose structures as well as non-galactosylated, fully and partially sialylated di-, tri- and tetra-antennary structures (all with alpha-2,3-linked sialic acids). A2FG2S2 was found as the main N-glycan on total secreted proteins of CHO-S WT. In contrast, the N-glycan profiles of 10× KO A and 10× KO B are more homogeneous (FIG. 12B) with all structures lacking core-fucosylation. In addition, only relatively small amounts of CHO-specific alpha-2,3-linked sialylation were present.

After disruption of the targeted genes, the proportion of A2G2 within N-glycan structures of total secreted proteins was increased from 3.5% (CHO-S WT) to 79% in both 10× KO clones (FIG. 12C). We concluded that the 10× KO A and B clones were suitable host cell lines in our effort to generate humanized N-glycans.

Introducing human-like sialylation in 10× KO cell lines

On the basis of A2G2 secretome N-glycan structures of clone 10× KO B, we aimed to develop clonal cell lines expressing St6gall and rhC1INH or St6gall and rhA1AT. We envisioned that such cell lines are capable to produce rhA1AT or rhC1INH with predominant A2G2S2 N-glycan structures as found on plA1AT and pIC1INH. The functional GLUL-KO selection system was confirmed by MSX-dosage dependent recovery times of cell viabilities from transfected cell pools. Passaging of the different transfection pools was performed until viability and doubling times were stable. We then conducted FACS-based single cell cloning with the 50 µM MSX-selected cells. During the expansion of the generated clones, only clones exhibiting predominant FITC-SNA staining and detectable levels of rhA1AT/rhC1INH in supernatants on coomassie-stained SDS-PAGE gels were selected. Based on these criteria, two rhA1AT (A1-1 and A1-2) and two rhC1INH (C1-1 and C1-2) producing clones were selected for further characterization.

SNA lectins are reported to bind predominantly to sialic acids of N-glycans linked to the galactose residue in a human-like alpha-2,6-sialylation. Analyzing FITC-SNA-stained CHO-S WT, we found relatively low levels of alpha-2,6-sialylation (FIG. 13A). To determine the proportion of cells with human-like sialylation, FITC-SNA stained CHO-S WT samples were used to gate between FITC-positive and FITC-negative cells. Within the two 50 µM MSX-selected polyclonal cell lines, <30% of the cells were found to comprise alpha-2,6-linked sialic acids on N-glycans of cell surface proteins (FIG. 13B). In comparison, 82-90% of the cells in the populations of the selected four clones (A1-1, A1-2, C1-1 and C1-2) had the desired alpha-2,6-linked sialic acids on their N-glycans.

SDS-PAGE gel analysis revealed that purified rhA1AT and rhC1INH produced in the four clones seem to have hydrodynamic volumes (molecular weight) similar to plA1AT and pIC1INH without detectable impurities as seen in pIC1INH (FIG. 15A). rhA1AT and rhC1INH produced in CHO-S WT background did not co-migrate with plA1AT and pIC1INH, respectively. However, after deglycosylation with PNGaseF, all recombinantly produced proteins aligned with corresponding bands of plA1AT and pIC1INH with the exception of rhC1INH produced in a CHO-S WT background displayed an additional protein band at ~65 kDa.

To further characterize the CHO-produced rhA1AT and rhC1INH, we performed IEF gel analysis (FIG. 15B). rhA1AT from clones A1-1 and A1-2 manifested in two bands with isoelectric points (pI) around pH 4.5 similar to plA1AT. In contrast, rhA1AT produced in a CHO-S WT background displayed more than nine detectable isoforms with pI between pH 4-5.

IEF gel analysis of rhCiINH produced in a CHO-S WT background resulted in isoforms with pI ranging from pH ~4-5. A high degree of heterogeneity was also found in purified rhC1INH produced in clone C1-1. However, rhC1INH produced in clone C1-2 was less heterogeneous with pI at pH ~3.5 similar to plC1INH.

In N-glycan analysis of purified rhA1AT and rhC1INH from CHO-S WT cells we detected a higher degree of heterogeneity compared to N-glycan structures on rhA1AT and rhC1INH from polyclonal 10× KO cell pools. The polyclonal cell lines revealed two predominant sugar structures on both proteins (A2G2 and A2G2S2 N-glycans), whereas we could not detect the A2G2S2 structure on products from CHO-S WT. Moreover, the amount of predominant N-glycan structures on rhA1AT and rhC1INH was decreased from two (polyclonal pools) to one (monoclonal producers), identified as A2G2S2 N-glycan.

All four 10× KO-derived monoclonal cell lines produced rhA1AT and rhC1INH with higher proportion of A2G2S2 structures than plA1AT and plC1INH (FIG. 15C). The proportion of A2G2S2 in rhA1AT and rhC1INH was approximately 88-92% and 84%, respectively, and 82% for plA1AT and 66% for plC1INH.

Finally, we investigated the activity of purified rhA1AT and rhC1INH. rhA1AT activity was determined by its inhibitory function of elastase activity (FIG. 15D). Similar to plA1AT, a decrease in elastase activity was detected at A1AT concentrations >0.1 µM for rhA1AT from clones A1-1 and A1-2. In addition, 50% of elastase inhibition was reached at ~0.3 µM A1AT for plA1AT as well as rhA1AT. In vitro activity of purified rhC1INH produced by clones C1-1 and C1-2 was similar or higher compared to plC1INH.

Example 5

1 engineered CHO Cell line with KO of the Sppl3 gene and CHO-S wt cells were both transiently transfected using chemical transfection with plasmids encoding either a Erythropoietin or C1inhibitor gene fused to a HPC4-affinity purification tag. The transfected cells were grown for 72 hours in CD CHO+8 mM L-gln using standard conditions as described previously, after which the supernatant was harvested, sterile filtered and stored at −80° C.

For protein purification, the supernatants were thawed and purified by affinity chromatography using a 1-mL anti-protein C affinity column for EPO and C1inhibitor, and the fractions containing the EPO and C1inhibitor respectively were pooled.

N-glycan analysis was performed on the purified samples, with GlycoWorks RapiFluor-MS N-Glycan Kit (Waters, Milford, Mass.) according to the manufacturer's instruction. In this case 12 μl of purified protein sample were used for each. Labeled N-Glycans were analyzed by a LC-MS system using a Thermo Ultimate 3000 HPLC with fluorescence detector coupled on-line to a Thermo Velos Pro Iontrap MS. Separation gradient 30% to 43% buffer and MS was run in positive mode.

---

The invention claimed is:

1. A recombinant mammalian cell having the endogenous genes Mgat4A, Mgat4B, Mgat5, St3Gal4, St3Gal6, SPPL3, and FUT8 inactivated and/or downregulated.

2. The recombinant mammalian cell according to claim 1, wherein the endogenous gene also is inactivated and/or downregulated.

3. The recombinant mammalian cell according to claim 1, wherein the endogenous gene B3GNT2 is present.

4. The recombinant mammalian cell according to claim 1, wherein the endogenous gene B3GNT2 is inactivated and/or downregulated.

5. The recombinant mammalian cell according to claim 1, wherein the endogenous gene GLUL is inactivated and/or downregulated.

6. The recombinant mammalian cell according to claim 1, which is an in vitro cell line.

7. The recombinant mammalian cell according to claim 1, where the cell has been further modified to express an exogenous human glycoprotein of interest.

8. The recombinant mammalian cell according to claim 7, where said exogenous human glycoprotein of interest is a human serum protein.

9. The recombinant mammalian cell according to claim 7, which cell line produces said glycoprotein of interest with a primary n-glycan structure that is a fully sialylated bi-antennary structure without core fucosylation.

10. The recombinant mammalian cell according to claim 9, which glycan structure is according to the structure A2G2S2 with the following pictorial representations:

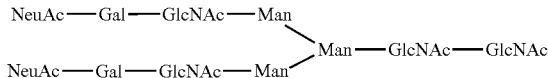

11. The recombinant mammalian cell according to claim 7, which exogenous human glycoprotein of interest is selected from Plasma protease C1 inhibitor (C1InH) glycosylated at one or more positions selected from Asn3, Asn47, Asn59, Asn216, Asn231, Asn250, and Asn330; Antithrombin-III (ATIII) glycosylated at one or more positions selected from Asn96, Asn135, Asn155 and Asn192; and Human alpha-1-antitrypsin (AAT) glycosylated at one or more of the positions Asn46, Asn83, and Asn247.

12. The recombinant mammalian cell according to claim 1, which is selected from the group consisting of a Chinese Hamster Ovarian (CHO) cell, a Baby Hamster Kidney (BHK) cell, COS cell, HEK293, NS0, SP2/0, YB2/0, HUVEC, HKB, PER-C6, and NS0, or a derivatives of any of these cells.

13. The recombinant mammalian cell according to claim 8, where said exogenous human glycoprotein of interest is a human serpin.

14. The recombinant mammalian cell according to claim 13, where said human serpin is selected from the group consisting of SERPINA1, SERPINA2, SERPINA3, SERPINA4, SERPINA5, SERPINA6, SERPINA7, SERPINA8, SERPINA9, SERPINA10, SERPINA11, SERPINA12, SERPINA13, SERPINB1, SERPINB2, SERPINB3, SERPINB4, SERPINB5, SERPINB6, SERPINB7, SERPINB8, SERPINB9, SERPINB10, SERPINB11, SERPINB12, SERPINB13, SERPINC1, SERPIND1, SERPINE1, SERPINE2, SERPINE3, SERPINF1, SERPINF2, SERPING1, SERPINH1, SERPINI1, and SERPINI2.

15. The recombinant mammalian cell according to claim 10, which glycan structure is according to the structure A2G2S2 with the following pictorial representation:

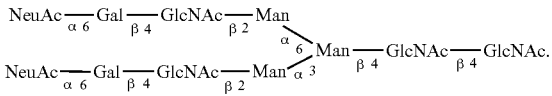

16. The recombinant mammalian cell according to claim 2, wherein a gene encoding ST6Gal1 is inserted.

17. The recombinant mammalian cell according to claim 12, which is a CHO cell.

18. The recombinant mammalian cell according to claim 17, wherein the CHO cell is a CHO-K1 cell or a CHO-S cell.

19. A method for the production of a recombinant protein of interest, the method comprising the steps of:
a) culturing a population of recombinant mammalian cells according to claim 7 in a suitable cell culture medium; and
b) harvesting said human protein of interest from the cell culture or cell culture medium.

20. The method according to claim 19, wherein said protein of interest is produced with a glycan structure similar or identical to the glycan profile of said glycoprotein of interest found in human plasma.

21. A recombinant CHO cell line having the endogenous genes Mgat4A, Mgat4B, Mgat5, St3Gal3, St3Gal4, St3Gal6, B3GNT2 , SPPL3, and FUT8 inactivated and a gene encoding human St6Gal1 inserted.

22. The recombinant CHO cell line according to claim 21, which has been further modified to express an exogenous human glycoprotein of interest.

23. The recombinant CHO cell line according to claim 22, wherein the exogenous human glycoprotein of interest is human serpin selected from the group consisting of SERPINA1, SERPINA2, SERPINA3, SERPINA4, SERPINA5, SERPINA6, SERPINA7, SERPINA8, SERPINA9, SERPINA10, SERPINA11, SERPINA12, SERPINA13, SERPINB1, SERPINB2, SERPINB3, SERPINB4, SERPINB5, SERPINB6, SERPINB7, SERPINB8, SERPINB9, SERPINB10, SERPINB11, SERPINB12, SERPINB13, SERPINC1, SERPIND1, SERPINE1, SERPINE2, SERPINE3, SERPINF1, SERPINF2, SERPING1, SERPINH1, SERPINI1, and SERPINI2.

24. The recombinant CHO cell line according to claim 23, wherein the human serpin is SERPINC1.

* * * * *

UNITED STATES PATENT AND TRADEMARK OFFICE
CERTIFICATE OF CORRECTION

PATENT NO. : 11,624,080 B2
APPLICATION NO. : 16/767531
DATED : April 11, 2023
INVENTOR(S) : Bjørn Gunnar Voldborg et al.

Page 1 of 1

It is certified that error appears in the above-identified patent and that said Letters Patent is hereby corrected as shown below:

On the Title Page

At item (57), Line 3, "semm" should be -- serum --.

In the Claims

At Column 59, Line 56, "having" should be -- having: --.

At Column 59, Line 61, "gene" should be -- gene St3Gal3 --.

Signed and Sealed this
First Day of August, 2023

Katherine Kelly Vidal
*Director of the United States Patent and Trademark Office*

SEQUENCE LISTING

```
<160> NUMBER OF SEQ ID NOS: 54

<210> SEQ ID NO 1
<211> LENGTH: 23
<212> TYPE: DNA
<213> ORGANISM: Artificial Sequence
<220> FEATURE:
<223> OTHER INFORMATION: DNA target sequence

<400> SEQUENCE: 1
gtctacattc gtcactgtcg ggg                                             23

<210> SEQ ID NO 2
<211> LENGTH: 23
<212> TYPE: DNA
<213> ORGANISM: Artificial Sequence
<220> FEATURE:
<223> OTHER INFORMATION: DNA target sequence

<400> SEQUENCE: 2
gcttcagtcg cggatcctct ggg                                             23

<210> SEQ ID NO 3
<211> LENGTH: 23
<212> TYPE: DNA
<213> ORGANISM: Artificial Sequence
<220> FEATURE:
<223> OTHER INFORMATION: DNA target sequence

<400> SEQUENCE: 3
ggatggctac ccccactgcg agg                                             23

<210> SEQ ID NO 4
<211> LENGTH: 23
<212> TYPE: DNA
<213> ORGANISM: Artificial Sequence
<220> FEATURE:
<223> OTHER INFORMATION: DNA target sequence

<400> SEQUENCE: 4
gatcctagcc cactttcgaa agg                                             23

<210> SEQ ID NO 5
<211> LENGTH: 23
<212> TYPE: DNA
<213> ORGANISM: Artificial Sequence
<220> FEATURE:
<223> OTHER INFORMATION: DNA target sequence

<400> SEQUENCE: 5
gtgtcgtcgt tgtgttgtgg tgg                                             23

<210> SEQ ID NO 6
<211> LENGTH: 23
```

```
<212> TYPE: DNA
<213> ORGANISM: Artificial Sequence
<220> FEATURE:
<223> OTHER INFORMATION: DNA target sequence

<400> SEQUENCE: 6
ggagttgtga tcattgtgag cgg                                              23

<210> SEQ ID NO 7
<211> LENGTH: 23
<212> TYPE: DNA
<213> ORGANISM: Artificial Sequence
<220> FEATURE:
<223> OTHER INFORMATION: DNA target sequence

<400> SEQUENCE: 7
gttgggcaag acgcccccg agg                                               23

<210> SEQ ID NO 8
<211> LENGTH: 23
<212> TYPE: DNA
<213> ORGANISM: Artificial Sequence
<220> FEATURE:
<223> OTHER INFORMATION: DNA target sequence

<400> SEQUENCE: 8
gtcagacgca ctgacaaagt ggg                                              23

<210> SEQ ID NO 9
<211> LENGTH: 23
<212> TYPE: DNA
<213> ORGANISM: Artificial Sequence
<220> FEATURE:
<223> OTHER INFORMATION: DNA target sequence

<400> SEQUENCE: 9
agagagacgg acgctccaat agg                                              23

<210> SEQ ID NO 10
<211> LENGTH: 23
<212> TYPE: DNA
<213> ORGANISM: Artificial Sequence
<220> FEATURE:
<223> OTHER INFORMATION: DNA target sequence

<400> SEQUENCE: 10
tcccaaatca gcaaacagac tgg                                              23

<210> SEQ ID NO 11
<211> LENGTH: 54
<212> TYPE: DNA
<213> ORGANISM: Artificial Sequence
<220> FEATURE:
<223> OTHER INFORMATION: DNA Oligo for sgRNA expression vector cloning

<400> SEQUENCE: 11
ggaaaggacg aaacaccgtc tacattcgtc actgtcggtt ttagagctag aaat            54

<210> SEQ ID NO 12
<211> LENGTH: 53
<212> TYPE: DNA
<213> ORGANISM: Artificial Sequence
<220> FEATURE:
<223> OTHER INFORMATION: DNA Oligo for sgRNA expression vector cloning

<400> SEQUENCE: 12
```
ctaaaacgac agtgacgaat gtagaccggt gtttcgtcct ttccacaaga tat    53

<210> SEQ ID NO 13
<211> LENGTH: 54
<212> TYPE: DNA
<213> ORGANISM: Artificial Sequence
<220> FEATURE:
<223> OTHER INFORMATION: DNA Oligo for sgRNA expression vector cloning

<400> SEQUENCE: 13
ggaaaggacg aaacaccgct tcagtcgcgg atcctctgtt ttagagctag aaat    54

<210> SEQ ID NO 14
<211> LENGTH: 53
<212> TYPE: DNA
<213> ORGANISM: Artificial Sequence
<220> FEATURE:
<223> OTHER INFORMATION: DNA Oligo for sgRNA expression vector cloning

<400> SEQUENCE: 14
ctaaaacaga ggatccgcga ctgaagcggt gtttcgtcct ttccacaaga tat    53

<210> SEQ ID NO 15
<211> LENGTH: 54
<212> TYPE: DNA
<213> ORGANISM: Artificial Sequence
<220> FEATURE:
<223> OTHER INFORMATION: DNA Oligo for sgRNA expression vector cloning

<400> SEQUENCE: 15
ggaaaggacg aaacaccgga tggctacccc cactgcggtt ttagagctag aaat    54

<210> SEQ ID NO 16
<211> LENGTH: 53
<212> TYPE: DNA
<213> ORGANISM: Artificial Sequence
<220> FEATURE:
<223> OTHER INFORMATION: DNA Oligo for sgRNA expression vector cloning

<400> SEQUENCE: 16
ctaaaaccgc agtgggggta gccatccggt gtttcgtcct ttccacaaga tat    53

<210> SEQ ID NO 17
<211> LENGTH: 54
<212> TYPE: DNA
<213> ORGANISM: Artificial Sequence
<220> FEATURE:
<223> OTHER INFORMATION: DNA Oligo for sgRNA expression vector cloning

<400> SEQUENCE: 17
ggaaaggacg aaacaccgat cctagcccac tttcgaagtt ttagagctag aaat    54

<210> SEQ ID NO 18
<211> LENGTH: 53
<212> TYPE: DNA
<213> ORGANISM: Artificial Sequence
<220> FEATURE:
<223> OTHER INFORMATION: DNA primer

<400> SEQUENCE: 18
ctaaaacttc gaaagtgggc taggatcggt gtttcgtcct ttccacaaga tat    53

<210> SEQ ID NO 19
<211> LENGTH: 54
<212> TYPE: DNA
<213> ORGANISM: Artificial Sequence

```
<220> FEATURE:
<223> OTHER INFORMATION: DNA Oligo for sgRNA expression vector cloning

<400> SEQUENCE: 19
ggaaaggacg aaacaccgtg tcgtcgttgt gttgtgggtt ttagagctag aaat          54

<210> SEQ ID NO 20
<211> LENGTH: 53
<212> TYPE: DNA
<213> ORGANISM: Artificial Sequence
<220> FEATURE:
<223> OTHER INFORMATION: DNA Oligo for sgRNA expression vector cloning

<400> SEQUENCE: 20
ctaaaaccac aacacaacga cgacaccggt gtttcgtcct ttccacaaga tat           53

<210> SEQ ID NO 21
<211> LENGTH: 54
<212> TYPE: DNA
<213> ORGANISM: Artificial Sequence
<220> FEATURE:
<223> OTHER INFORMATION: DNA Oligo for sgRNA expression vector cloning

<400> SEQUENCE: 21
ggaaaggacg aaacaccgga gttgtgatca ttgtgaggtt ttagagctag aaat          54

<210> SEQ ID NO 22
<211> LENGTH: 53
<212> TYPE: DNA
<213> ORGANISM: Artificial Sequence
<220> FEATURE:
<223> OTHER INFORMATION: DNA Oligo for sgRNA expression vector cloning

<400> SEQUENCE: 22
ctaaaacctc acaatgatca caactccggt gtttcgtcct ttccacaaga tat           53

<210> SEQ ID NO 23
<211> LENGTH: 54
<212> TYPE: DNA
<213> ORGANISM: Artificial Sequence
<220> FEATURE:
<223> OTHER INFORMATION: DNA Oligo for sgRNA expression vector cloning

<400> SEQUENCE: 23
ggaaaggacg aaacaccgtt gggcaagacg cccccccggtt ttagagctag aaat         54

<210> SEQ ID NO 24
<211> LENGTH: 53
<212> TYPE: DNA
<213> ORGANISM: Artificial Sequence
<220> FEATURE:
<223> OTHER INFORMATION: DNA Oligo for sgRNA expression vector cloning

<400> SEQUENCE: 24
ctaaaaccgg gggcgtctt gcccaacggt gtttcgtcct ttccacaaga tat            53

<210> SEQ ID NO 25
<211> LENGTH: 54
<212> TYPE: DNA
<213> ORGANISM: Artificial Sequence
<220> FEATURE:
<223> OTHER INFORMATION: DNA Oligo for sgRNA expression vector cloning

<400> SEQUENCE: 25
ggaaaggacg aaacaccgtc agacgcactg acaaagtgtt ttagagctag aaat          54
```

<210> SEQ ID NO 26
<211> LENGTH: 53
<212> TYPE: DNA
<213> ORGANISM: Artificial Sequence
<220> FEATURE:
<223> OTHER INFORMATION: DNA Oligo for sgRNA expression vector cloning

<400> SEQUENCE: 26
ctaaaacact tgtcagtgc gtctgacggt gtttcgtcct ttccacaaga tat          53

<210> SEQ ID NO 27
<211> LENGTH: 54
<212> TYPE: DNA
<213> ORGANISM: Artificial Sequence
<220> FEATURE:
<223> OTHER INFORMATION: DNA Oligo for sgRNA expression vector cloning

<400> SEQUENCE: 27
ggaaaggacg aaacaccaga gagacggacg ctccaatgtt ttagagctag aaat         54

<210> SEQ ID NO 28
<211> LENGTH: 53
<212> TYPE: DNA
<213> ORGANISM: Artificial Sequence
<220> FEATURE:
<223> OTHER INFORMATION: DNA Oligo for sgRNA expression vector cloning

<400> SEQUENCE: 28
ctaaaacatt ggagcgtccg tctctctggt gtttcgtcct ttccacaaga tat          53

<210> SEQ ID NO 29
<211> LENGTH: 54
<212> TYPE: DNA
<213> ORGANISM: Artificial Sequence
<220> FEATURE:
<223> OTHER INFORMATION: DNA Oligo for sgRNA expression vector cloning

<400> SEQUENCE: 29
ggaaaggacg aaacaccggc ccagggaagc catcggagtt ttagagctag aaat         54

<210> SEQ ID NO 30
<211> LENGTH: 53
<212> TYPE: DNA
<213> ORGANISM: Artificial Sequence
<220> FEATURE:
<223> OTHER INFORMATION: DNA Oligo for sgRNA expression vector cloning

<400> SEQUENCE: 30
ctaaaactcc gatggcttcc ctgggccggt gtttcgtcct ttccacaaga tat          53

<210> SEQ ID NO 31
<211> LENGTH: 8842
<212> TYPE: DNA
<213> ORGANISM: Artificial Sequence
<220> FEATURE:
<223> OTHER INFORMATION: SerpinG1-plasmid

<400> SEQUENCE: 31
agacgtcatg caggaaagaa catgtgagca aaaggccagc aaaaggccag gaaccgtaaa    60
aaggccgcgt tgctggcgtt tttccatagg ctccgccccc ctgacgagca tcacaaaaat   120
cgacgctcaa gtcagaggtg gcgaaacccg acaggactat aaagatacca ggcgtttccc   180
cctggaagct ccctcgtgcg ctctcctgtt ccgaccctgc cgcttaccgg atacctgtcc   240
gcctttctcc cttcgggaag cgtggcgctt tctcaatgct cacgctgtag gtatctcagt   300

```
tcggtgtagg tcgttcgctc caagctgggc tgtgtgcacg aaccccccgt tcagcccgac      360
cgctgcgcct tatccggtaa ctatcgtctt gagtccaacc cggtaagaca cgacttatcg      420
ccactggcag cagccactgg taacaggatt agcagagcga ggtatgtagg cggtgctaca      480
gagttcttga agtggtggcc taactacggc tacactagaa ggacagtatt tggtatctgc      540
gctctgctga agccagttac cttcggaaaa agagttggta gctcttgatc cggcaaacaa      600
accaccgctg gtagcggtgg ttttttttgtt tgcaagcagc agattacgcg cagaaaaaaa      660
ggatctcaag aagatccttt gatcttttct acggggtctg acgctcagtg aacgaaaac      720 tcacgttaag ggattttggt catgagatta tcaaaaagga tcttcaccta gatccttta      780 aattaaaaat gaagttttaa atcaatctaa agtatatatg agtaaacttg gtctgacagt      840
taccaatgct taatcagtga ggcacctatc tcagcgatct gtctatttcg ttcatccata      900
gttgcctgac tccccgtcgt gtagataact acgatacggg agggcttacc atctggcccc      960
agtgctgcaa tgataccgcg agacccacgc tcaccggctc cagatttatc agcaataaac     1020
cagccagccg gaagggccga gcgcagaagt ggtcctgcaa ctttatccgc ctccatccag     1080
tctattaatt gttgccggga agctagagta agtagttcgc cagttaatag tttgcgcaac     1140
gttgttgcca ttgctacagg catcgtggtg tcacgctcgt cgtttggtat ggcttcattc     1200
agctccggtt cccaacgatc aaggcgagtt acatgatccc ccatgttgtg caaaaaagcg     1260
gttagctcct tcggtcctcc gatcgttgtc agaagtaagt tggccgcagt gttatcactc     1320
atggttatgg cagcactgca taattctctt actgtcatgc catccgtaag atgcttttct     1380
gtgactggtg agtactcaac caagtcattc tgagaatagt gtatgcggcg accgagttgc     1440
tcttgcccgg cgtcaatacg ggataatacc gcgccacata gcagaacttt aaaagtgctc     1500
atcattggaa aacgttcttc ggggcgaaaa ctctcaagga tcttaccgct gttgagatcc     1560
agttcgatgt aacccactcg tgcacccaac tgatcttcag catcttttac tttcaccagc     1620
gtttctgggt gagcaaaaac aggaaggcaa aatgccgcaa aaaagggaat aagggcgaca     1680
cggaaatgtt gaatactcat actcttcctt tttcaatatt attgaagcat ttatcagggt     1740
tattgtctca tgagcggata catatttgaa tgtatttaga aaaataaaca ataggggtt     1800 ccgcgcacat ttccccgaaa agtgccacct gacgtcgacg gatcgggaga tctcccgatc     1860
ccctatggtc gactctcagt acaatctgct ctgatgccgc atagttaagc cagtatctgc     1920
tccctgcttg tgtgttggag gtcgctgagt agtgcgcgag caaaatttaa gctacaacaa     1980
ggcaaggctt gaccgacaat tgcatgaaga atctgcttag ggttaggcgt tttgcgctgc     2040
ttcgcgacag acatgataag atacattgat gagtttggac aaaccacaac tagaatgcag     2100
tgaaaaaaat gctttatttg tgaaatttgt gatgctattg ctttatttgt aaccattata     2160
agctgcaata acaagttccg cggttagtt tttgtattgg aagggctggt cgccagtctc     2220
attgagaagg catgtgcgga cgatggcttc tgtcactgca aagggtcac aattggcaga     2280 ggggcggcgg tcttcaaagt aacctttctt ctcctggccg acagtccggg gaatgcggat     2340
gctggcactg cgattggcga caccagcaga aaagtcgttg atgttggacg tttcgtggaa     2400
cccagtcaga cgacgggcat tgtccaggcc ccccttggga tcgtaggctc gaatgtggta     2460
ccggtgccgc ttgcttagtt tctcgatggc ctcctcgatg tgcttcagac cattctcctc     2520
ccgcatggcc ttggtgctaa agttggtatg gcagcctgca ccattccagt tcccaggaat     2580
gggcttgggg tcaaaggttg ctattacccc aaagtcttca catactcgat gcaagatgaa     2640
```

```
acgggccacc cagagatgat ctcccatgcg gattccttca cagggtccta tttggaattc    2700
ccactgggca ggcatgacct cagcatttgt tcctgtaatc ttgacccag catacaagca     2760 ggcgcggtag tgagcctcca cgatatccct gccataggct ttgtctgcgc ccacaccaca    2820
gtaatacgga ccttggggcc caggaaagcc attggaaggc caaccaaaag ggtgcccatc    2880
tgttcccatc agagtatact cctgttccat tccaaaccag gggtgctggt tgctcaccat    2940
gtccattatc cgtttacacg agtgccttaa attggtctct gcaggcttcc ggttgtactt    3000
gaaaacttca cagaacacca gcttgttggg atctctgcgg aaggggtccc gaaacatggc    3060
aacagggctg agatacatgt cactgttgga gccctcagac tgaaaggtac tagagccatc    3120
aaaattccac tcaggtaact cttctacaca cttgggctca cagtccaggg tgcgggtttt    3180
gcagcgcagt ccttctccag taccatcaac ccagatatac atggcttgga ctttctcacc    3240
ctggggcagg cacaagtaca tttgcttgat gttttttgttc aagtgggaac ttgctgaggt  3300
ggccatatcg atcgaaaatg gatatacaag ctcccgggag cttttttgcaa aagcctaggc  3360 ctccaaaaaa gcctcctcac tacttctgga atagctcaga ggcagaggcg gcctcggcct    3420
ctgcataaat aaaaaaaatt agtcagccat ggggcggaga atgggcggaa ctgggcggag    3480
ttaggggcgg gatgggcgga gttaggggcg ggactatggt tgctgactaa ttgagatgca    3540
tgctttgcat acttctgcct gctggggagc ctggggactt tccacacctg gttgctgact    3600
aattgagatg catgctttgc atacttctgc ctgctgggga gcctggggac tttccacacc    3660
ctaactgaca cacattccac agacgtcgct cgatgtacgg ccagatata cgcgtagtca     3720 atgggaaaaa cccattggag ccaagtacac tgactcaata gggactttcc attgggtttt    3780
gcccagtaca taaggtcaat aggggtgag tcaacaggaa agtcccattg agccaagta     3840 cattgagtca atagggactt tccaatgggt tttgcccagt acataaggtc aatgggaggt    3900
aagccaatgg ttttttccca ttactgacat gtatactgag tcattaggga ctttccaatg    3960
ggttttgccc agtacataag gtcaataggg gtgaatcaac aggaaagtcc cattggagcc    4020
aagtacactg agtcaatagg gactttccat tgggttttgc ccagtacaaa aggtcaatag    4080
ggggtgagtc aatgggtttt tcccattatt ggcacataca taaggtcaat aggggtgact    4140
agtcagtggg cagagcgcac atcgcccaca gtccccgaga agttgggggg aggggtcggc    4200
aattgaaccg gtgcctagag aaggtggcgc gggggtaaact gggaaagtga tgtcgtgtac   4260
tggctccgcc tttttcccga gggtggggga gaaccgtata taagtgcagt agttgccgtg   4320
aacgttcttt ttcgcaacgg gtttgccgcc agaacacagc tgaagcttcg aggggctcgc    4380
atctctcctt cacgcgcccg ccgccctacc tgaggccgcc atccacgccg gttgagtcgc    4440
gttctgccgc ctcccgcctg tggtgcctcc tgaactgcgt ccgccgtcta ggtaagttta    4500
aagctcaggt cgagaccggg cctttgtccg gcgctccctt ggagcctacc tagactcagc    4560
cggctctcca cgctttgcct gaccctgctt gctcaactct acgtctttgt ttcgttttct    4620
gttctgcgcc gttacagatc caagctgtga ccggcgccta cagtgcgatc gccaccatgg    4680
ccagcagact gacactgctg accctgctgc tcctcctgct ggctggagac agggcttcct    4740
ccaaccccaa cgccaccagc agcagctccc aggaccctga gtccctccag gacaggggag    4800
aaggcaaggt cgccaccacc gtcatctcca aaatgctctt cgtcgagccc atcctcgagg    4860
tcagctccct ccccaccaca aacagcacaa ccaacagcgc caccaagatc accgccaaca    4920
ccaccgacga acccacaacc cagcccacca cagagcctac aacacagcct accatccagc    4980
ctacccaacc caccacccag ctccctaccg actcccctac ccagcctacc acaggctcct    5040
```

```
tttgtcccgg acctgtgacc ctgtgctccg acctggagtc ccatagcaca gaggctgtcc    5100
tcggagatgc cctggtggat ttcagcctca aactctacca cgccttcagc gccatgaaga    5160
aggtcgagac caatatggcc ttctccccct ttagcatcgc cagcctgctc acccaagtcc    5220
tgctcggagc cggcgagaat accaagacca acctggagag catcctgtcc tacccctaagg   5280 acttcacctg cgtccaccag gccctcaagg gctttaccac caaaggagtc acatccgtca    5340
gccagatctt ccattcccct gacctcgcca ttagggacaa attcgtgaac gcctccagga    5400
ccctgtacag cagctcccct agggtcctgt ccaacaacag cgacgccaac ctggagctca    5460
ttaatacatg ggtggccaag aatacaaaca acaagattag caggctcctg gatagcctgc    5520
cttccgacac caggctcgtg ctcctcaatg ccatctacct ctccgccaag tggaagacca    5580
cattcgaccc caagaaaaca aggatggagc cctttcactt taaaaatagc gtgatcaagg    5640
tgcccatgat gaacagcaag aagtaccctg tcgcccactt catcgaccag accctgaagg    5700
ctaaggtggg cacagctccaa ctgtcccata atctgagcct ggtcatcctc gtgcctcaga    5760
acctgaagca caggctggag gacatggaac aggccctgtc ccccagcgtg tttaaggcca    5820
tcatggaaaa actcgagatg tccaagtttc aacccaccct cctcaccctg cccagaatta    5880
aggtcaccac aagccaggac atgctcagca ttatggagaa gctcgagttc ttcgatttct    5940
cctacgacct caacctctgc ggcctgacag aagaccctga cctgcaggtg agcgccatgc    6000
agcaccagac agtgctggag ctcaccgaga caggagtgga agctgctgcc gcctccgcta    6060
tttccgtggc caggaccctc ctggtgttcg aggtgcaaca accttcctg ttcgtcctgt    6120 gggaccaaca acacaagttc cctgtgttca tgggcagagt ctacgacccc agagcctgaa    6180
cacagtctct gtgccttcta gttgccagcc atctgttgtt tgcccctccc ccgtgccttc    6240
cttgaccctg gaaggtgcca ctcccactgt cctttcctaa taaaatgagg aaattgcatc    6300
gcattgtctg agtaggtgtc attctattct ggggggtggg gtgggcagg acagcaaggg    6360 ggaggattgg gaagacaata gcaggcatgc tggggatgcg gtgggctcta tggattaagc    6420
tcgcgtagtc aatgggaaaa acccattgga gccaagtaca ctgactcaat agggactttc    6480
cattgggttt tgcccagtac ataaggtcaa taggggtga gtcaacagga aagtcccatt    6540
ggagccaagt acattgagtc aatagggact ttccaatggg ttttgcccag tacataaggt    6600
caatgggagg taagccaatg ggttttccc attactgaca tgtatactga gtcattaggg    6660
actttccaat gggttttgcc cagtacataa ggtcaatagg ggtgaatcaa caggaaagtc    6720
ccattggagc caagtacact gagtcaatag ggactttcca ttgggttttg cccagtacaa    6780
aaggtcaata gggggtgagt caatgggttt ttcccattat tggcacatac ataaggtcaa    6840 tagggggtgac tagtcagtgg gcagagcgca catcgcccac agtccccgag aagttggggg    6900
gaggggtcgg caattgaacc ggtgcctaga aaggtggcg cggggtaaac tgggaaagtg    6960
atgtcgtgta ctggctccgc cttttctcccg agggtggggg agaaccgtat ataagtgcag    7020
tagttgccgt gaacgttctt tttcgcaacg ggtttgccgc cagaacacag ctgaagcttc    7080
gaggggctcg catctctcct tcacgcgccc gccgccctac ctgaggccgc catccacgcc    7140
ggttgagtcg cgttctgccg cctccgcct gtggtgcctc ctgaactgcg tccgccgtct    7200
aggtaagttt aaagctcagg tcgagaccgg gcctttgtcc ggcgctccct tggagcctac    7260
ctagactcag ccggctctcc acgctttgcc tgacccctgct tgctcaactc tacgtctttg    7320
tttcgttttc tgttctgcgc cgttacagat ccaagctgtg accggcgcct acagtgcgat    7380
```

```
cgccaccatg atccacacca acctgaagaa gaaattctcc tgctgcgtgc tggtgttcct    7440
gctgttcgcc gtgatctgcg tgtggaaaga gaagaagaag ggctcctact acgactcctt    7500
caagctgcag accaaagaat tccaggtgct gaagtccctg ggcaagctgg ccatgggctc    7560
cgactctcag tccgtgtcct ccagctctac ccaggacccc cacagaggca gacagaccct    7620
gggctctctg agaggcctgg ccaaggctaa gcctgaggcc tccttccagg tgtggaacaa    7680
ggactcctcc agcaagaacc tgatcccccg gctgcagaag atctggaaga actacctgtc    7740
catgaacaag tacaaggtgt cctacaaggg ccctggccct ggcatcaagt tctctgccga    7800
ggccctgaga tgccacctga ggaccatgt gaacgtgtcc atggtggaag tgaccgactt    7860
cccattcaac acctccgagt gggagggcta cctgcccaaa gagtccatcc ggaccaaggc    7920
tggcccttgg ggcagatgtg ctgtggtgtc ctctgccggc tccctgaagt cctctcagct    7980
gggcagagag atcgacgacc acgacgccgt gctgcggttt aatggcgccc ctaccgccaa    8040
cttccagcag gacgtgggca ccaagaccac catccggctg atgaactccc agctcgtgac    8100
aaccgagaag cggttcctga aggactccct gtacaacgag ggcatcctga tcgtgtggga    8160
cccctccgtg taccactccg acatccccaa gtggtatcag aaccccgact acaacttctt    8220
caacaactac aagacctacc ggaagctgca ccccaaccag cccttctaca tcctgaagcc    8280
ccagatgccc tgggagctgt gggacattct gcaggaaatc tcccccgagg aaatccagcc    8340
caacccccct tcctctggca tgctgggcat cattatcatg atgaccctgt gcgaccaggt    8400
ggacatctac gagtttctgc cctccaagag aaagaccgac gtgtgctact actaccagaa    8460
gttcttcgac tccgcctgca ccatgggcgc ctaccaccct ctgctgtacg agaagaacct    8520
cgtgaagcac ctgaaccagg gcaccgacga ggatatctac ctgctgggca aggccaccct    8580
gcctggcttc agaaccatcc actgctgaac acagtctctg tgccttctag ttgccagcca    8640
tctgttgttt gcccctcccc cgtgccttcc ttgaccctgg aaggtgccac tcccactgtc    8700
ctttcctaat aaaatgagga aattgcatcg cattgtctga gtaggtgtca ttctattctg    8760
gggggtgggg tggggcagga cagcaagggg gaggattggg aagacaatag caggcatgct    8820
ggggatgcgg tgggctctat gg                                             8842

<210> SEQ ID NO 32
<211> LENGTH: 8596
<212> TYPE: DNA
<213> ORGANISM: Artificial Sequence
<220> FEATURE:
<223> OTHER INFORMATION: A1AT plasmid

<400> SEQUENCE: 32
agacgtcatg caggaaagaa catgtgagca aaaggccagc aaaaggccag gaaccgtaaa      60
aaggccgcgt tgctggcgtt tttccatagg ctccgccccc ctgacgagca tcacaaaaat    120
cgacgctcaa gtcagaggtg gcgaaacccg acaggactat aaagatacca ggcgtttccc    180
cctggaagct ccctcgtgcg ctctcctgtt ccgaccctgc cgcttaccgg atacctgtcc    240
gcctttctcc cttcgggaag cgtggcgctt tctcaatgct cacgctgtag gtatctcagt    300
tcggtgtagg tcgttcgctc caagctgggc tgtgtgcacg aaccccccgt tcagcccgac    360
cgctgcgcct tatccggtaa ctatcgtctt gagtccaacc cggtaagaca cgacttatcg    420
ccactggcag cagccactgg taacaggatt agcagagcga ggtatgtagg cggtgctaca    480
gagttcttga agtggtggcc taactacggc tacactagaa ggacagtatt tggtatctgc    540
gctctgctga agccagttac cttcggaaaa agagttggta gctcttgatc cggcaaacaa    600
```

```
accaccgctg gtagcggtgg ttttttttgtt tgcaagcagc agattacgcg cagaaaaaaa    660
ggatctcaag aagatccttt gatcttttct acggggtctg acgctcagtg gaacgaaaac    720
tcacgttaag ggattttggt catgagatta tcaaaaagga tcttcaccta gatccttta     780
aattaaaaat gaagttttaa atcaatctaa agtatatatg agtaaacttg gtctgacagt    840
taccaatgct taatcagtga ggcacctatc tcagcgatct gtctatttcg ttcatccata    900
gttgcctgac tccccgtcgt gtagataact acgatacggg agggcttacc atctggcccc    960
agtgctgcaa tgataccgcg agacccacgc tcaccggctc cagatttatc agcaataaac   1020
cagccagccg aagggccgag cgcagaagt ggtcctgcaa ctttatccgc ctccatccag    1080
tctattaatt gttgccggga agctagagta agtagttcgc cagttaatag tttgcgcaac   1140
gttgttgcca ttgctacagg catcgtggtg tcacgctcgt cgtttggtat ggcttcattc   1200
agctccggtt cccaacgatc aaggcgagtt acatgatccc ccatgttgtg caaaaaagcg   1260
gttagctcct tcggtcctcc gatcgttgtc agaagtaagt tggccgcagt gttatcactc   1320
atggttatgg cagcactgca taattctctt actgtcatgc catccgtaag atgcttttct   1380
gtgactggtg agtactcaac caagtcattc tgagaatagt gtatgcggcg accgagttgc   1440
tcttgcccgg cgtcaatacg ggataatacc gcgccacata gcagaacttt aaaagtgctc   1500
atcattggaa aacgttcttc ggggcgaaaa ctctcaagga tcttaccgct gttgagatcc   1560
agttcgatgt aacccactcg tgcacccaac tgatcttcag catcttttac tttcaccagc   1620
gtttctgggt gagcaaaaac aggaaggcaa aatgccgcaa aaaagggaat aagggcgaca   1680
cggaaatgtt gaatactcat actcttcctt tttcaatatt attgaagcat ttatcagggt   1740
tattgtctca tgagcggata catatttgaa tgtatttaga aaataaaca aatagggggtt   1800
ccgcgcacat ttccccgaaa agtgccacct gacgtcgacg gatcgggaga tctcccgatc   1860
ccctatggtc gactctcagt acaatctgct ctgatgccgc atagttaagc cagtatctgc   1920
tccctgcttg tgtgttggag gtcgctgagt agtgcgcgag caaaatttaa gctacaacaa   1980
ggcaaggctt gaccgacaat tgcatgaaga atctgcttag ggttaggcgt tttgcgctgc   2040
ttcgcgacag acatgataag atacattgat gagtttggac aaaccacaac tagaatgcag   2100
tgaaaaaaat gctttattg tgaaatttgt gatgctattg ctttatttgt aaccattata   2160
agctgcaata aacaagttcc gcggttagtt tttgtattgg aagggctggt cgccagtctc   2220
attgagaagg catgtgcgga cgatggcttc tgtcactgca aaggggtcac aattggcaga   2280
ggggcggcgg tcttcaaagt aacctttctt ctcctggccg acagtccggg gaatgcggat   2340
gctggcactg cgattggcga caccagcaga aaagtcgttg atgttggacg tttcgtggaa   2400
cccagtcaga cgacgggcat tgtccaggcc ccccttggga tcgtaggctc gaatgtggta   2460
ccggtgccgc ttgcttagtt tctcgatggc ctcctcgatg tgcttcagac cattctcctc   2520
ccgcatggcc ttggtgctaa agttggtatg gcagcctgca ccattccagt tcccaggaat   2580
gggcttgggg tcaaaggttg ctattacccc aaagtcttca catactcgat gcaagatgaa   2640
acgggccacc cagagatgat ctcccatgcg gattccttca cagggtccta tttggaattc   2700
ccactgggca ggcatgacct cagcatttgt tcctgtaatc ttgaccccag catacaagca   2760
ggcgcggtag tgagcctcca cgatatccct gccataggct ttgtctgcgc ccacaccaca   2820
gtaatacgga ccttgggcc caggaaagcc attggaaggc caaccaaaag ggtgcccatc   2880
tgttcccatc agagtatact cctgttccat tccaaaccag gggtgctggt tgctcaccat   2940
```

```
gtccattatc cgtttacacg agtgccttaa attggtctct gcaggcttcc ggttgtactt     3000
gaaaacttca cagaacacca gcttgttggg atctctgcgg aagggtccc gaaacatggc      3060
aacagggctg agatacatgt cactgttgga gccctcagac tgaaaggtac tagagccatc    3120
aaaattccac tcaggtaact cttctacaca cttgggctca cagtccaggg tgcgggtttt    3180
gcagcgcagt ccttctccag taccatcaac ccagatatac atggcttgga ctttctcacc    3240
ctggggcagg cacaagtaca tttgcttgat gtttttgttc aagtgggaac ttgctgaggt    3300
ggccatatcg atcgaaaatg gatatacaag ctcccgggag cttttgcaa aagcctaggc     3360
ctccaaaaaa gcctcctcac tacttctgga atagctcaga ggcagaggcg gcctcggcct    3420
ctgcataaat aaaaaaaatt agtcagccat ggggcggaga atgggcggaa ctgggcggag    3480
ttaggggcgg gatgggcgga gttaggggcg ggactatggt tgctgactaa ttgagatgca    3540
tgctttgcat acttctgcct gctggggagc ctggggactt ccacacctg gttgctgact     3600
aattgagatg catgctttgc atacttctgc ctgctgggga gcctgggac tttccacacc     3660
ctaactgaca cacattccac agacgtcgct cgatgtacgg gccagatata cgcgtagtca    3720
atggaaaaaa cccattggag ccaagtacac tgactcaata gggactttcc attgggtttt    3780
gcccagtaca taaggtcaat aggggtgag tcaacaggaa agtcccattg gagccaagta     3840
cattgagtca atagggactt tccaatgggt tttgcccagt acataaggtc aatgggaggt    3900
aagccaatgg gttttttccca ttactgacat gtatactgag tcattaggga ctttccaatg   3960
ggttttgccc agtacataag gtcaataggg gtgaatcaac aggaaagtcc cattggagcc    4020
aagtacactg agtcaatagg gactttccat tgggttttgc ccagtacaaa aggtcaatag    4080
ggggtgagtc aatgggtttt tcccattatt ggcacataca taaggtcaat agggggtgact   4140
agtcagtggg cagagcgcac atcgcccaca gtccccgaga gttgggggg aggggtcggc     4200
aattgaaccg gtgcctagag aaggtggcgc ggggtaaact gggaaagtga tgtcgtgtac    4260
tggctccgcc tttttcccga gggtgggga aaccgtata aagtgcagt agttgccgtg       4320
aacgttctt ttcgcaacgg gtttgccgcc agaacacagc tgaagcttcg aggggctcgc     4380
atctctcctt cacgcgcccg ccgcccacc tgaggccgcc atccacgccg gttgagtcgc     4440
gttctgccgc ctcccgcctg tggtgcctcc tgaactgcgt ccgccgtcta ggtaagttta    4500
aagctcaggt cgagaccggg cctttgtccg gcgctccctt ggagcctacc tagactcagc    4560
cggctctcca cgctttgcct gaccctgctt gctcaactct acgtctttgt ttcgtttttct   4620
gttctgcgcc gttacagatc caagctgtga ccggcgccta cagtgcgatc gccaccatgc    4680
ccagctccgt gagctggggc attctcctcc tcgctggcct gtgctgtctg gtgcctgtga    4740
gcctggccga agacccccaa ggagacgctg ctcagaagac agacatcc caccatgacc      4800
aggaccaccc caccttcaat aagatcaccc ctaacctcgc tgagtttgcc tttccctct     4860
acaggcaact ggcccaccag agcaactcca ccaatatctt cttttagccct gtgagcatcg    4920
ccacagcctt cgccatgctg agcctgggca ccaaggctga tacacatgac gagatcctgg    4980
aaggactgaa cttcaacctg accgagatcc ccgaggccca gatccacgag ggcttccagg    5040
aactgctgag gaccctgaac cagcctgaca gccagctcca gctcaccacc ggcaatggcc    5100
tcttcctgag cgagggcctc aagctcgtgg ataagttcct ggaagacgtg aagaagctgt    5160
accactccga agccttcaca gtgaactttg gcgacacaga ggaggccaag aagcagatca    5220
acgactatgt ggagaagggc acccagggca agatcgtgga cctcgtgaag gagctggata    5280
gggacaccgt gttcgctctc gtgaactata tcttcttcaa gggcaagtgg gagaggccct    5340
```

```
tcgaggtgaa agacacagag gaagaggact tccacgtcga ccaagtgacc acagtcaagg    5400
tccccatgat gaagagactg ggcatgttca acatccagca ttgcaaaaag ctgagcagct    5460
gggtgctgct catgaagtat ctcggcaacg ccacagccat cttcttcctg cccgatgagg    5520
gcaagctcca gcatctggaa aacgagctca cccacgacat tatcaccaag tttctggaga    5580
acgaagacag gaggagcgct agcctccacc tccccaaact cagcatcacc ggcacatatg    5640
acctgaagtc cgtcctcggc cagctgggca tcacaaaggt cttctccaac ggcgccgacc    5700
tgagcggagt cacagaagag gctcccctga agctgagcaa ggctgtgcat aaggccgtgc    5760
tgacaattga cgagaaaggc acagaggctg ccggagccat gttcctggaa gctatcccca    5820
tgagcatccc ccccgaggtg aaattcaaca aaccccttcgt gttcctgatg atcgagcaga    5880
acaccaagtc cccctcttc atgggcaagg tcgtgaaccc cacccagaag taaacacagt    5940
ctctgtgcct tctagttgcc agccatctgt tgtttgcccc tcccccgtgc cttccttgac    6000
cctggaaggt gccactccca ctgtcctttc taataaaat gaggaaattg catcgcattg    6060
tctgagtagg tgtcattcta ttctgggggg tggggtgggg caggacagca agggggagga    6120
ttgggaagac aatagcaggc atgctgggga tgcggtgggc tctatggatt aagctcgcgt    6180
agtcaatggg aaaaacccat tggagccaag tacactgact caataggac tttccattgg    6240 gttttgccca gtacataagg tcaataggg gtgagtcaac aggaaagtcc cattggagcc    6300
aagtacattg agtcaatagg gactttccaa tgggttttgc ccagtacata aggtcaatgg    6360
gaggtaagcc aatgggtttt tcccattact gacatgtata ctgagtcatt agggactttc    6420
caatgggttt tgcccagtac ataaggtcaa taggggtgaa tcaacaggaa agtcccattg    6480
gagccaagta cactgagtca ataggggactt tccattgggt tttgcccagt acaaaaggtc    6540
aatagggggt gagtcaatgg gttttttccca ttattggcac atacataagg tcaatagggg    6600
tgactagtca gtgggcagag cgcacatcgc ccacagtccc cgagaagttg gggggagggg    6660
tcggcaattg aaccggtgcc tagagaaggt ggcgcggggt aaactgggaa agtgatgtcg    6720
tgtactggct ccgccttttt cccgagggtg ggggagaacc gtatataagt gcagtagttg    6780
ccgtgaacgt tcttttttcgc aacgggtttg ccgcagaaac acagctgaag cttcgagggg    6840
ctcgcatctc tccttcacgc gcccgccgcc ctacctgagg ccgccatcca cgccggttga    6900
gtcgcgttct gccgcctccc gcctgtggtg cctcctgaac tgcgtccgcc gtctaggtaa    6960
gtttaaagct caggtcgaga ccgggccttt gtccggcgct cccttggagc ctacctagac    7020
tcagccggct ctccacgctt tgcctgaccc tgcttgctca actctacgtc tttgtttcgt    7080
tttctgttct gcgccgttac agatccaagc tgtgaccggc gcctacagtg cgatcgccac    7140
catgatccac accaacctga gaagaaatt tcctgctgc gtgctggtgt tcctgctgtt    7200
cgccgtgatc tgcgtgtgga agagaagaa gaagggctcc tactacgact ccttcaagct    7260
gcagaccaaa gaattccagg tgctgaagtc cctgggcaag ctggccatgg gctccgactc    7320
tcagtccgtg tcctccagct ctacccagga ccccacagaga ggcagacaga ccctgggctc    7380
tctgagaggc ctggccaagg ctaagcctga ggcctccttc caggtgtgga acaaggactc    7440
ctccagcaag aacctgatcc cccggctgca gaagatctgg aagaactacc tgtccatgaa    7500
caagtacaag gtgtcctaca agggccctgg ccctggcatc aagttctctg ccgaggccct    7560
gagatgccac ctgagggacc atgtgaacgt gtccatggtg gaagtgaccg acttcccatt    7620
caacacctcc gagtgggagg gctacctgcc caaagagtcc atccggacca aggctggccc    7680
```

```
ttggggcaga tgtgctgtgg tgtcctctgc cggctccctg aagtcctctc agctgggcag    7740
agagatcgac gaccacgacg ccgtgctgcg gtttaatggc gccctaccg ccaacttcca     7800 gcaggacgtg ggcaccaaga ccaccatccg gctgatgaac tcccagctcg tgacaaccga    7860
gaagcggttc ctgaaggact ccctgtacaa cgagggcatc ctgatcgtgt gggacccctc    7920
cgtgtaccac tccgacatcc ccaagtggta tcagaacccc gactacaact tcttcaacaa    7980
ctacaagacc taccggaagc tgcaccccaa ccagcccttc tacatcctga gccccagat    8040 gccctgggag ctgtgggaca ttctgcagga aatctccccc gaggaaatcc agcccaaccc    8100
cccttcctct ggcatgctgg gcatcattat catgatgacc ctgtgcgacc aggtggacat    8160
ctacgagttt ctgccctcca agagaaagac cgacgtgtgc tactactacc agaagttctt    8220
cgactccgcc tgcaccatgg gcgcctacca ccctctgctg tacgagaaga acctcgtgaa    8280
gcacctgaac cagggcaccg acgaggatat ctacctgctg ggcaaggcca ccctgcctgg    8340
cttcagaacc atccactgct gaacacagtc tctgtgcctt ctagttgcca gccatctgtt    8400 gtttgccct ccccgtgcc ttccttgacc ctggaaggtg ccactccac tgtcctttcc      8460 taataaaatg aggaaattgc atcgcattgt ctgagtaggt gtcattctat tctgggggt    8520 ggggtgggc aggacagcaa gggggaggat tgggaagaca atagcaggca tgctgggat     8580 gcggtgggct ctatgg                                                   8596
```

<210> SEQ ID NO 33
<211> LENGTH: 33
<212> TYPE: DNA
<213> ORGANISM: Artificial Sequence
<220> FEATURE:
<223> OTHER INFORMATION: DNA forward primeroverhang

<400> SEQUENCE: 33
tcgtcggcag cgtcagatgt gtataagaga cag                                33

<210> SEQ ID NO 34
<211> LENGTH: 34
<212> TYPE: DNA
<213> ORGANISM: Artificial Sequence
<220> FEATURE:
<223> OTHER INFORMATION: DNA reverse primer overhang

<400> SEQUENCE: 34
gtctcgtggg ctcggagatg tgtataagag acag                               34

<210> SEQ ID NO 35
<211> LENGTH: 56
<212> TYPE: DNA
<213> ORGANISM: Artificial Sequence
<220> FEATURE:
<223> OTHER INFORMATION: DNA primer

<400> SEQUENCE: 35
tcgtcggcag cgtcagatgt gtataagaga caggacagac agaaggcaaa tctacg       56

<210> SEQ ID NO 36
<211> LENGTH: 57
<212> TYPE: DNA
<213> ORGANISM: Artificial Sequence
<220> FEATURE:
<223> OTHER INFORMATION: DNA primer

<400> SEQUENCE: 36
gtctcgtggg ctcggagatg tgtataagag acagttaaca gctacacagg aagagca      57

<210> SEQ ID NO 37
<211> LENGTH: 53
<212> TYPE: DNA
<213> ORGANISM: Artificial Sequence
<220> FEATURE:
<223> OTHER INFORMATION: DNA primer

<400> SEQUENCE: 37
tcgtcggcag cgtcagatgt gtataagaga cagggatgg ggtgtatgga ggt        53

<210> SEQ ID NO 38
<211> LENGTH: 54
<212> TYPE: DNA
<213> ORGANISM: Artificial Sequence
<220> FEATURE:
<223> OTHER INFORMATION: DNA primer

<400> SEQUENCE: 38
gtctcgtggg ctcggagatg tgtataagag acagttgcag actgctctcc ttgg       54

<210> SEQ ID NO 39
<211> LENGTH: 57
<212> TYPE: DNA
<213> ORGANISM: Artificial Sequence
<220> FEATURE:
<223> OTHER INFORMATION: DNA primer

<400> SEQUENCE: 39
tcgtcggcag cgtcagatgt gtataagaga cagcatgaat ctcatggttt cctttgt    57

<210> SEQ ID NO 40
<211> LENGTH: 57
<212> TYPE: DNA
<213> ORGANISM: Artificial Sequence
<220> FEATURE:
<223> OTHER INFORMATION: DNA primer

<400> SEQUENCE: 40
gtctcgtggg ctcggagatg tgtataagag acaggcttca agactcaact ctttccc    57

<210> SEQ ID NO 41
<211> LENGTH: 53
<212> TYPE: DNA
<213> ORGANISM: Artificial Sequence
<220> FEATURE:
<223> OTHER INFORMATION: DNA primer

<400> SEQUENCE: 41
tcgtcggcag cgtcagatgt gtataagaga cagggaaac agcatgggca aac         53

<210> SEQ ID NO 42
<211> LENGTH: 54
<212> TYPE: DNA
<213> ORGANISM: Artificial Sequence
<220> FEATURE:
<223> OTHER INFORMATION: DNA primer

<400> SEQUENCE: 42
gtctcgtggg ctcggagatg tgtataagag acagactgga atgtggatgg tggc       54

<210> SEQ ID NO 43
<211> LENGTH: 53
<212> TYPE: DNA
<213> ORGANISM: Artificial Sequence
<220> FEATURE:

<223> OTHER INFORMATION: DNA primer

<400> SEQUENCE: 43
tcgtcggcag cgtcagatgt gtataagaga cagacacctg atgaccacat cgt        53

<210> SEQ ID NO 44
<211> LENGTH: 54
<212> TYPE: DNA
<213> ORGANISM: Artificial Sequence
<220> FEATURE:
<223> OTHER INFORMATION: DNA primer

<400> SEQUENCE: 44
gtctcgtggg ctcggagatg tgtataagag acaggcaggg tccacttctg gatt       54

<210> SEQ ID NO 45
<211> LENGTH: 56
<212> TYPE: DNA
<213> ORGANISM: Artificial Sequence
<220> FEATURE:
<223> OTHER INFORMATION: DNA primer

<400> SEQUENCE: 45
tcgtcggcag cgtcagatgt gtataagaga cagtcactgt cttactaccc acagga     56

<210> SEQ ID NO 46
<211> LENGTH: 59
<212> TYPE: DNA
<213> ORGANISM: Artificial Sequence
<220> FEATURE:
<223> OTHER INFORMATION: DNA primer

<400> SEQUENCE: 46
gtctcgtggg ctcggagatg tgtataagag acagtccttt cattatattc aagagccac  59

<210> SEQ ID NO 47
<211> LENGTH: 53
<212> TYPE: DNA
<213> ORGANISM: Artificial Sequence
<220> FEATURE:
<223> OTHER INFORMATION: DNA primer

<400> SEQUENCE: 47
tcgtcggcag cgtcagatgt gtataagaga cagctcaccc accggagaaa cag        53

<210> SEQ ID NO 48
<211> LENGTH: 54
<212> TYPE: DNA
<213> ORGANISM: Artificial Sequence
<220> FEATURE:
<223> OTHER INFORMATION: DNA primer

<400> SEQUENCE: 48
gtctcgtggg ctcggagatg tgtataagag acagagaagg caagcaattc ggga       54

<210> SEQ ID NO 49
<211> LENGTH: 53
<212> TYPE: DNA
<213> ORGANISM: Artificial Sequence
<220> FEATURE:
<223> OTHER INFORMATION: DNA primer

<400> SEQUENCE: 49
tcgtcggcag cgtcagatgt gtataagaga cagtgccccc atgactaggg ata        53

```
<210> SEQ ID NO 50
<211> LENGTH: 55
<212> TYPE: DNA
<213> ORGANISM: Artificial Sequence
<220> FEATURE:
<223> OTHER INFORMATION: DNA primer

<400> SEQUENCE: 50
gtctcgtggg ctcggagatg tgtataagag acagtctgcg ttcgagaagc tgaaa         55

<210> SEQ ID NO 51
<211> LENGTH: 55
<212> TYPE: DNA
<213> ORGANISM: Artificial Sequence
<220> FEATURE:
<223> OTHER INFORMATION: DNA primer

<400> SEQUENCE: 51
tcgtcggcag cgtcagatgt gtataagaga cagcgtggag taacttacct gctgt         55

<210> SEQ ID NO 52
<211> LENGTH: 54
<212> TYPE: DNA
<213> ORGANISM: Artificial Sequence
<220> FEATURE:
<223> OTHER INFORMATION: DNA primer

<400> SEQUENCE: 52
gtctcgtggg ctcggagatg tgtataagag acagaagtgg tgagtgtgtc ctgt          54

<210> SEQ ID NO 53
<211> LENGTH: 51
<212> TYPE: DNA
<213> ORGANISM: Artificial Sequence
<220> FEATURE:
<223> OTHER INFORMATION: DNA primer

<400> SEQUENCE: 53
tcgtcggcag cgtcagatgt gtataagaga cagcaaccag cacccctggt t             51

<210> SEQ ID NO 54
<211> LENGTH: 53
<212> TYPE: DNA
<213> ORGANISM: Artificial Sequence
<220> FEATURE:
<223> OTHER INFORMATION: DNA primer

<400> SEQUENCE: 54
gtctcgtggg ctcggagatg tgtataagag acagcagctg ccagtctgtt tgc           53
```